United States Patent
White et al.

(10) Patent No.: US 9,511,079 B2
(45) Date of Patent: *Dec. 6, 2016

(54) METHODS FOR THE TREATMENT OF FIBROMYALGIA AND CHRONIC FATIGUE SYNDROME

(75) Inventors: Hillary D. White, S. Pomfret, VT (US); Robert Gyurik, Exeter, NH (US)

(73) Assignee: White Mountain Pharma, Inc., New York, NY (US)

( * ) Notice: Subject to any disclaimer, the term of this patent is extended or adjusted under 35 U.S.C. 154(b) by 415 days.

This patent is subject to a terminal disclaimer.

(21) Appl. No.: 13/988,259

(22) PCT Filed: Nov. 17, 2011

(86) PCT No.: PCT/US2011/061256
§ 371 (c)(1),
(2), (4) Date: Oct. 4, 2013

(87) PCT Pub. No.: WO2012/074774
PCT Pub. Date: Jun. 7, 2012

(65) Prior Publication Data
US 2014/0031326 A1    Jan. 30, 2014

Related U.S. Application Data

(63) Continuation-in-part of application No. 12/949,644, filed on Nov. 18, 2010, now Pat. No. 8,883,769.
(Continued)

(51) Int. Cl.
| | | |
|---|---|---|
| *A61K 31/56* | (2006.01) | |
| *A61K 31/585* | (2006.01) | |
| *A61K 31/568* | (2006.01) | |
| *A61K 31/5685* | (2006.01) | |
| *A61K 31/58* | (2006.01) | |
| *A61K 31/37* | (2006.01) | |
| *A61K 31/57* | (2006.01) | |
| *A61K 9/00* | (2006.01) | |
| *A61K 9/06* | (2006.01) | |

(52) U.S. Cl.
CPC .......... *A61K 31/585* (2013.01); *A61K 9/0014* (2013.01); *A61K 9/06* (2013.01); *A61K 31/37* (2013.01); *A61K 31/56* (2013.01); *A61K 31/568* (2013.01); *A61K 31/5685* (2013.01); *A61K 31/57* (2013.01); *A61K 31/58* (2013.01)

(58) Field of Classification Search
USPC .................................................. 514/170, 182
See application file for complete search history.

(56) References Cited

U.S. PATENT DOCUMENTS 6,165,504 A    12/2000  Bell
7,799,769 B2   9/2010   White
(Continued)

OTHER PUBLICATIONS

PCT Search Report related to Application No. PCT/US2011/061254, mailed Mar. 29, 2012.
(Continued)

*Primary Examiner* — San-Ming Hui
(74) *Attorney, Agent, or Firm* — Loeb & Loeb LLP

(57) ABSTRACT

The invention relates to methods for the treatment of fibromyalgia and chronic fatigue syndrome by administration of a transdermally applied androgen composition. The treatment is both safe and effective for treating fibromyalgia-related pain and fatigue, as well as chronic fatigue syndrome.

15 Claims, 33 Drawing Sheets

Related U.S. Application Data which is a continuation-in-part of application No. 12/837,310, filed on Jul. 15, 2010, now Pat. No. 8,999,963, which is a continuation of application No. 11/303,813, filed on Dec. 16, 2005, now Pat. No. 7,799,769, which is a continuation of application No. 10/464,310, filed on Jun. 18, 2003, now abandoned.

(56) References Cited

U.S. PATENT DOCUMENTS

| | | |
|---|---|---|
| 2006/0100186 A1 | 5/2006 | White |
| 2009/0215852 A1 | 8/2009 | Bascomb |
| 2011/0118227 A1 | 5/2011 | White |

OTHER PUBLICATIONS

PCT Search Report related to Application No. PCT/US2011/061256, mailed Mar. 29, 2012.

Fibromyalgia Study, Preliminary Patient Questionnaire

Name: _____

Age: _____ Date of birth: _____ SS# _____
Address: _____

*If you are enrolled in this study, your address and social security number are required for us to pay you.*

Daytime Telephone Number: _____ Patient code: _____

| Yes | No | Please answer the following questions the best you can. |
|---|---|---|
| | | How tall are you? _____ How many pounds do you weigh? _____ |
| ☐ | ☐ | Have you been diagnosed with Fibromyalgia Syndrome? |
| ☐ | ☐ | Do you have widespread pain all over? (above/below waist, right/left sides) |
| ☐ | ☐ | Are you frequently fatigued? |
| ☐ | ☐ | Have you had your ovaries removed? |
| | | If yes, please give the date of your surgery _____ |
| ☐ | ☐ | Are you on hormone therapy? |
| | | If yes, what hormones: _____ |
| ☐ | ☐ | Are you willing to discontinue your hormone therapy for 6 months? |
| | | When was your last menstrual period? _____ |
| ☐ | ☐ | Do you have undiagnosed vaginal bleeding? |
| ☐ | ☐ | Do you smoke? If yes, how many cigarettes a day? _____ |
| ☐ | ☐ | Do you drink alcohol? If yes, how much a day, a week? _____ |
| ☐ | ☐ | Do you have high blood pressure, cardiovascular disease, liver or kidney disease, cancer, diabetes? Specify: _____ |
| ☐ | ☐ | Do you have any skin diseases? Specify: _____ |
| ☐ | ☐ | Do you take St. John's wort, ginger root, antidepressants? If yes, are you willing to stop taking them for 6 months? _____ |
| ☐ | ☐ | Are you willing to exercise 20 minutes a day, 5 days a week? |

Thank you for answering this questionnaire. You may explain any responses on the back.

FIG. 7

*Fibromyalgia Study: Testosterone Replacement Therapy vs Placebo*
*Physician Questionnaire Eligibility Criteria Form*

Eligibility Criteria

| Patient Code Number _____ |
| Patient Initials .......... _____ |
| Prelim TP Exam Date ____/____/____ |

Physician (initials): _____     A. Laboratory tests for eligibility criteria

|  | screen visit | day 1 | 12 weeks | 24 weeks |
|---|---|---|---|---|
| Date blood drawn (mm/dd/yy) | __/__/__ | __/__/__ | __/__/__ | __/__/__ |
| 1. Testosterone: _____ | | | | |
| 2. Estradiol: | _____ | | | |
| 3. Lipid Profile: | | | | |
| a. total cholesterol _____ | | | | |
| b. HDL _____ | | | | |
| c. LDL _____ | | | | |
| d. TG _____ | | | | |
| 4. Liver Function Tests (LFT): | | | | |
| a. ALT (Alanine aminotransferase) _____ | | | | |
| b. ALP (Alkaline phosphatase) _____ | | | | |
| c. AST (Asp aminotransferase) _____ | | | | |
| d. albumin _____ | | | | |
| e. TBil _____ | | | | |
| f. DBil _____ | | | | |
| 5. Kidney function: | | | | |
| a. BUN _____ | | | | |
| b. creatinine _____ | | | | |
| 6. FSH: _____ | | | | |
| 7. CBC Hemoglobin _____ | | | | |

B. Informed written consent obtained? Yes[ ] No[ ]

C. [ ] Does the patient express any symptoms of chronic fatigue?

D. [ ] Does the patient express difficulty obtaining restorative sleep?

FIG. 8

*Fibromyalgia Study: Testosterone Replacement Therapy vs Placebo*
*Dose Coordinator Serum Testosterone Values*

```
Patient Code Number ...  _____

Patient Initials  ..........  _____

Prelim TP Exam Date    __ / __ / __

Circle:   Placebo      Testosterone
```

Dose Coordinator (initials): _____

|  | 4 weeks | 8 weeks | 12 weeks | 16 weeks | 20 weeks | 24 weeks |
|---|---|---|---|---|---|---|
| Date blood drawn | __/__/__ | __/__/__ | __/__/__ | __/__/__ | __/__/__ | __/__/__ |

A. Total Testosterone: _____  _____  _____  _____  _____  _____

B. Free Testosterone: _____  _____  _____  _____  _____  _____

Based on Free Testosterone:

Step up 1 packet?   __/__/__   __/__/__   __/__/__   __/__/__   __/__/__   __/__/__
(if Low free T ≤ 1.9pg/mL, date patient started change in study gel dose)

Step down 1 packet?   __/__/__   __/__/__   __/__/__   __/__/__   __/__/__
__/__/__
(if High free T > 3.3pg/mL, date patient started change in study gel dose)

FIG. 9

*Fibromyalgia Study: Testosterone Replacement Therapy vs Placebo*
*Physician General Health Form*

| Patient Code Number _____ |
| Patient Initials ........... _____ |
| Exam Date ................. ___ / ___ / ___ |
| Circle one: |
| Screening Visit 2     Week 12 |
| Week 24 |

Physician (initials): _____

SKIN:

NECK:

LUNGS:

CARDIOVASCULAR:

ABDOMINAL:

EDEMA:

HEENT (Head Eyes Ears Nose Throat):

THYROID:

NEURO:

JOINTS:

OTHER:
(continue on reverse side of page if necessary)

FIG. 11

*FMS Study: Testosterone Replacement Therapy*
*Patient Questionnaire Form*

Section 1-4 needs to be filled out only once:   This box is to be filled out by your study coordinator/physician:

1. Date of Birth ......... ___/___/___

2. Age .....................

3. Height (feet/inches)_____

4. Ethnicity:

Patient Code Number.........

Patient Initials ................... _____

Interview Date ................ ___/___/___

Telephone Number:

☐ Non-Hispanic White   ☐ Other Non-Hispanic   ☐ Hispanic

5. Weight (lbs) ......... _____

6. Blood Pressure..... _____

7. General Health:

A. Have you had any phytoestrogens (soy) in the past month?  1.Yes ☐   2. No ☐

B. Approximately how many days on average per week in the past month have you eaten a grapefruit or had grapefruit juice? _____

C. Exercise:
(i) Do you exercise for at least 20 minutes 3 or more times a week?

1. ☐ Yes ............2. ☐ No .............

(a) If you exercise, what type of exercise do you do?

1. Lifting weights? ☐
2. Strengthening exercises (e.g. floor exercises)? ☐
3. Cardiovascular exercises (e.g. aerobics, brisk walking, X-country skiing?) ☐

(b) How many days per week on average? ....................._____

(c) How long does your exercise session last? _____ minutes (d) How long have you been exercising in this way? _____ months or _____ years D. Do you have any chronic medical problems other than FMS? 1.Yes ☐   2. No ☐

List each current problem/illness and approximate date of onset:

Illness 1. _____, Date of onset (MM/YY) ___ / __

Illness 2. _____, Date of onset (MM/YY) ___ / __

Illness 3. _____, Date of onset (MM/YY) ___ / __

E. Are you taking over-the-counter pain medication? .......... 1. ☐ Yes ..... 2. ☐ No
(E.g. Advil, Tylenol, aspirin)

FIG. 12A

(i) List each medication you take currently:

1. _____, # pills ____ (per ☐ day..... ☐ week)
2. _____, # pills ____ (per ☐ day..... ☐ week)
3. _____, # pills ____ (per ☐ day..... ☐ week)

(ii) Are you taking any medications, other than over-the-counter pain medication or hormone replacement therapy? (Include vitamins, supplements or herbal remedies.)

1. ☐ Yes ........ 2. ☐ No

List each medication you take currently:

1. _____
2. _____
3. _____
4. _____
5. _____
6. _____

8. FMS Symptoms over the last week:
Over the last week, what is the average level of each of the following symptoms on a scale of 0-10, with 0 being normal and 10 being severe:

A. Rate your muscle pain over the past month:

0 _____ 10
no muscle pain                                 incapacitating muscle pain B. How tired have you been?

0 _____ 10
no tiredness                                     very tired/bedridden C. How severe have your headaches been?

0 _____ 10
no headaches                                    severe headaches

How often do you have headaches?
1. Never ☐    2. Seldom ☐    3. Often or usually ☐    4. Always ☐

D. How bad has your stiffness been?

0 _____ 10
no stiffness                                      very stiff

FIG. 12B

E. Sleeplessness:

(i) How many hours of sleep do you think is optimal for you? ..... _____

(ii) How have you felt when you got up in the morning?

0  _____ 10
awoke well rested                          awoke very tired F. How tense, nervous or anxious have you felt?

0 _____ 10
not tense                                      very tense

G. How depressed or blue have you felt?

0 _____ 10
not depressed                              very depressed

H. Libido (sex drive, joy in life)

(i) What is your level of sex drive?

0 _____ 10
lowest level                                highest level (ii) What is your level of drive or joy in life?

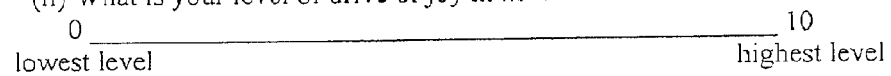
0 _____ 10
lowest level                                highest level

I. Have you had any other symptoms in the last week?

Please specify:_____

J. What percent of your activities prior to having FMS do you do? _____ %

K. Are you employed? ....1. ☐ Yes ..... 2. ☐ No .............# Hrs/week? _____

1. Of the 7 days in the past week, how many days did you feel good (circle)?

0  1  2  3  4  5  6  7

2. How many days in the past week did you miss work because of your fibromyalgia (circle)?
(If you don't have a job outside the home leave this item blank.)

1  2  3  4  5

3. When you did work, how much did pain or other symptoms of your fibromyalgia interfere with your ability to do your work (circle)?

0 _____ 10
no problem                                great difficulty

FIG. 12C

9. Gynecological History *(section 9 needs to be filled out only once at the beginning of the study)*:

A. Are you: ...1. ☐ Still menstruating? ..2. ☐ Postmenopausal (1 yr without your period)?

B. When was your last menstrual period (MM/DD/YY) ____/____/____

C. Are you on hormone replacement therapy? ......... 1. ☐ Yes ...... 2. ☐ No (a) If yes, what hormones are you currently taking? _____

_____

(b) Have you had any DHEA in the past month? 1. ☐ Yes 2. ☐ No

D. How many total pregnancies have you had? ............ ____

E. How many live births have you had? .................... ____

10. Please answer part 10 only if you are dropping out of this study:

A. If you decide to go off the study gel, are you willing to:

Continue to fill out our questionnaires? 1. ☐ Yes    2. ☐ No

Have your serum tested? 1. ☐ Yes    2. ☐ No

Have tender point exams? 1. ☐ Yes    2. ☐ No

Submit to movement tests? 1. ☐ Yes    2. ☐ No

B. If you are willing to tell us, we would be interested in why you decided to drop out of the study:

Your Health and Well-Being

This survey asks for your views about your health. This information will help keep track of how you feel and how well you are able to do your usual activities. *Thank you for completing this survey!*

For each of the following questions, please mark an ☒ in the one box that best describes your answer.

1. In general, would you say your health is:

| Excellent | Very good | Good | Fair | Poor |
|---|---|---|---|---|
| ▼ | ▼ | ▼ | ▼ | ▼ |
| ☐₁ | ☐₂ | ☐₃ | ☐₄ | ☐₅ |

2. Compared to one week ago, how would you rate your health in general now?

| Much better now than one week ago | Somewhat better now than one week ago | About the same as one week ago | Somewhat worse now than one week ago | Much worse now than one week ago |
|---|---|---|---|---|
| ▼ | ▼ | ▼ | ▼ | ▼ |
| ☐₁ | ☐₂ | ☐₃ | ☐₄ | ☐₅ |

FIG. 13A

3. The following questions are about activities you might do during a typical day. Does <u>your health now limit you</u> in these activities? If so, how much?

|  | Yes, limited a lot | Yes, limited a little | No, not limited at all |
|---|:---:|:---:|:---:|
| a <u>Vigorous activities</u>, such as running, lifting heavy objects, participating in strenuous sports | ☐₁ | ☐₂ | ☐₃ |
| b <u>Moderate activities</u>, such as moving a table, pushing a vacuum cleaner, bowling, or playing golf | ☐₁ | ☐₂ | ☐₃ |
| c Lifting or carrying groceries | ☐₁ | ☐₂ | ☐₃ |
| d Climbing <u>several</u> flights of stairs | ☐₁ | ☐₂ | ☐₃ |
| e Climbing <u>one</u> flight of stairs | ☐₁ | ☐₂ | ☐₃ |
| f Bending, kneeling, or stooping | ☐₁ | ☐₂ | ☐₃ |
| g Walking more than a mile | ☐₁ | ☐₂ | ☐₃ |
| h Walking several hundred yards | ☐₁ | ☐₂ | ☐₃ |
| i Walking <u>one hundred yards</u> | ☐₁ | ☐₂ | ☐₃ |
| j Bathing or dressing yourself | ☐₁ | ☐₂ | ☐₃ |

FIG. 13B

4. During the past week, how much of the time have you had any of the following problems with your work or other regular daily activities as a result of your physical health?

|   | All of the time | Most of the time | Some of the time | A little of the time | None of the time |
|---|---|---|---|---|---|
| a. Cut down on the amount of time you spent on work or other activities | ☐1 | ☐2 | ☐3 | ☐4 | ☐5 |
| b. Accomplished less than you would like | ☐1 | ☐2 | ☐3 | ☐4 | ☐5 |
| c. Were limited in the kind of work or other activities | ☐1 | ☐2 | ☐3 | ☐4 | ☐5 |
| d. Had difficulty performing the work or other activities (for example, it took extra effort) | ☐1 | ☐2 | ☐3 | ☐4 | ☐5 |

5. During the past week, how much of the time have you had any of the following problems with your work or other regular daily activities as a result of any emotional problems (such as feeling depressed or anxious)?

|   | All of the time | Most of the time | Some of the time | A little of the time | None of the time |
|---|---|---|---|---|---|
| a. Cut down on the amount of time you spent on work or other activities | ☐1 | ☐2 | ☐3 | ☐4 | ☐5 |
| b. Accomplished less than you would like | ☐1 | ☐2 | ☐3 | ☐4 | ☐5 |
| c. Did work or other activities less carefully than usual | ☐1 | ☐2 | ☐3 | ☐4 | ☐5 |

FIG. 13C

6. During the past week, to what extent has your physical health or emotional problems interfered with your normal social activities with family, friends, neighbors, or groups?
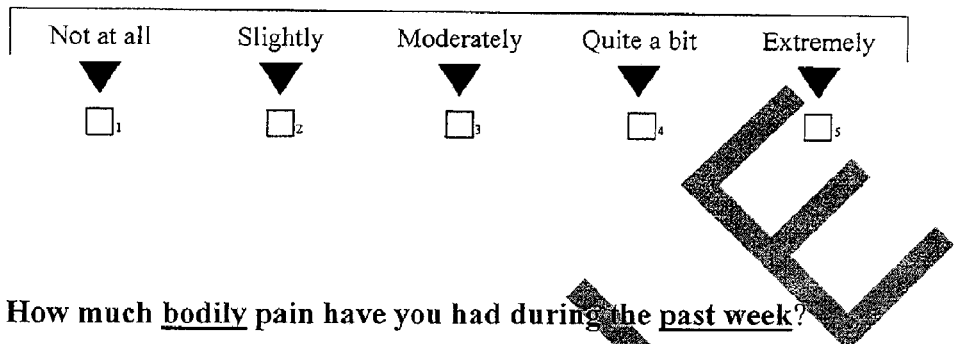
7. How much bodily pain have you had during the past week?
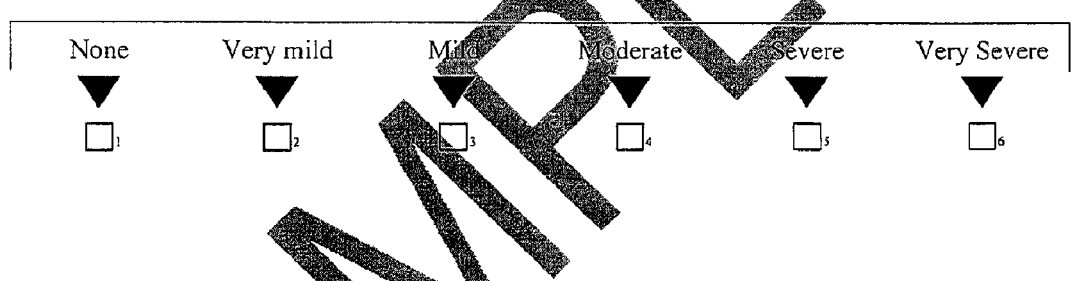
8. During the past week, how much did pain interfere with your normal work (including both work outside the home and housework)?
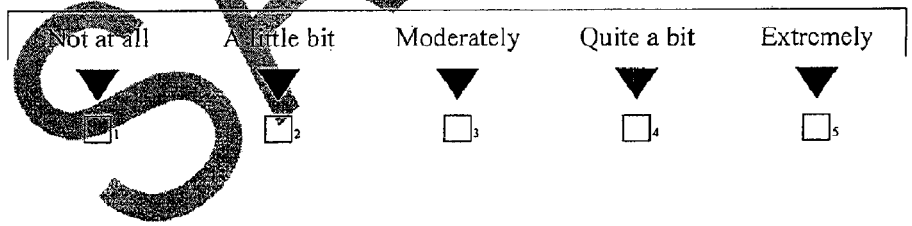
FIG. 13D 9. These questions are about how you feel and how things have been with you during the past week. For each question, please give the one answer that comes closest to the way you have been feeling. How much of the time during the past week...

|  | All of the time | Most of the time | Some of the time | A little of the time | None of the time |
|---|---|---|---|---|---|
| a. Did you feel full of life? | ☐₁ | ☐₂ | ☐₃ | ☐₄ | ☐₅ |
| b. Have you been very nervous? | ☐₁ | ☐₂ | ☐₃ | ☐₄ | ☐₅ |
| c. Have you felt so down in the dumps that nothing could cheer you up? | ☐₁ | ☐₂ | ☐₃ | ☐₄ | ☐₅ |
| d. Have you felt calm and peaceful? | ☐₁ | ☐₂ | ☐₃ | ☐₄ | ☐₅ |
| e. Did you have a lot of energy? | ☐₁ | ☐₂ | ☐₃ | ☐₄ | ☐₅ |
| f. Have you felt downhearted and depressed? | ☐₁ | ☐₂ | ☐₃ | ☐₄ | ☐₅ |
| g. Did you feel worn out? | ☐₁ | ☐₂ | ☐₃ | ☐₄ | ☐₅ |
| h. Have you been happy? | ☐₁ | ☐₂ | ☐₃ | ☐₄ | ☐₅ |
| i. Did you feel tired? | ☐₁ | ☐₂ | ☐₃ | ☐₄ | ☐₅ |

10. During the past week, how much of the time has your physical health or emotional problems interfered with your social activities (like visiting friends, relatives, etc.)?

| All of the time | Most of the time | Some of the time | A little of the time | None of the time |
|---|---|---|---|---|
| ☐₁ | ☐₂ | ☐₃ | ☐₄ | ☐₅ |

FIG. 13E

11. How TRUE or FALSE is each of the following statements for you?

|  | Definitely true | Mostly true | Don't know | Mostly false | Definitely false |
|---|---|---|---|---|---|
| a I seem to get sick a little easier than other people | ☐₁ | ☐₂ | ☐₃ | ☐₄ | ☐₅ |
| b I am as healthy as anybody I know | ☐₁ | ☐₂ | ☐₃ | ☐₄ | ☐₅ |
| c I expect my health to get worse | ☐₁ | ☐₂ | ☐₃ | ☐₄ | ☐₅ |
| d My health is excellent | ☐₁ | ☐₂ | ☐₃ | ☐₄ | ☐₅ |

*THANK YOU FOR COMPLETING THESE QUESTIONS!*

FIG. 13F

*Fibromyalgia Study: Testosterone Replacement Therapy vs Placebo*
*FMS Movement Test Form*

| Patient Code Number _____ |
| Patient Initials .......... _____ |
| Prelim TP Exam Date ___ _/___/ |

Administrator initials: _____ _____ _____ _____ _____ _____ _____
                Baseline  4 weeks  8 weeks  12 weeks  16 weeks  20 weeks  24 weeks Date of movement test: __/__/__ __/__/__ __/__/__ __/__/__ __/__/__ __/__/__ __/__/__

AR1. R Active flexion: _____ _____ _____ _____ _____ _____ _____
Shoulder-arm forward elevation, degrees
AR2. R Pain: _____ _____ _____ _____ _____ _____ _____
VAS (0 no pain–10 worst pain)

AL1. L Active flexion: _____ _____ _____ _____ _____ _____ _____
Shoulder-arm forward elevation, degrees
AL2. L Pain: _____ _____ _____ _____ _____ _____ _____
VAS (0 no pain–10 worst pain BR1. R Active abduction: _____ _____ _____ _____ _____ _____ _____
Shoulder-arm lateral elevation, degrees
BR2. R Pain: _____ _____ _____ _____ _____ _____ _____
VAS (0 no pain–10 worst pain)

BL1. L Active abduction: _____ _____ _____ _____ _____ _____ _____
Shoulder-arm lateral elevation, degrees
BL2. L Pain: _____ _____ _____ _____ _____ _____ _____
VAS (0 no pain–10 worst pain CR1. R Hand-to-neck: _____ _____ _____ _____ _____ _____ _____
Fingers reach the posterior median line of the neck front w/ the shoulder in full abduction and external rotation, 5 point range scale AR2. R Pain: _____ _____ _____ _____ _____ _____ _____
VAS (0 no pain–10 worst pain CL1. L Hand-to-neck: _____ _____ _____ _____ _____ _____ _____
Fingers reach the posterior median line of the neck front w/ the shoulder in full abduction and external rotation, 5 point range scale CL2. L Pain: _____ _____ _____ _____ _____ _____ _____
VAS (0 no pain–10 worst pain)

FIG. 14A

|  | baseline | 4 weeks | 8 weeks | 12 weeks | 16 weeks | 20 weeks | 24 weeks |
|---|---|---|---|---|---|---|---|
| Date of movement test: | / / | / / | / / | / / | / / | / / | / / |

DR1. R Hand-to-scapula: ___
Hand reaches behind trunk to the opposite scapula, 5 point range scale BR2. R Pain: ___
VAS (0 no pain–10 worst pain)

DL1. L Hand-to-scapula: ___
Hand reaches behind trunk to the opposite scapula, 5 point range scale DL2. L Pain: ___
VAS (0 no pain–10 worst pain)

ER1. R Shoulder endur: ___
Isometric, arm at 90o of abduction with 1kg weight cuff attached immediately proximal to caput ulna (wrist bone)
Rate of perceived exertion RPE via Borg's continuous 15 point scale ER2. R Pain: ___
VAS (0 no pain–10 worst pain)

EL1. L Shoulder endur: ___
Isometric, arm at 90o of abduction with 1kg weight cuff attached immediately proximal to caput ulna (wrist bone)
Rate of perceived exertion RPE via Borg's continuous 15 point scale EL2. L Pain: ___
VAS (0 no pain–10 worst pain)

F1. Chair test: ___
Number of sit/stands in one minute
F2. Pain: ___
VAS (0 no pain–10 worst pain in legs and/or low back)

FIG. 14B

Fibromyalgia Study
Patient Instructions for Use of Testosterone Gel

*There are _____ (number) clinical child-proof envelopes containing study gel in this kit. In each kit are also a blunt nose scissors and a patient daily evaluation log.*

1) Each morning, most preferably approximately 8:00 AM after a shower, the patient dries the upper abdominal area thoroughly with a towel. Do not scrub the application area too vigorously to induce reddening. The time of application and the date is recorded in the log.

2) One (1) envelope of study gel is removed.

3) The narrow end of the envelope that shows the taper is snipped off and the entire contents squeezed out onto the abdomen application site.

4) The gel is rubbed in until it disappears, as one would rub in a moisturizing cream. Do not apply gel directly where your waistband level is. 10 minutes after applying gel, wash hands.

5) The area is allowed to dry, about one to two minutes. Clothing may now be be applied and normal activities resumed.

6) The morning dose should not be missed. However, if an AM dose is missed, a dose may be applied any time during the day. If a daily dose is missed, do not apply two doses the following morning, but note that a dose was skipped.

7) Save all of the envelopes, used or unused, in the kit for return after study completion.

8) Fill out the study gel log carefully each day, noting the date, time of application, and evaluations or comments as instructed by the physician.

FIG. 15

| Fibromyalgia Study: Patient Log for Taking Study Gel (Example) ||||
|---|---|---|---|
| Week # ___ | *Date* | *Time* | *Comments* |
| Sunday | | | |
| Monday | | | |
| Tuesday | | | |
| Wednesday | | | |
| Thursday | | | |
| Friday | | | |
| Saturday | | | |

FIG. 16

Fibromyalgia Study, Patient Check List for Exercising (Example)

WEEK # ____

Please check off the days you have exercised:

| Indicate day of month: | Sun | Mon | Tues | Wed | Thurs | Fri | Sat |
|---|---|---|---|---|---|---|---|
| 10 min or more stretching | | | | | | | |
| 10 min or more aerobic | | | | | | | |

METHODS FOR THE TREATMENT OF FIBROMYALGIA AND CHRONIC FATIGUE SYNDROME

This application is a 35 U.S.C. 371 national phase application of International Application No. PCT/US2011/061256, filed Nov. 17, 2011, which is a continuation-in-part application under 35 U.S.C. §120 of U.S. patent application Ser. No. 12/949,644, filed Nov. 18, 2010, now U.S. Pat. No. 8,883,769, which is a continuation-in-part of U.S. patent application Ser. No. 12/837,310, filed Jul. 15, 2010, now U.S. Pat. No. 8,999,963, which is a continuation of U.S. patent application Ser. No. 11/303,813, filed Dec. 16, 2005, now U.S. Pat. No. 7,799,769 B2, which application is a continuation of U.S. patent application Ser. No. 10/464,310 filed Jun. 18, 2003, abandoned. Each of these applications is incorporated herein by reference in its entirety.

INTRODUCTION

The invention relates to the treatment of fibromyalgia and chronic fatigue syndrome by administration of an androgen composition. The treatment is effective for treating fibromyalgia-related pain and fatigue.

BACKGROUND OF THE INVENTION

The Women's Health Initiative (WHI) clinical trial, whose aim was to prospectively evaluate the risks and benefits of orally administered combination hormone replacement therapy in healthy women using estrogens and medroxyprogesterone acetate, was recently halted (Fletcher, S. W. et al. 2002. J. Amer. Med. Assoc. 288:366-368). The increased risks in coronary heart disease, breast cancer, stroke, and pulmonary embolism outweighed the increased benefits in colorectal cancer, endometrial cancer, hip fractures and death due to other causes, resulting in a small but statistically significant increased risk for the global index of hazard ratios among women taking these hormones. The authors pointed out, however, that their study only evaluated healthy women, not those with symptoms of hormone deficiency. Furthermore, other routes of delivery, e.g., transdermal systems, need to be studied, since it is possible that transdermal delivery may increase benefits and/or decrease risks to these patients. It was noted by the authors of the WHI study that hormone replacement therapy is still considered to be effective for relieving perimenopausal symptoms such as hot flashes.

Most clinical trials evaluating sex hormone replacement therapy have focused on estrogens and progestins, although testosterone replacement therapy in women who may be testosterone deficient is now beginning to be addressed using transdermal delivery systems, e.g., for disease states in which there is stress from chronic disease with loss of muscle mass and chronic fatigue, such as wasting syndrome in women with AIDS (Miller, K. et al., 1998. J. Clin. Endocrinol. Metab. 83:2717-2725; Javanbakht, M. et al., 2000. J. Clin. Endocrinol. Metab. 85:2395-2401). Testosterone replacement therapy using transdermal delivery has also been of benefit to men with symptoms of testosterone deficiency, for example in men with Parkinson's disease (Okun, M. S. et al., 2002. Arch. Neurol. 59:1750-1753). There is accumulating evidence that the sex hormones, in particular estrogens, progestins and now testosterone, are important for subjective feelings of well-being and quality of life, parameters that were not assessed in the Women's Health Initiative trial.

U.S. Pat. No. 5,935,949 discloses a method of alleviating the symptoms of fibromyalgia syndrome and chronic fatigue syndrome which involves oral administration of androgens, such as testosterone, to patients. The idea behind the use of testosterone therapy in the treatment of such conditions is that muscle pain and chronic fatigue, primary symptoms in women with fibromyalgia syndrome (FMS), relates, at least in part, to testosterone deficiency, since androgens are known to allow for increased musculature and improvement in fatigue. Indeed, a small decrease in serum free testosterone concentrations has been documented for premenopausal fibromyalgia patients relative to healthy volunteers, but significance was not achieved for postmenopausal women (Dessein, P. H. et al., 1999. Pain 83:313-319). A relationship between testosterone and pain sensation has been previously suggested (Blomqvist, A. 2000. Compar. Neurol. 423:549-551). Accumulating evidence supports the concept that sex hormones can elevate the pain threshold in an individual, for example, during pregnancy (Gintzler, A. R. 1980. Science 210:193-195), when testosterone concentrations, as well as estrogen and progesterone concentrations, are elevated (Bammann, B. L. et al., 1980. Am. J. Obstet. Gynecol. 137:293-298). The theory that testosterone can suppress pain is supported by the discovery of aromatase-positive cells in the spinal cord dorsal horn of higher vertebrates (quail), where initial processing of pain sensation occurs (Evrard, H. et al., 2000. J. Compar. Neurol. 423:552-564). The presence of aromatase, which converts testosterone to 17.beta.-estradiol, is interesting because it is known that estrogen can induce the transcription of opiates in estrogen receptor-positive cells derived from the superficial layers of the spinal dorsal horn (Amandusson, A. et al., 1996. Neurosci. Lett. 196:25-28; Amandusson, A. et al., 1996. Eur. J. Neurosci. 8:2440-2445; Amandusson, A. et al., 1999. Pain 83:243-248), a location that is important for the synthesis of endogenous opiates. Administration of estrogen to ovariectomized female rats has been demonstrated to increase spinal cord enkephalin transcription (Amandusson, A. et al. 1999. Pain 83:243-248), and estrogen receptor-positive cells co-localize with preproenkephalin mRNA (Amandusson, A. et al., 1996. Eur. J. Neurosci. 8:2440-2445). These endogenous opiates act on enkephalinergic neurons to mediate inhibition of nociceptive relay cells, both in primary afferent fibers as well as in pain-modulating fibers descending from the brainstem (Ma, W. et al., 1997. Neuroscience 77:793-811). Thus, both testosterone and estrogen appear to be important for modulating the sensation of fibromyalgia-related pain. However, the differential importance of androgens versus estrogens in pain sensation relative to gender remains poorly understood.

Testosterone may also act at the level of the brain. Testosterone concentrations were dramatically decreased in the brain and spinal cord of rats in response to pain-inducing subcutaneous injections of formalin into the paw. In these animals, the loss of testosterone in the central nervous system was demonstrated to be due to its metabolism by 5.alpha.-reductase to dihydrotestosterone (Amini, H. et al., 2002. Pharmacol. Biochem. Behav. 74:199-204). These authors pointed out that dihydrotestosterone can be metabolized to 5.alpha.-androstane-3α,17β.-diol, which is an effective modulator of $GABA_A$ receptor complexes in the brain. $GABA_A$ receptors are found throughout the brain, and actions of $GABA_A$ receptor modulators in the limbic system, specifically in the amygdala, are associated with feelings of fear. The $GABA_A$ receptor ion channel complex is one of the most important inhibitory ion channels in the brain. Thus, testosterone may be important not only for modulation of fibromyalgia-related pain but also for feelings of emotional well-being via binding of its metabolites to the neurosteroid site of the $GABA_A$ receptor, although this remains to be demonstrated.

Other hormones such as growth hormone may also play a role in the pathogenesis and symptoms of fibromyalgia and chronic fatigue. For example, studies have shown that fibromyalgia patients fail to exhibit a proper growth hormone response to acute exercise, a response that is likely related to increased levels of somatostatin a powerful inhibitor of growth hormone synthesis (Crofford, L. J. et al., 2002. Arthr. Rheumat. 46:1136-1138; Paiva, E. S. et al., 2002. Arthr. Rheumat. 46:1344-1350). It is well known that testosterone increases growth hormone secretion. Growth hormone secretion is reduced in senescence beyond the reduced levels of secretion seen in adult life after puberty. This reduction is thought to relate to the decreased lean body mass to adipose mass ratio known to occur in some individuals in senescence. Thus, increased somatostatin levels may reflect decreased anabolism and decreased muscle mass due to decreased testosterone and growth hormone concentrations in fibromyalgia patients. As a result, therapy with growth hormone may improve the condition of patients with fibromyalgia.

It has now been found that transdermal hormone therapy in women can safely and effectively raise serum hormone concentrations to levels that approximate those normally found in premenopausal women, as well as relieve symptoms in patients with fibromyalgia.

SUMMARY OF THE INVENTION

An object of the present invention is a composition for increasing androgen levels in blood which comprises an androgen at a concentration of about one percent and a pharmaceutically acceptable gel. The androgen compounds of the instant invention may comprise testosterone and its derivatives.

Another object of the present invention is a method of alleviating the symptoms of fibromyalgia syndrome and chronic fatigue syndrome which comprises administering to a patient suffering from fibromyalgia syndrome or chronic fatigue syndrome an effective amount of the androgen gel formulation so that the symptoms are alleviated.

The invention relates to a method of alleviating the symptoms of a condition which is associated with deficient serum androgen levels in a female human patient comprising transdermally administering daily to said patient suffering from deficient serum androgen levels a safe and effective amount of an androgen which is both effective for alleviating the female patient's condition associated with androgen deficiency and for consistently raising the female patient's serum androgen levels to the middle-upper female reference range female reference range, wherein the composition contains a daily unit dose of an androgen and is formulated to provide steady state total androgen serum levels without raising free androgen serum levels or twenty-four hour free androgen AUC above the levels required for both therapeutic efficacy and safety.

The invention also relates to a method of determining the appropriate androgen dosage for a female human subject comprising diagnosing the female human subject as having fibromyalgia or chronic fatigue syndrome accompanied by a free androgen level in the lower half of the appropriate reference range; starting transdermal androgen treatment of the subject based on a diagnosis of fibromyalgia or chronic fatigue syndrome. After a predetermined time of treatment the free androgen level in the subject's blood is measured. If the subject's free androgen level remains in the lower half of the appropriate reference range, the androgen dosage is increased; if the subject's free androgen level is within the middle-to-upper end of the appropriate range, the androgen dosage is maintained; or if the subject's free androgen level is in excess of at least about 15% of the appropriate reference range, the androgen dosage is decreased. The predetermined treatment time can be 30 days, 60 days, 4 weeks, 8 weeks or any other time desired by a physician treating the subject. The method can be repeated several time over the course of treatment

DESCRIPTION OF THE DRAWINGS

FIG. 1A shows the day 1 profile, FIG. 1B shows the day 28 profile, and FIG. 1C shows the means±SEM for day 1 (open symbols) versus day 28 (filled symbols).

FIG. 2A shows the day 1 profile. FIG. 2B shows the day 28 profile. FIG. 2C shows the means±SEM for day 1 (open symbols) versus day 28 (filled symbols), with a change in the y-axis scale.

FIG. 7 is an example of a Fibromyalgia Study Preliminary Patient Questionnaire.

FIG. 8 is an example of a Physician Questionnaire Eligibility Criteria Form.

FIG. 9 is an example of a Dose (or Study) Coordinator Serum Testosterone Values Form.

FIG. 11 is an example of a Physician General Health Form.

FIGS. 12A-12D show an example of a Patient Questionnaire Form.

FIGS. 13A-13F show an example of a Global Health Form.

FIGS. 14A-14B show an example of a Fibromyalgia Movement Test Form.

FIG. 15 is an example of Patient Instructions.

FIG. 16 is an example of a Patient Log for Taking Study Gel.

FIG. 17 is an example of a Patient Checklist for Exercising.

FIG. 18 is an example of an Adverse Experience Report.

DETAILED DESCRIPTION OF THE INVENTION

Figure 1A:
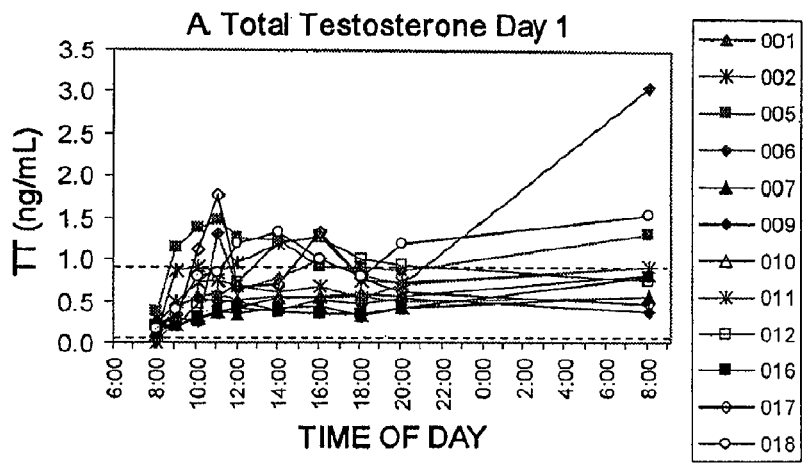
FIGS. 1A-1C depict the levels of total testosterone in blood of the patients.

The syndrome of chronic fatigue has received much attention lately. No physical finding or laboratory test can be used to confirm diagnosis of chronic fatigue syndrome. However, this syndrome is generally characterized by fatigue persisting or relapsing for more than six months occurring concurrently with at least four or more of the following symptoms: impaired memory or concentration, sore throat, tender cervical or axillary lymph nodes, fibromyalgia-related muscle pain, fibromyalgia-related multi-joint pain, new headaches, unrefreshing sleep, and post exertion malaise. Early studies suggested an infectious or immune dysregulation mechanism for the pathophysiology of chronic fatigue syndrome. More recent studies have shown that neurologic, affective and cognitive symptoms also frequently occur.

Fibromyalgia (also referred to as fibrositis) is one of the most common rheumatic syndromes in ambulatory general medicine affecting 3-10% of the general population. Most patients with Fibromyalgia Syndrome (FMS) are women, and of these patients, approximately 50-75% are women in their peri-postmenopausal years, aged 40-60. Approximately 2-5% of peri/post menopausal women are affected by FMS, with some estimates ranging from 0.5 to 20%. This disease is characterized by chronic widespread fibromyalgia-related musculoskeletal pain syndrome with multiple tender points, fatigue, headaches, lack of restorative sleep and numbness. Fibromyalgia shares many features with chronic fatigue syndrome including an increased frequency in peri/post menopausal woman, absence of objective findings and absence of diagnostic laboratory tests. Further, these conditions have overlapping clinical features including chronic fatigue, headaches and lack of restorative sleep with musculoskeletal fibromyalgia-related predominating in fibromyalgia and apparent increased susceptibility or hyperimmunologic responsiveness to infection predominating in chronic fatigue syndrome.

Various treatments for chronic fatigue syndrome including acyclovir, oral and vaginal nystatin and fluoxetine have been tried with little success. Placebo-controlled trials have demonstrated modest efficacy of amitriptyline, fluoxetine, chlorpromazine, or cyclobenzaprine in treating fibromyalgia. Exercise programs have also been suggested as beneficial in both conditions. Accordingly, there is clearly a need for better treatments for these debilitating conditions.

It has now been found that transdermal administration of hormones, including androgens, can alleviate symptoms in patients suffering from FMS or CFS. By "androgen therapy" it is meant to include administration of a single androgen or a combination of androgens. By "alleviate" it is meant to make less hard to bear, reduce or decrease, or lighten or relieve patients of the symptoms of FMS of CFS. By "symptoms" of FMS or CFS it is meant to include fibromyalgia-related muscle pain and atrophy, chronic fatigue, lack of restorative sleep, increased susceptibility to infection and headaches resulting from FMS or CFS.

The invention relates to a method of alleviating the symptoms of a condition which is associated with deficient serum androgen levels in a female human patient comprising transdermally administering daily to said patient suffering from deficient serum androgen levels a safe and effective amount of an androgen which is both effective for alleviating the female patient's condition associated with androgen deficiency and for consistently raising the female patient's serum androgen levels to the middle-to-upper range of the female reference range, wherein the composition contains a daily unit dose of an androgen and is formulated to provide steady state total androgen serum levels without raising free androgen serum levels or twenty-four hour free androgen AUC above the levels required for both therapeutic efficacy and safety.

The invention also relates to a method of determining the appropriate androgen dosage for a female human subject comprising diagnosing the female human subject as having fibromyalgia or chronic fatigue syndrome accompanied by a free androgen level in the lower half of the appropriate reference range; starting transdermal androgen treatment of the subject based on a diagnosis of fibromyalgia or chronic fatigue syndrome. After a predetermined time of treatment, for example 15-30 days, the free androgen level in the subject's blood is measured. If the subject's free androgen level remains in the lower half of the appropriate reference range, the androgen dosage is increased; if the subject's free androgen level is within the middle-to-upper end of the appropriate range, the androgen dosage is maintained; or if the subject's free androgen level is in excess of the standard error of the mean above appropriate reference range, the androgen dosage is decreased. The predetermined treatment time can be from 1-6 weeks, determined by a physician treating the subject. The predetermined time can be 30 days, 40 days, 4 weeks, or any time frame determined by the physician. The method can be repeated several times over the course of treatment, so that the appropriate dose of the androgen can be adjusted to avoid side effects.

Most trials involving hormone replacement therapy have used derivatives of hormones naturally found in women. These derivatized hormones have been promoted because of their patentability and their extended half life. Androgens are no exception since the androgen hormone most prescribed for women is methyltestosterone, where methylation at the C-17 position increases its oral bioavailability. Patients do not tolerate these derivatized hormones very well, however. Non-derivatized exogenous hormones that are structurally identical to endogenous hormones have short plasma/serum half lives that range from 10-100 minutes, making oral administration of native hormones problematic. Investigators have begun to develop transdermal delivery systems, which provide sustained delivery while minimizing hepatotoxicity. A testosterone skin patch has been effective in HIV seropositive women with wasting syndrome (Miller, K. et al., 1998. J. Clin. Endocrinol. Metab. 83:2717-2725; Javanbakht, M. et al., 2000. J. Clin. Endocrinol. Metab. 85:2395-2401), but the skin patch causes topical skin irritation in many women, making its use problematic.

The present invention involves use of a testosterone formulated as a gel in a concentration that is appropriate for women. The data have shown this formulation to provide effective systemic delivery of testosterone in patients with fibromyalgia. 28 days of therapy with 0.75 g 1% (w/w) testosterone gel per day raised serum concentrations of total and free testosterone in fibromyalgia patients to concentrations approximating those in premenopausal women. At this dose, patients showed significantly decreased fibromyalgia-related muscle pain, decreased stiffness, decreased fatigue and increased libido in response to testosterone therapy. Fibromyalgia-related tender point pain was decreased, as well. These results, from both the pharmacokinetic and fibromyalgia-related pain assessment standpoints, support the use of testosterone replacement therapy to treat individuals with fibromyalgia syndrome.

Accordingly, androgen therapy provides a useful means for alleviating symptoms associated with FMS or CFS in women preferably of peri/post menopausal age. By peri/postmenopausal age it is most often meant to be approximately 40 to 60 years of age. Women outside of this range may also benefit since these syndromes have been known to be present in women 20 to 60 years of age. In a preferred embodiment, the androgen administered comprises testosterone, an active metabolite of testosterone such as dihydrotestosterone or androstenedione or a testosterone derivative such as methyltestosterone, testosterone enanthate or testosterone cypionate. Examples of available pharmacologic preparations of androgens believed to be useful in this invention include, but are not limited to danazol, fluoxymesterone, oxandrolone, methyltestosterone, nandrolone decanoate, nandrolone phenpropionate, oxymethalone, stanozolol, methandrostenolone, testolactone, pregnenolone and dehydroepiandrosterone (DHEA).

In the present invention, the androgens are administered transdermally in a gel formulation. This formulation has advantages over current oral methods as well as transdermal patch methods that include improved bioavailability and a low side effect profile. In a preferred embodiment, a combination of androgens such as testosterone or a testosterone derivative and DHEA can be administered to alleviate both the muscular and neurological symptoms of FMS or CFS.

As will be obvious to those of skill in the art upon this disclosure, other pharmaceutically acceptable androgen therapies can be considered. However, effective amounts and routes by which the androgen or combination of androgens can be administered amount to a significant challenge based on the number of failures in this field. Finding the right amount, formulation, and route for human use and then proving the safety and efficacy of the formulation has been a major challenge for those skilled in the art based on their experience with androgen therapies.

Generally, the androgen used in the invention is a biologically active androgen. Androgens may be active in their native state, and/or may be a precursor or pro-drug that is metabolized to a active state upon delivery to the subject. The androgen may be, but is not limited to, testosterone, androstenedione, androstendiol, dehydroepiandrosterone, danazol, fluoxymesterone, oxandrolone, nandrolone decanoate, nandrolone phenpropionate, oxymethalone, stanozolol, methandrostenolone, testolactone, pregnenolone, dihydrotestosterone, methyltestosterone, androgen precursors, or testosterone esters.

Administration of an androgen that achieves blood levels outside the reference range can result in adverse effects. Females are especially susceptible because their normal blood levels are one tenth those of males. Levels in excess of the upper limit of the reference range+/−SEM can cause, for example, hirsutism, acne, rapid (and sometimes permanent) changes in voice, emotional changes, and the more serious side effects of heart disease, cancer, and liver disease. Examples of these changes and side effects are discussed below.

It is desirable to maintain a patient's androgen blood levels within the middle to upper portion of the appropriate reference range. If androgens are administered in excess, clinical symptoms of androgen excess can appear. These symptoms can range from upsetting to dangerous. Generally, the symptoms of androgen excess include, but are not limited to, excessive and abnormal hirsutism, increased moodiness, anger, adverse lipid changes, abnormal liver function, weight gain, acne, alteration of libido, edema, functional and structural liver damage, cancer, permanent changes in voice, emotional changes, and diabetes.

For assessing safety, female patients will be dosed adjusted such that the "upper limit of the reference range for free testosterone" is defined as less than or equal to "about" 3.3 pg/mL when using the DSL free testosterone blood level assay (Table 1); and less than or equal to "about" 19 pg/mL when using the Mayo Medical Labs free testosterone blood level assay. If using another test with its own reference range, a person of skill would assess safety blood level limits in a equivalent way.

High testosterone levels above the reference range have been shown to result in the harmful effects of testosterone. Females with virilizing ovarian tumors provide a good example. Regnier et al., (2002 J. Clin. Endocrinol. Metab. 87(7): 3074) disclose a case study of a woman having a virilizing ovarian tumor (one that secretes testosterone and results in hyperandrogenism in about 80% of cases), with hirsutism that got progressively worse over time. Her total testosterone level was between 3.9 ng/mL and 7.0 ng/mL, which is above the reference range for females. Once the tumor was removed, her testosterone level returned to normal, the hirsutism subsided, and the hyperandrogenism did not recur.

It has also been shown that women with certain conditions, including breast cancer, have a total testosterone level higher than the reference range for women. For example, it has been shown that post-menopausal breast cancer patients can have a total testosterone level of about 1.55 ng/mL, which is above the reference range. Women with testosterone levels of over 1.55 ng/mL have a four-fold greater chance of developing breast cancer. (Ho et al., 2009 Singapore Med. J. 50(5):513).

Further, female-to-male (FTM) transsexuals, who are dosed with testosterone such that their blood levels reach male levels, i.e., >300 ng/dL (>3 ng/mL) have been studied for the safety of these levels in these genotypic females. Jacobeit (2009 Eur. J. Endocrinol. 161: 795) discloses dosing females to achieve stable serum testosterone levels within the eugonadal male reference range of about 620+/−130 ng/dL (6.2+/−1.3 ng/mL) for 36 months. Gooren et al., (2008 J. Sexual Med. 5: 765) teaches that the female-to-male transsexuals receiving doses of testosterone at or above the male reference range develop hirsutism and male-like increased risk for cardiovascular disease and diabetes. Bachmann et al. (2002 Fertil. Steril. 77(4): 660) teach that testosterone and other androgens have many detrimental side effects. Specifically, testosterone can cause acne, weight gain, excess hair, increased anger, adverse lipid changes, and abnormal liver function. Franke et al. (1997 Clin. Chem. 43(7): 1262) disclose that over-administration of anabolic steroids can cause many health problems, including weight gain, acne, hirsutism, alteration of libido, edema, function and structural liver damage. Finally, testosterone and other androgens are Schedule C-III controlled substances under the Anabolic Steroid Control Act and, as such, can be dangerous to over-administer in view of the dangerous side-effects of cancer, liver disease, and cardiac disease.

All of the above studies show the challenge to treating both women and men with testosterone or other androgens. It is of great importance to make sure that the dosage administered to women and men brings the androgen level to the proper and appropriate range, or the equivalent safe and effective range based on the detection assay used (see Table 1).

By "safe," it is meant that blood levels are not raised significantly above the upper end of the reference range. By "effective," it is meant that androgen therapy raises baseline blood levels from the lower half of the reference range to significantly higher blood levels that are still safe within the reference range. The therapy can raise the androgen blood levels from the baseline level to the middle or upper levels of the female reference range. While total testosterone is a factor when considering the blood levels of testosterone, it is the free testosterone that is an indicator of the testosterone that is available for biologic action in vivo. Further, free and bioavailable testosterone generally remain in a constant ratio and are reliable indicators of biologic availability, while SHBG-bound testosterone, which is not bioavailable, varies in response to changes in the total pool (Felig, P. and L. A. Frohman "Endocrinology and Metabolism" McGraw Hill, 4th edition, 2001 p 647).

The reference ranges for women and men differ by about ten times. Table 1 below, which shows the reference ranges for both women and men, and measured by two different detection means (male reference ranges only shown using one testing method). For example, the Diagnostic Systems Laboratories (DSL) reference range for women is about 0.1 ng/mL to about 1.0 ng/mL. The reference range determined using the Mayo Medical Laboratories diagnostic test is from about 0.08 ng/mL to about 0.6 mg/mL. The reference range for men, as calculated using the Mayo Medical Laboratories diagnostic test is about 2.4 ng/mL to about 9.5 ng/mL. It is important to remember that, when comparing serum testosterone reference ranges, one must translate the reference range from one test to another. One of skill in the art would know that diagnostic tests vary in their reference ranges, according to which, and whether, monoclonal antibody (mAb) was used for detection (earlier detection systems such as DSL use a detection mAb), or whether no mAb was used for detection (more recently developed detection systems such as Mayo Medical Labs, which use tandem mass spectrometry for inspection instead). Thus, the upper end of a safe total testosterone blood level range would be at about 1.0 ng/dL when using the DSL test, versus about 0.6 ng/dL when using the Mayo Medical Labs test. The upper end of a safe free testosterone range would be at about 3.3 pg/mL when using the DSL test, versus about 19 pg/mL when using the Mayo Medical Labs test. Furthermore, the reference range is only an approximation of what would be the "normal" range in individuals, since the reference range would be skewed downward if the "control" population included significant data from subjects with a deficiency.

TABLE 1

Testosterone serum reference ranges

|  | DSL ref range[1] | Mayo ref range[1] |
|---|---|---|
| Female TT[2] (age 40-60 yr) | 0.1-1.0 ng/mL (10-100 ng/dL) (100-1000 pg/mL) | 0.08-0.6 ng/mL (8-60 ng/dL) (80-600 pg/mL) |
| Female BioT (age 20-50 yr) (age >50 yr unkn) | Not determined. | 0.008-0.100 ng/mL (0.8-10 ng/dL) (8-100 pg/mL) |
| Female FT[2] (pre-menopausal) | 0.0003-0.0033 ng/mL (0.03-0.33 ng/dL) (0.3-3.3 pg/mL) | 0.003-0.019 ng/mL (0.3-1.9 ng/dL) (3-19 pg/mL) |
| % of TT that is BioT |  | 10-17% of TT is BioT |
| % of TT that is FT |  | 3-4% of TT is FT |
| % of BioT that is FT |  | 19-38% of BioT is FT |
| Male TT[2] (age >18 yr) |  | 2.4-9.5 ng/mL (240-950 ng/dL) (2,400-9,500 pg/mL) |

TABLE 1-continued

Testosterone serum reference ranges

|  | DSL ref range[1] | Mayo ref range[1] |
|---|---|---|
| Male BioT (age 40-49) |  | 0.61-2.13 ng/mL (61-213 ng/dL) (610-2,130 pg/mL) |
| Male % of TT that is FT |  | 2.0-4.8% of TT is FT [~22% of TT is BioT] |
| Male FT |  | 0.09-0.3 ng/mL (9-30 ng/dL) (90-300 pg/mL) |

Abbreviations:
TT = total testosterone (free testosterone + testosterone weakly bound to albumin + testosterone tightly bound to sex hormone binding globulin SHBG);
FT = free testosterone (unbound)
BioT = bioavailable (or bioactive) testosterone (free testosterone + testosterone weakly bound to albumin)
[1]Because reference ranges vary according to the antibody used in the test, the source of reference ranges used for the values in this table is indicated: DSL (Diagnostic Systems Laboratories); Mayo (Mayo Medical Laboratories), a common testing service in hospitals for testing TT, FT and BioT (analysis by tandem mass spec after AmSO4 precipitation). Claims based on the reference range from an antibody detection test such as DSL must be converted to the Mayo Medical Labs reference range, which does not rely on antibody detection of testosterone, in order to make comparisons. The above table can be used for this purpose.
[2]Male testosterone levels are generally on the order of 10x female testosterone levels; Free testosterone is on the order of 1-5% of total testosterone.

In one embodiment of the invention, and for both the method of treating fibromyalgia-related pain in a female human, the androgen can be transdermally administered in a daily unit dose of about 0.1 mg to about 12.8 mg of the androgen in a pharmaceutically acceptable carrier formulated for daily topical administration as a gel and wherein the gel is formulated to deliver steady state total androgen serum levels without raising free androgen serum levels or twenty-four hour free androgen AUC above the levels required for therapeutic efficacy and safety. Preferably, the daily unit dose of the androgen is from about 1.0 mg to about 12.8 mg. More preferably, the daily unit dose of the androgen is from about 2.5.0 mg to about 10.0 mg. More preferably, the daily unit dose of the androgen is from about 3.2 mg to about 9.6 mg. Even more preferably, the daily unit dose can be from about 4.4 mg to about 9.6 mg. Most preferably from about wherein the daily unit dose of the androgen is from about 6.0 mg to about 8.0 mg. The daily unit dose of the androgen can be about 6.5 mg or about 7.5 mg.

In another embodiment, the dosing range can be incremental. For example, the dose to be administered to a female subject can be about 2.5 mg; 5.0 mg; 7.5 mg; or 10.0 mg. In order to determine the most appropriate dosage for a particular subject, a physician may start the patient on a low dose, and titrate the dose upwards until an dose that is both effective and safe is reached. In yet another embodiment, the incremental dosage rate can start at 3.2 mg, and rise progressively to 6.4 mg, 9.6 mg, and 12.8 mg, using a 0.8% gel formulation. For example, patients can be started with 2 packets of 0.8% testosterone or placebo gel per day for the first four weeks. Each packet can contain 400 mg of 0.8% testosterone gel (3.2 mg testosterone, to deliver 10% or 320 μg bioavailable testosterone) or 400 mg Placebo gel in it. After four weeks, any patient who tests>3.3 pg/mL for serum free testosterone (testosterone blood levels above the reference range), can decrease the dose by one gel packet/day. Any patient who tests≤0.9 pg/mL for serum free testosterone (at the low end of the testosterone reference range) can increase dose by one gel packet/day until the blood level is raised to near the mid-range or near the upper end of the reference range.

The daily unit dose can be delivered via a transdermal gel having about 0.1% to about 10.0% of the androgen. Preferably, the transdermal gel can have about 0.5% to about 5.0% of the androgen. More preferably, the transdermal gel can have about 0.5% to about 2.5% of the androgen. Most preferably, the transdermal gel can have about 0.8-1.0% of the androgen.

In another embodiment of the invention, and for treating fibromyalgia-related pain in a female human subject, the daily unit dose of the androgen may be selected to maintain steady state total androgen serum levels within a range of between about 0.7 ng/mL and about 1.6 ng/mL, and preferably between about 0.9 ng/mL and about 1.4 ng/mL for at least 24 hours after administration without raising free androgen serum levels or twenty-four hour free androgen AUC above the levels required for therapeutic efficacy and safety. Further, the free androgen serum levels and twenty-four hour free androgen AUC should not be raised above levels required for therapeutic efficacy and safety.

Specifically, the free androgen serum levels can be raised to between about 1.0 pg/mL and about 3.5 pg/mL. (About 3.3 pg/mL using the DSL test is equivalent to about 19 pg/mL using the Mayo Medical Labs mass spectrophotmetry method of measuring free testosterone, Table 1. The upper end of the reference range is determined by which method of measuring free testosterone is used). The twenty-four hour free androgen AUC levels can be raised to between about 35.18 pg-h/mL and about 72.60 pg-h/mL; more preferably the free androgen serum levels can be raised to between about 2.00 pg/mL and about 3.3 pg/mL and the twenty-four hour free androgen AUC levels can be raised to between about 40 pg-h/mL and about 65 pg-h/mL The daily unit dose of the androgen can be from about 4.0 mg to about 10.0 mg, or from about 6.0 mg to about 8.0 mg. At 10% bioavailability for the androgen in the gel that is actually delivered to the blood, the daily unit dose-to-be-delivered of the androgen can be from about 0.4 mg to about 1.0 mg, or from about 0.6 mg to about 0.8 mg androgen.

The formulation can be prepared using a variety of pharmaceutically acceptable ingredients. For transdermal administration, the formulation can include, but is not limited to, the androgen, a penetration enhancer, an emulsifier, a gelling agent; a lubricant, a thickening agent, a buffer, an alcohol, and water. As will be evident to those of skill in the art upon this disclosure, other pharmaceutically acceptable androgen therapies can be used. Effective amounts and routes by which the androgen or combination of androgens can be administered in a safe and effective manner according to the present invention can also be used, such that safe and effective blood levels of androgen are obtained. The formulation will preferably be used at a unit dose of 800 mg gel of 0.8% testosterone (6.4 mg testosterone), and then, depending on blood levels at 4 weeks, adjusting down to 400 mg gel of 0.8% testosterone (3.2 mg testosterone), or adjusting up to 1200 mg gel of 0.8% testosterone (9.6 mg testosterone), to maintain the unit dose to achieve safe and effective blood levels. Administration of the composition of the invention results in a low side-effect profile and delivers a therapeutically effective daily amount of the androgen to the patient's serum over each 24 hour period to alleviate the patient's symptoms without causing androgenic side effects.

The composition of the present invention comprises, in addition to the aforementioned androgen/anabolic agent, co-treatment with a pharmaceutically effective amount of growth hormone elicitor or effector, either growth hormone or an agent that is known to release growth hormone in effective amounts, i.e., a growth hormone releasing agent ("GRF"). GRF is an acronym based on the existence of an endogenous hormone known as GHRH. Other agents include GHrelin or a growth hormone releasing peptide or analog (GHRP; GHRP-6, or hexarelin, His-DTrp-Ala-Trp-DPhe-Lys, and GHRP-2, or Dala-D-2-NaI-Ala-Trp-Dphe-Lys are examples), which have been shown to release effective amounts of growth hormone. The natural rhythm of growth hormone release from the pituitary gland results in release of insulin-like growth factor (IGF-1), which in general, is considered to be the causal agent that determines the course of hormonal regulation and balance in processes such as adipogenesis and myogenesis. The hormonal effector, then, for the purpose of this invention, is also prophetically considered to be any peptide or peptidomimetic agent that directly acts to release this secondary anabolic growth factor, (IGF-1), not necessarily through the intermediary route of secretion of growth hormone itself. Although the indirect growth hormone route is preferred to elicit IGF-1, the latter route to directly release IGF-1 also is included by example.

In another embodiment of the present invention, the composition comprises a pharmaceutically effective amount of a growth hormone or, more preferably, a growth hormone-releasing agent, or an elicitor of IGF-1 secretion, coupled with androgen treatment and such combined treatment being capable of counteracting the deleterious effects of aging, such as, for example, muscle weakness, body fat increases, and skin fragility in adults. Essentially any suitable growth hormone-releasing agent may be employed in combination with any androgen, preferably one such as testosterone that possesses strong anabolic activity. Other anabolic agents that are not thought of as androgenic agents, or do not possess maximal androgenic activity may be used, as long as they have appreciable anabolic activity. In fact, this invention anticipates, and includes as a prophetic example, those anabolic agents that may be completely devoid of androgenic activity. Examples of such growth hormone-releasing agents include: somatoliberins; growth hormone-releasing hormone active fragments, such as, for example, hGRF (1-29) amide and hexarelin (GHRP-6). Hexarelin is a growth hormone releasing peptide mimetic agent, i.e., it mimics the effects of growth hormone releasing peptide in the body and contains between 2 and 20 amino acids. In particularly preferred embodiments, more than one growth hormone-releasing agent may be used in combination. A preferred combination comprises growth hormone-releasing factor (GRF or GHRH) and a growth hormone releasing peptide or peptidomimetic (GHRP). This combination has been reported to act by separate mechanisms for the release of endogenous growth hormone, and the effects have been shown in some cases to be additive, or even, synergistic, working at a separate receptor often called the Ghrelin receptor, to differentiate it from the GHRH receptor. Since the GHrelin receptor has recently been elucidated, prophetically other ligands for this receptor are anticipated to be synthesized and/or discovered in the future, and these are included by example (Baldelli, R et. al., Endocrine 14 (1):95-99, 2001). These are often referred to as GHSs (growth hormone secretagogue).

The administration of a GH or IGF-1 secretagogue will reduce plasma androgen concentration in humans (Tapanainem J. et. al., Fertility and Sterility 58: 726-732). This effect increases the need for exogenous androgen, such as testosterone, to be also administered as a co-treatment to restore and amplify existing levels.

Other compounds are known to affect this system which is known as the hypothalamo-pituitary-hepatic axis for GH, among other terms. Prophetically, it is probable that other compounds involved in this hormonal regulatory system may play a role in indirectly or directly influencing and increasing levels of GH, IGF-1, or IGF-2, and may be administered in the context of this invention along with the androgenic supplementation to get maximal effects of the growth/anti-aging effects of such treatment. Other indications that may be treated besides fibromyalgia may be syndromes affecting the growth of individuals, including but not limited to pituitary dwarfism, conditions or syndromes that are well known to practitioners in the field of endocrinology, growth, and aging.

For the administration of the GH agents that are described in detail above, they may be administered by a variety of means. These agents may be administered separately from the androgen administration, using the modalities of intranasal, transdermal, parenteral (subcutaneous or intravenous), or oral (with or without permeation enhancement and preferably with enteric protection, since proteins and peptides may be degraded by gastric exposure). GH itself is most preferably administered by parenteral means in practice, because it is a large protein that is of limited stability and limited absorption. However, intranasal administration is also an acceptable means for this and other large proteins or peptides.

In addition to a separate delivery modality for the GH agent and the androgenic compound selected for treatment, the two may be combined in a single combination therapy. For example, both could be incorporated together in an oral form, tablet, or suspension, with the caveat that any proteinaceous agent is suitably protected from gastric degradation. Alternatively, the combination of agents may be administered intranasally in one unit through separate delivery chambers, known to those of skill in intranasal delivery, or together in the same liquid, semi-solid, or solid delivery form. For example, a microparticulate or nanoparticulate dry solid system could be administered intranasally. Or the combined agents could be both administered transdermally.

Example 1

A clinical trial was performed to investigate the pharmacokinetics and efficacy of transdermal delivery of hormones for treatment of fibromyalgia, the data from which can be used to plan further studies relating to fibromyalgia-related pain. Women were recruited by institutional review board-approved advertising. Subjects aged 40-55 and diagnosed for fibromyalgia using American College of Rheumatology criteria (11/18 bilateral tender points above and below the waist, chronic fatigue, etc., (Wolfe, F. et al., 1990. Arthrit. Rheumat. 33:160-172) were selected for the study if they fit additional criteria. Women were included if, in addition to meeting all other criteria, they agreed to keep their medicines unchanged during the study (decreases in analgesics were permitted). Women taking hormone replacement therapy were enrolled if they agreed to come off hormone therapy at least 2 weeks prior to, and for the duration of, the study, in addition to meeting other eligibility criteria. Pre- or peri-menopausal women were required to have adequate alternative contraception, a negative pregnancy test, and treatment was started within the follicular (proliferative) phase of the menstrual cycle. Patients were included if they were willing to exercise 20 minutes a day, 5 days per week during therapy, to promote the effects of testosterone; this was a requirement put in place by the Institutional Review Board. It is noted that exercise can be difficult for fibromyalgia patients. It is predicted that exercise alone cannot provide the therapeutic benefit of testosterone replacement therapy; a placebo-controlled study will confirm this prediction.

In this study testosterone was formulated as a gel in a concentration that is appropriate for women, and showed effective systemic delivery of testosterone in patients with fibromyalgia. The patients received 28 days of therapy with 0.75 g 1% (w/w) testosterone gel once per day. Serum concentrations of total and free testosterone were raised in these fibromyalgia patients to concentrations approximating those in premenopausal women. At this dose, patients showed significantly decreased fibromyalgia-related muscle pain, decreased stiffness, decreased fatigue and increased libido in response to testosterone therapy. Fibromyalgia-related tender point pain was significantly decreased, as well. These very encouraging results, from both the pharmacokinetic and fibromyalgia-related pain assessment standpoints, support the use of testosterone replacement therapy to treat individuals with fibromyalgia syndrome in a formal double blind placebo-controlled study. Further, the conclusions of efficacy in patients with fibromyalgia syndrome in response to increased serum concentrations of testosterone parallel the positive outcomes found with testosterone replacement therapy in other populations with chronic fatigue and muscle wasting, e.g., AIDS and Parkinson's Disease.

Children, pregnant women, and women on hormone therapy, hormone contraceptives or infertility drugs were excluded. Women were excluded from the study if they reported undiagnosed vaginal bleeding, had a body mass index BMI>30, admitted to ethanol or illicit drug abuse, had active thrombophlebitis, breast cancer, hypertension (BP>160 systolic/95 diastolic with or without medication, after sitting 5 minutes), or major skin disease, acne or hirsutism.

Prior to enrollment, study patient blood was tested for the following general health criteria (exclusion criteria in parentheses): cardiac risk factors by lipid profile—total fasting cholesterol (>240 mg/dL), high density lipoprotein (<35 mg/dL), low density lipoprotein (>210 mg/dL), triglyceride (>300 mg/L); hepatic function by alanine aminotransferase (>1.5×N; normal at 0-40 U/L), alkaline phosphatase (>2×N; normal at 40-120 U/L), aspartate aminotransferase (>1.5×N; normal at 10-30 U/L), serum albumin (>N; normal at 3.2-5.2 g/dL), total bilirubin (>N; normal at 0.2-1.3 mg/dL), and direct (conjugated, soluble) bilirubin (>N; normal at 0.0-0.3 mg/dL); kidney function by blood urea nitrogen (>2×N; normal at 8-18 mg/dL) and serum creatinine (>N; normal at 0.7-1.2 mg/dL) tests; hematological function was assessed by complete blood cell count including testing for hemoglobin (normal; 12-16 g/dL).

Blood tests and physical exam at the end of the study were performed to assess whether testosterone therapy adversely affected the general health of the study patient. Serum total testosterone (>0.4 ng/mL) and FSH (<22 IU/L) were tested as well (8:00 AM after overnight fasting), to confirm patients had concentrations of testosterone in the lower half of the reference range (2 patients out of 18 were excluded based on testosterone concentrations) and to determine their post-menopausal status. FSH concentrations<22 IU/L indicated premenopausal or peri-menopausal status and thus the need for adequate contraception, unless the patient had undergone bilateral oophorectomy. Testosterone serum concentrations were tested at 8:00 AM due to the small circadian rhythm of circulating androgens. The most frequent exclusion criterion was for BMI>30. Patients were required to stop taking St. John's wort, since St. John's wort is known to induce catabolism of hormones by activating CYP3A, a detoxifying enzyme complex in the liver.

Written informed consent was obtained from study subjects prior to entry into the study. This consent process was ongoing throughout the study, and an independent Data Safety Monitoring board was in place for the duration of the study. Twelve patients who fit the eligibility criteria, above, were scheduled for physical exams including tender point assessment, verification of fibromyalgia diagnosis, and assessment of general health.

On day 1, blood was drawn by venipuncture at 0, 1, 2, 3, 4, 6, 8, 10, 12 and 24 hrs for 24 hr pharmacokinetic profiling of baseline testosterone serum concentrations. Testosterone gel, 0.75 g 1% w/w, was applied by the patients to their lower abdominal skin just after the zero time point blood draw (8:00 AM). The patients also filled out a fibromyalgia-related pain assessment questionnaire form and were given packets of testosterone gel for 8:00 AM daily application to lower abdominal skin, instructions for use and a patient medication log and exercise log for 28 days of therapy. On day 28, the blood draws for 24 hr pharmacokinetic profiling were repeated, and a follow-up exam was repeated at the end of the 28 days of therapy.

The delivery vehicle for this study was a gel formulation. A goal of the study was to identify a transdermal delivery system for hormones that would result in effective levels of hormones in blood as a way to reduce side effects of androgen therapy. The gel used for this study was a 1% w/w testosterone gel, USP grade. The once-a-day daily unit dose applied was about 7.5 mg testosterone; the expected bioavailability of 10%, industry standard for transdermal delivery, would deliver about 0.75 mg testosterone over 24 hr. The gel was formulated for women by Bentley Pharmaceuticals, Inc. (Exeter, N.H., a former division of CPEX Pharmaceuticals, Inc.) using good manufacturing practice standards, and is quick-drying, odorless, colorless, comfortable on the skin, and non-staining. Since testosterone is a Schedule C-III controlled substance under the Anabolic Steroid Control Act, all testosterone treatment samples were itemized and accounted for at the conclusion of the study.

Testosterone concentrations were determined by enzyme linked immunoassay (EIA, Diagnostic Systems Laboratories or DSL, Inc, Webster, Tex.), where serum testosterone from study subjects competed with enzyme-linked testosterone bound to anti-testosterone mAb. This assay system was designed to detect the lower concentrations of testosterone found in women as well as concentrations in the upper ranges. Free testosterone concentrations were determined by EIA using an anti-testosterone antibody that recognizes the unbound testosterone in the test sample, and has low affinity for sex hormone binding globulin and albumin. Reference ranges for the DSL detection system are given in Table 1 above. For the purposes of determining mean testosterone concentrations, times were based on the nearest hour. Of the 240 time points taken for the pharmacokinetic data (10 time points per individual×2 sets per individual×12 individuals), 1 time point was missed (4 hr point) and 3 additional time points were in between the standard times for taking blood (8 hr point; 4 hr and 10 hr points). Values for these time points were derived by interpolation for the purposes of deriving mean testosterone concentrations. A noncompartmental pharmacokinetic analysis using WinNonlin Pro (Pharsight, Mountain View, Calif.) used the exact time points recorded for all the patients.

In order to determine the efficacy of the treatment for reducing symptoms of fibromyalgia, patients filled out questionnaire forms on day 1 and again at the end of therapy on day 28 to assess fibromyalgia-related pain. The patient questionnaire was based on a published and validated Fibromyalgia Impact Questionnaire as well as other accepted criteria for fibromyalgia patient assessment (Wolfe, F. 1990. Arthrit. Rheumat. 33:160-172; Goldenberg, D. 1996. Arthrit. Rheumat. 39:1852-1859; Burckhardt, C. S. 1991. J. Rheumatol. 18:728-733), and used a 100 mm visual analog scale (VAS). Tender point exams were administered by a qualified rheumatologist experienced in treating women with fibromyalgia, and involved applying approximately 9 pounds of pressure at each tender point and asking whether the patient felt fibromyalgia-related pain. This practice is in accordance with criteria specified by the American College of Rheumatology. Exams were administered just prior to Day 1 of therapy (and therefore designated as "pretreatment"), and at the end of therapy. The pretreatment tender point assessment was performed on all patients within 1 week before the start of therapy. Dolorimeter readings were taken from the bilateral second costochondral junction and trapezius tender points, for comparison, in 11 of the 12 study subjects.

Pharmacokinetic analysis of serum testosterone concentration data was carried out using WinNonlin Pro software, using the noncompartmental model with extravascular input. Differences between Day 1 and Day 28 maximum plasma concentrations ($C_{max}$) and area under the curve (AUC) of a plot of plasma concentrations over time were assessed by calculating individual subject Day 28 minus Day 1 data and estimating 95% confidence intervals of this difference to determine if significance (p<0.05) was reached. Tender point data evaluations were analyzed by Student's t test (paired, 2-tailed) after summing all 18 tender point values for each individual at baseline versus day 28 of the study.

Eighteen patients were screened and evaluated for enrollment in the study. Twelve fibromyalgia patients aged 40-55 who met the study eligibility criteria were enrolled for this study and treated. All patients were white Caucasian females. Patient demographics for age, height and weight are shown in Table 2 below.

TABLE 2

Patient Demographics

| Pat ID# | Age | Ht (in) | Wt (lb) | BMI |
|---|---|---|---|---|
| 001 | 54 | 66 | 155 | 25.1 |
| 002 | 54 | 62 | 139 | 25.9 |
| 005 | 51 | 64 | 150 | 26.0 |
| 006 | 53 | 60 | 130 | 25.5 |
| 007 | 54 | 62 | 160 | 29.3 |
| 009 | 53 | 67 | 160 | 25.1 |
| 010 | 45 | 67 | 175 | 27.5 |
| 011 | 50 | 62 | 135 | 24.8 |
| 012 | 54 | 62 | 122 | 22.4 |
| 016 | 55 | 64 | 140 | 24.3 |
| 017 | 45 | 62 | 140 | 25.7 |
| 018 | 42 | 64 | 130 | 22.4 |
| Mean | 51 | 63 | 145 | 25.3 |
| Median | 53 | 63 | 140 | 25.3 |
| Minimum | 42 | 60 | 122 | 22.4 |
| Maximum | 55 | 67 | 175 | 29.3 |

Figure 1B:
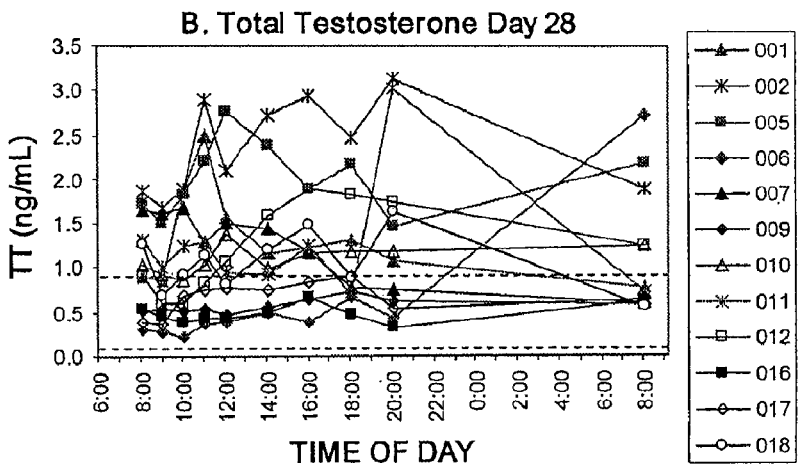
Figure 1C:
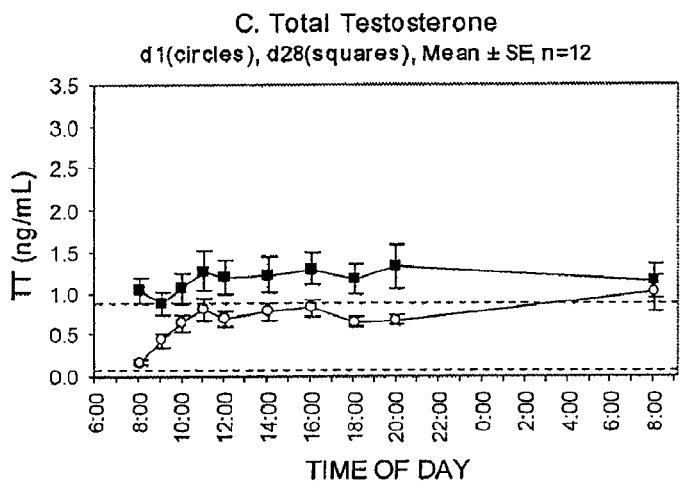

Analysis of the blood testosterone concentration data revealed that serum total testosterone concentrations were reliably increased in fibromyalgia patients in response to testosterone gel hormone replacement therapy. Serum total testosterone concentrations versus time data for Day 1 and Day 28 are shown in FIGS. 1A-1C. Reference ranges for the concentration of total testosterone in serum from women aged 40-50 and 50-60 are provided in Table 1 above and denoted by dashed horizontal lines in FIGS. 1A-1C.

FIGS. 1A-1C relate to the serum total testosterone concentrations in fibromyalgia patients and show that these concentrations are increased in response to testosterone gel therapy. Blood was taken by venipuncture from twelve fibromyalgia patients who fit the eligibility requirements, on day 1 at the times indicated and then again on day 28 of therapy. Low and high ends of the reference range are as indicated by the dashed horizontal lines, and as specified in ng/mL±0.71 SD on day 1, p<0.05 (Table 3 below). Significantly increased mean total testosterone area under the curve values (assessed over the 24 hr profiling time period) were also found: AUC was 28.75 ng-h/mL±13.91 SD on day 28 compared with 18.36 ng-h/mL±7.10 SD on day 1, p<0.05. The differential $C_{max}$ and AUC values for day 28 after subtraction of day 1 baselines are provided in the right panel of Table 3.

TABLE 3

Total Testosterone Pharmacokinetic Parameters

| | Total Testosterone d1 (n = 12) | | | | Total Testosterone d28 (n = 12) | | | | d28-d1 Differential | | |
|---|---|---|---|---|---|---|---|---|---|---|---|
| | $T_{max}$ h | $C_{max}$ ng/mL | $C_{min}$ ng/mL | $AUC_{(0-24\ hr)}$ ng · h/mL | $T_{max}$ h | $C_{max}$ ng/mL | $C_{min}$ ng/mL | $AUC_{(0-24\ hr)}$ ng · h/mL | $C_{max}$ ng/mL | $C_{min}$ ng/mL | $AUC_{(0-24\ hr)}$ ng · h/ml |
| Mean | | 1.21 | 0.17 | 18.36 | | 1.92 | 0.72 | 28.75 | 0.7 | 0.55 | 10.38 |
| SD | | 0.71 | 0.10 | 7.10 | | 0.90 | 0.44 | 13.91 | 0.96 | 0.42 | 12.61 |
| Median | 16.11 | 1.08 | 0.18 | 16.88 | 10.17 | 1.79 | 0.61 | 26.71 | | | |
| Min | 2.33 | 0.53 | 0.00 | 10.35 | 1.62 | 0.63 | 0.21 | 11.29 | | | |
| Max | 24.75 | 3.05 | 0.37 | 30.95 | 23.92 | 3.13 | 1.67 | 59.56 | | | |
| 95% CIs For Diff | | | | | | | | CI high -> | 1.36 | 0.79 | 19.23 |
| | | | | | | | | CI low -> | 0.06 | 0.31 | 1.55 |

Table 3. FIG. 1A shows the day 1 profile, FIG. 1B shows the day 28 profile, and FIG. 1C shows the means±SEM for day 1 (open symbols) versus day 28 (filled symbols).

The day 1 zero time point for total testosterone confirmed that these patients initially had total testosterone concentrations in the lower half of the reference range. The mean serum concentration of total testosterone 24 hr after application of the first dose of hormone on Day 1 was significantly higher than the mean serum concentration for time zero on Day 1 (FIG. 1C, p=0.01), indicating that serum concentrations reached steady state very quickly, within 24 hr, in the population aggregate during the 28 day time course. Testosterone concentration versus time data, therefore, did not permit estimation of half-life. Steady state concentrations were maintained by day 28, as evidenced by the similar mean concentrations at the beginning and end of the 24 hr sampling. Interestingly, and not unexpectedly, substantial variation was found in the 24 hr profiles on an inter-individual basis, consistent with the complex regulation known for this hormone.

Summary pharmacokinetic parameter analysis demonstrated significantly increased mean total testosterone maximum concentration in response to testosterone therapy: $C_{max}$ was 1.92 ng/mL±0.90 SD on day 28 compared with 1.21

The pharmacokinetic data for total testosterone, all together, demonstrate that with therapy, mean serum total testosterone concentrations initially rose quickly over the first 3 hours and were then reliably sustained over time. In addition, mean serum concentrations were raised from the lower boundary of the reference range to about the upper end of the reference range for premenopausal women.

Low free testosterone concentrations in serum are raised to premenopausal concentrations in fibromyalgia patients in response to testosterone gel hormone replacement therapy.

TABLE 4

Free Testosterone Pharmacokinetic Parameters

| | Free Testosterone d1 (n = 10) | | | | Free Testosterone d28 (n = 10) | | | | d28-d1 Differential | | |
|---|---|---|---|---|---|---|---|---|---|---|---|
| | $T_{max}$ h | $C_{max}$ pg/ml | $C_{min}$ pg/mL | $AUC_{(0-24\ hr)}$ pg · h/ml | $T_{max}$ h | $C_{max}$ pg/ml | $C_{min}$ pg/mL | $AUC_{(0-24\ hr)}$ pg · h/ml | $C_{max}$ pg/ml | Cmin pg/mL | $AUC_{(0-24\ hr)}$ pg · h./ml |
| Mean | | 2.64 | 0.54 | 35.0 | | 3.91 | 1.29 | 53.89 | 1.27 | 0.75 | 18.9 |
| SD | | 1.70 | 0.41 | 18.3 | | 1.23 | 0.54 | 18.71 | 1.71 | 0.72 | 27.1 |
| Median | 6.38 | 2.19 | 0.41 | 31.8 | 9.13 | 4.16 | 1.12 | 51.49 | | | |
| Min | 1.92 | 0.95 | 0.09 | 13.7 | 0.00 | 1.81 | 0.71 | 27.95 | | | |
| Max | 24.8 | 6.86 | 1.35 | 64.1 | 24.05 | 5.58 | 2.27 | 90.08 | | | |
| 95% CIs For Diff | | | | | | | | CI high -> | 2.33 | 1.19 | 35.6 |
| | | | | | | | | CI low -> | 0.21 | 0.30 | 2.10 |

Figure 2A:
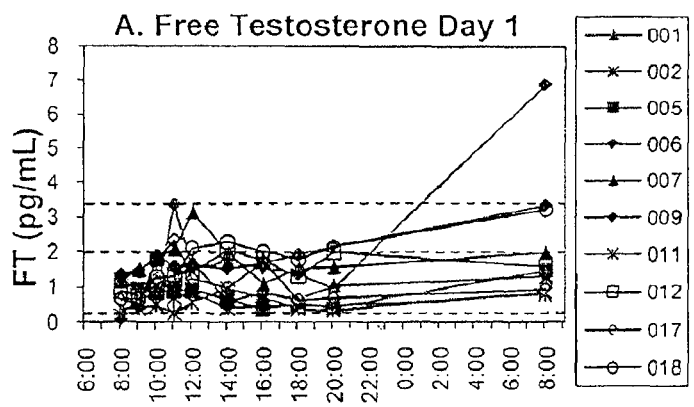
FIGS. 2A-2C depict the levels of free testosterone in blood of the patients.
Figure 2B:
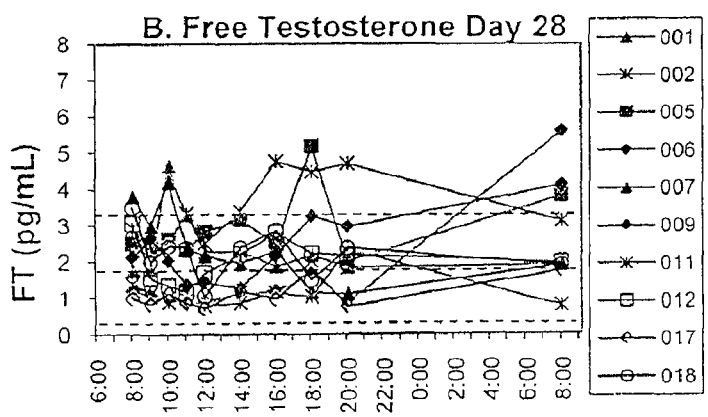
Figure 2C:
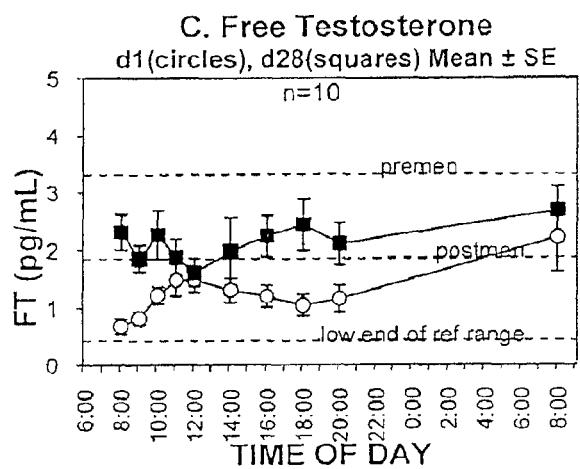

Concentrations of free testosterone in serum were analyzed similarly to total testosterone, with the results shown in FIGS. 2A-C. Serum free testosterone concentrations were quantitated using methodology similar to FIGS. 1A-1C. The low end of the reference range for this study for pre- and post-menopausal women was 0.33 pg/mL, represented by the lower dashed horizontal line. The high end of the reference range for premenopausal women is represented by the upper dashed horizontal line, and the high end for post-menopausal women is represented by the middle dashed horizontal line (FIG. 2 and Table 1). FIG. 2A shows the day 1 profile. FIG. 2B shows the day 28 profile. FIG. 2C shows the means±SEM for day 1 (open symbols) versus day 28 (filled symbols), with a change in the y-axis scale. Patient IDs are provided in the legend for FIGS. 2A and 2B.

These results were similar to the previous findings, but with the following particular findings. Two individuals had unusually high concentrations of free testosterone prior to, and throughout, the course of therapy despite normal total testosterone levels, suggesting serum interference with the free testosterone testing antibody in these two cases. (The only medication and/or supplement reported by both study subjects, and not by any other subjects, was ginger root, and the anti-depressant Trazodone was taken by both individuals. Preliminary data, from spiking the assay with ginger root or Trazodone, are consistent with interference by ginger root and/or Trazodone with the enzyme linked immunoassay for free testosterone: 1) for a proof-of-concept finding, others have shown that DHEA-S can interfere with testosterone immunoassays; 2) here, day 1, 0 hr baseline free testosterone blood levels were higher than was biologically reasonable and did not increase further with therapy; 3) these two individuals had low total testosterone baseline levels such that if the baseline free testosterone levels were real, a much larger fraction of the total testosterone would have been free testosterone than the normal 1-4%; 4) the free testosterone for these individuals was about 3-10× the reference range, a level that approaches the levels found in males; 5) these individuals would have been at high risk for hirsutism if these free testosterone blood levels were indeed so much higher than the reference range; and 6) this study excluded patients with hirsutism. For these reasons, these two outliers were deleted from the analysis). Individual profiles for the remainder of the patients showed concentrations that increased from the post-menopausal range to the premenopausal and upper post-menopausal reference range.

Summary pharmacokinetic parameter analysis showed a mean free testosterone $C_{max}$ of 4.69 pg/mL±2.17 SD on day 28 compared with 3.68 pg/mL±2.99 SD on day 1 (p>0.05) [adjust for outliers] and a mean free testosterone AUC of 71.38 pg-h/mL±45.76 SD on day 28 compared with 54.35 pg-h/mL+49.83 SD on day 1 (p>0.05) (Table 4). Free testosterone $C_{max}$ and AUC were increased with therapy, as evidenced by subtraction of the day 1 baseline from day 28 values, but statistical significance was not achieved [adjust for outliers] in these pharmacokinetic parameters due to the two individuals with exceptionally high free testosterone concentrations.

Figure 3:
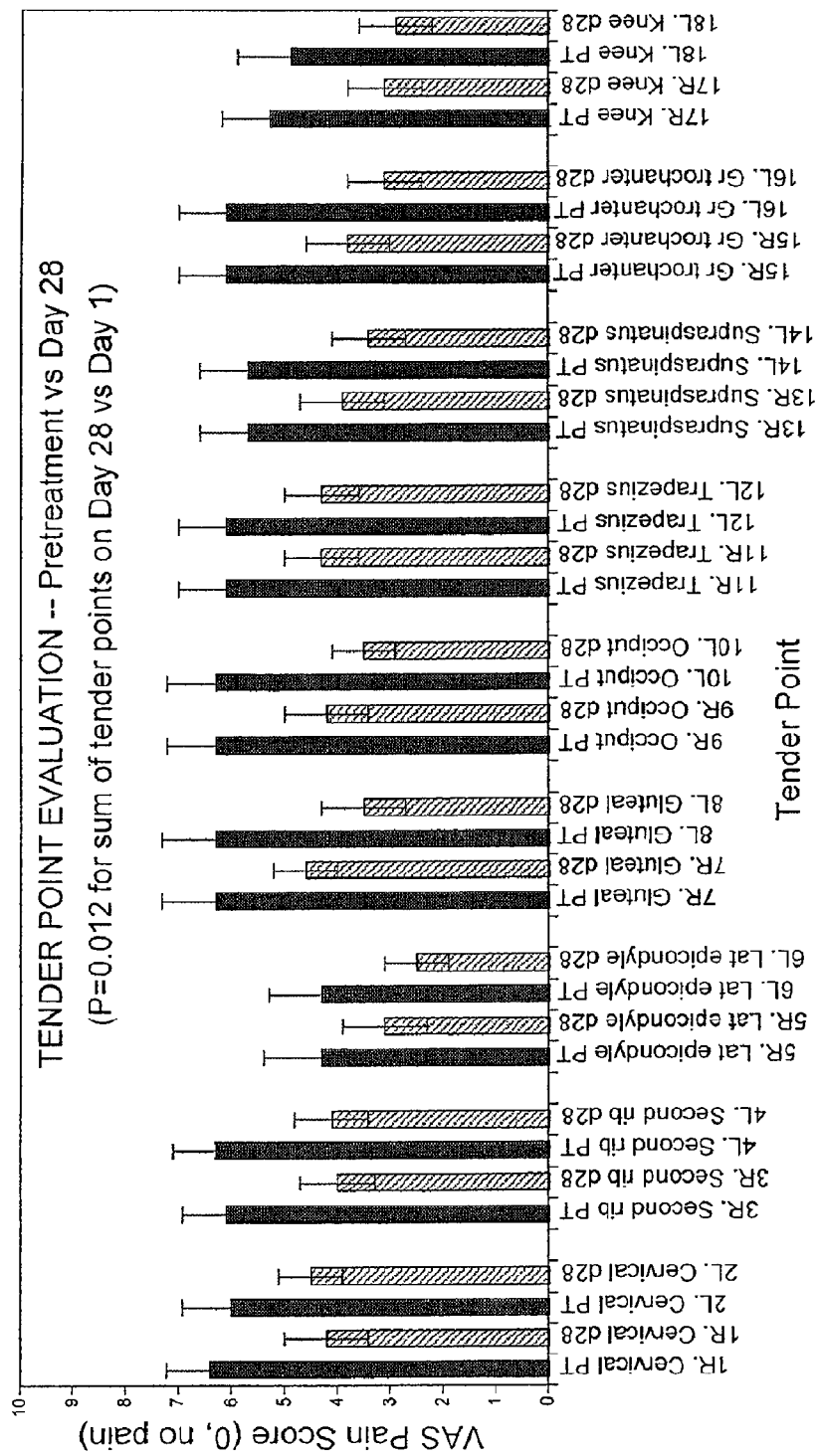
FIG. 3 depicts the results of the tender point evaluations pre-treatment (day 0) and at the end of the study (day 28). The results reported are levels of fibromyalgia-related pain on a scale of 0 (no pain) to 10 (highest level of pain).

Testosterone gel therapy is associated with a statistically significant reduction in fibromyalgia-related tender point pain comparing scores at the beginning of therapy and at the end of therapy. These evaluations were conducted a rheumatologist, the results are shown in FIG. 3. Tender points defined in Table 4. Analysis of the tender point data showed that transdermal testosterone gel therapy was associated with decreased subjective assessments of tender-point pain. Using a pain scale of 0 to 10, where zero is no pain, there were mean decreases in pain for every tender point, with statistical significance achieved after summing values across all 18 tender points (p=0.012), a finding that compares favorably to studies using calcium channel blockers or SNRI therapeutics to treat fibromyalgia patients. The results are shown in FIG. 3, which demonstrates that fibromyalgia-related tender point pain was decreased in fibromyalgia patients after testosterone gel therapy. Tender point exams were administered by the study rheumatologist. Fibromyalgia-related pain was assessed on a visual analog scale (VAS) of 0-10, with zero being no pain, and 10 being the most pain. The p value, determined by summing all tender point values for each patient at the baseline versus d28 time points and assessing by paired Student's T-test, was p=0.012. The tender points indicated along the abscissa are defined in Table 5. The dark bars of FIG. 3 indicate pretreatment (PT) measurements and the hatched bars indicate measurements taken on day 28.

Figure 4:
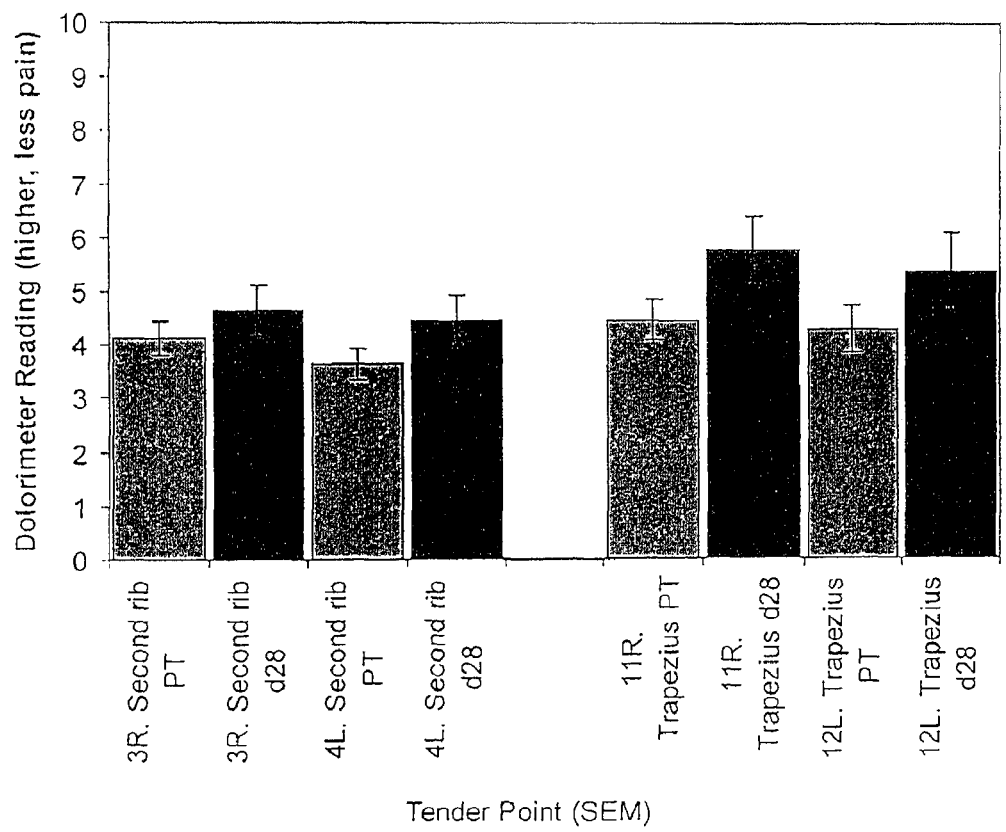
FIG. 4 depicts the results of the dolorimetry assessment of tender point fibromyalgia-related pain pre-treatment (day 0) and at the end of the study (day 28).

Using a dolorimeter to assess fibromyalgia-related pain at the same office visit, pain responses were quantitated for the bilateral second costochondral junction and bilateral trapezius tender points (n=10). FIG. 4 shows that fibromyalgia-related tender point pain threshold was increased in fibromyalgia patients after testosterone gel therapy. Tender points were assessed independently by dolorimeter, with higher readings indicating a higher threshold for fibromyalgia-related pain. Thus, increased values were expected in response to testosterone gel therapy. A limited number of tender points were evaluated by this method in 10 study subjects. Individual response values ranged from 2 to 9. Mean dolorimeter values for the pressure at which patients reported fibromyalgia-related pain were higher at the end of 28 days of testosterone treatment, which would be expected if therapy increased thresholds of fibromyalgia-related pain, although the dolorimetry results did not reach statistical significance. Therapy over a longer period of time, with a greater number of subjects and/or over more tender points is likely to provide significance by dolorimeter assessment.

TABLE 5

| TP# | Tender Point | Description | Lay description |
|---|---|---|---|
| 1-2 | Lower Cervical | Bilateral lower cervical (paraspinals) at the anterior aspect of the intertransverse spaces at C5-7 | At the base of the neck in the back |
| 3-4 | Second rib | Bilateral at the second costochondral junction (rib-cartilage) just lateral to the junction of the upper surface | On the breast bone |
| 5-6 | Lateral epicondyle | Bilateral lateral epicondyle in forearm, 2 cm distal to the epicondyles | On the outer edge of the forearm about an inch below the elbow |
| 7-8 | Gluteal | Bilateral gluteal in the upper outer quadrant of buttock in the anterior fold of muscle | On the outside of the hip |
| 9-10 | Occiput | Bilateral occiput at the insertion of the suboccipital muscle | At the base of the skull beside the spinal column |
| 11-12 | Trapezius | Bilateral trapezius at midpoint of the upper border | On the top of the shoulder toward the back (flat triangular muscle post. neck, shoulder) |
| 13-14 | Supra-spinatus | Bilateral supraspinatus at its origin above the scapular spine near the medial border | Over the shoulder blade |
| 15-16 | Greater trochanter | Bilateral greater trochanter posterior to the trochanteric prominence | At the top of the hip |
| 17-18 | Knee | Bilateral knee at the medial fat pad just proximal to the joint line | On the fat pad over the knee |

1-8 anterior
9-18 posterior

A p value of p=0.17 for the dolorimetry data was derived using summed tender point values, similar to FIG. 3. The dark bars indicate pretreatment (PT) measurements and the diagonal bars indicate Day 28 measurements.

Figures 5A, 5B:
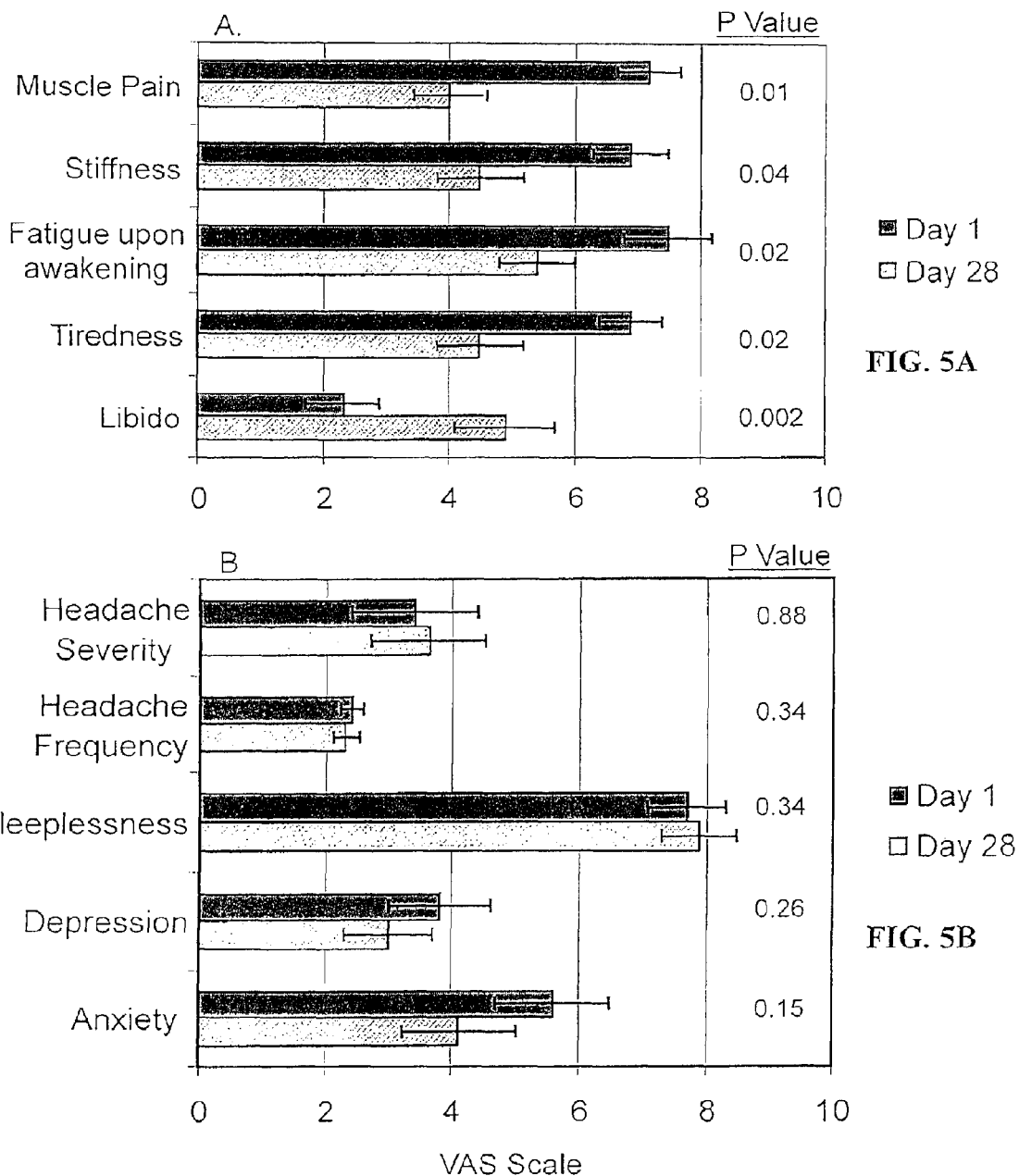
FIGS. 5A-5B depict the severity of symptoms/conditions associated with fibromyalgia and chronic fatigue on a scale of 1 to 10 (10 being the highest increased level) on day 1 versus day 28 of the study. The symptoms/conditions assessed included libido, fibromyalgia-related muscle pain, tiredness, headache severity, headach frequency, stiffness, sleeplessness, fatigue upon awakening, anxiety, and depression.
Figure 6A:
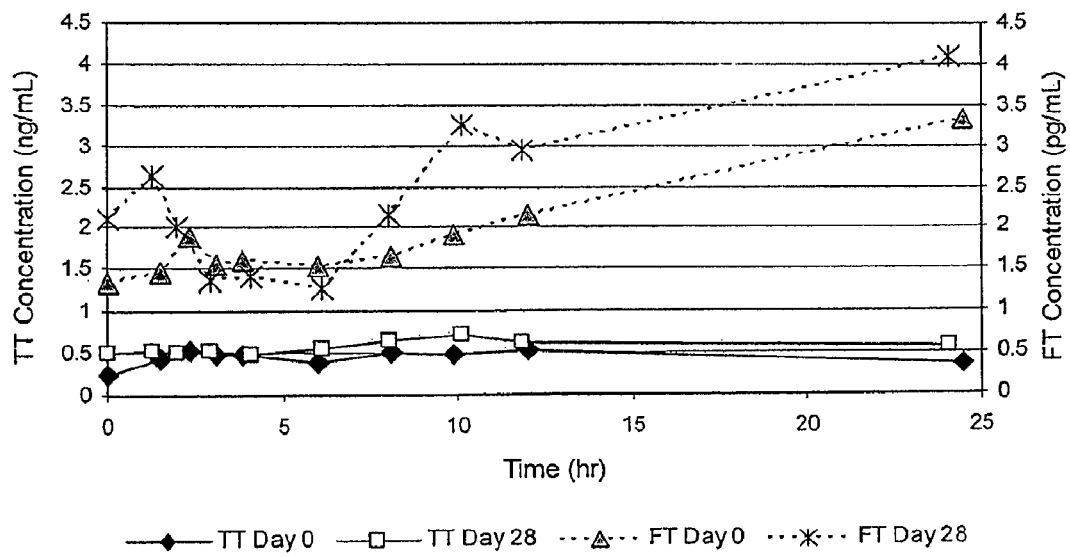
FIGS. 6A-6M show the total and free testosterone levels for each of the individual patients and a graph showing the mean of the subjects and the values for $C_{min}$, $C_{max}$, and $C_{ave}$.
Figure 6B:
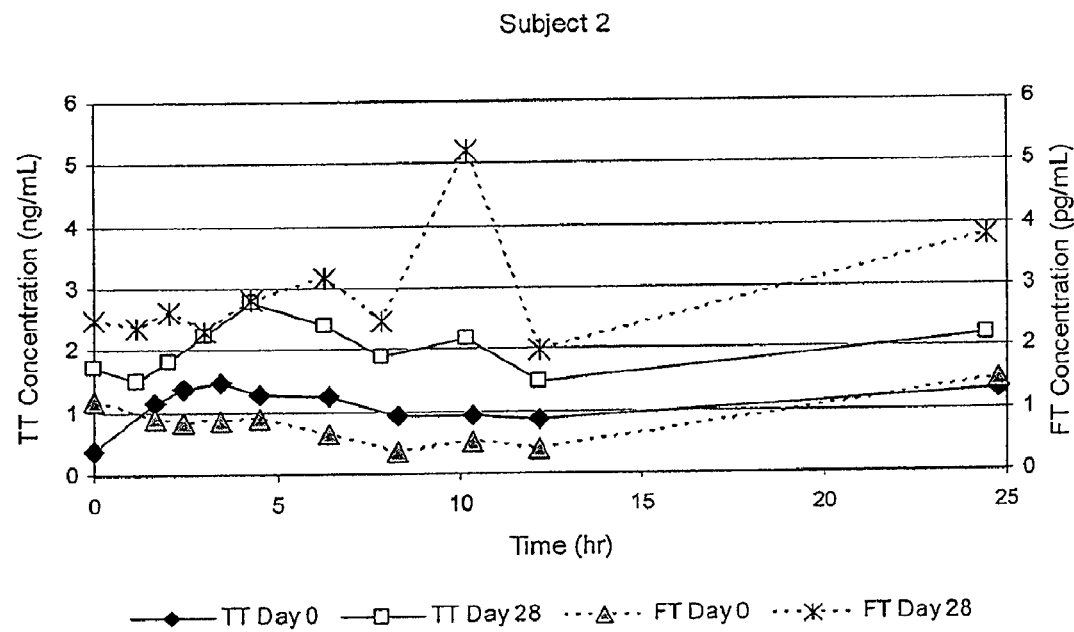
Figure 6C:
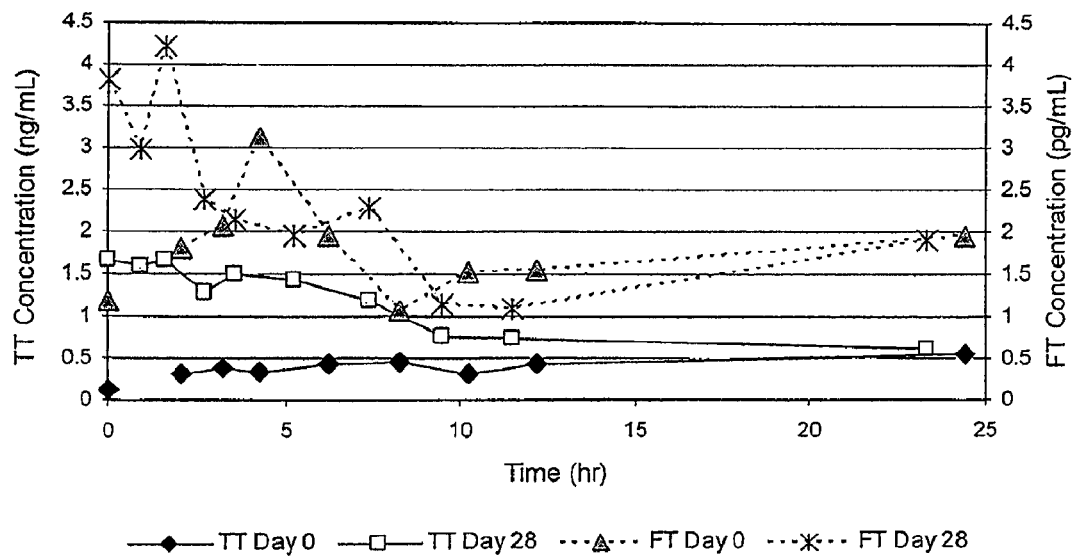
Figure 6D:
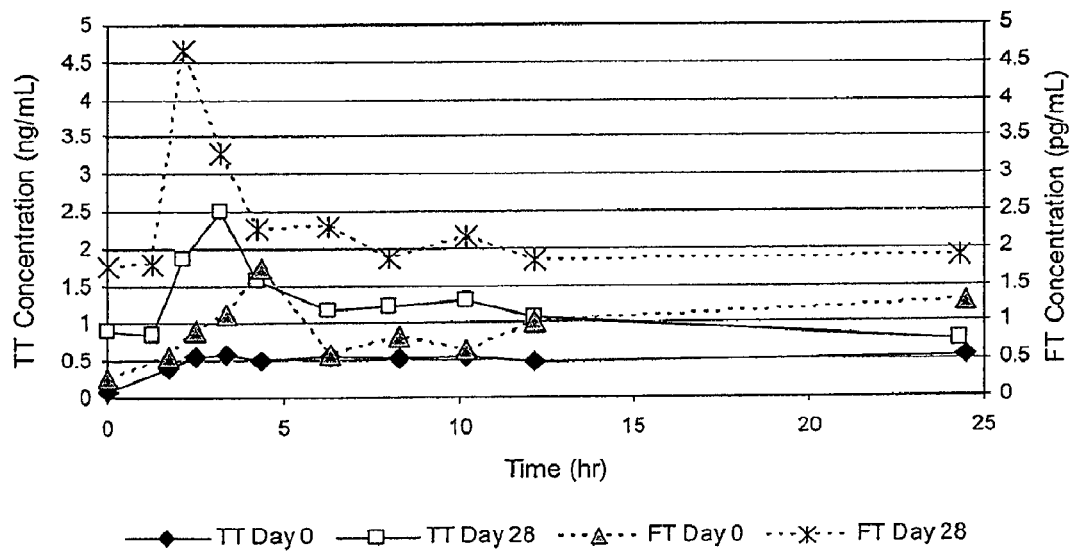
Figure 6E:
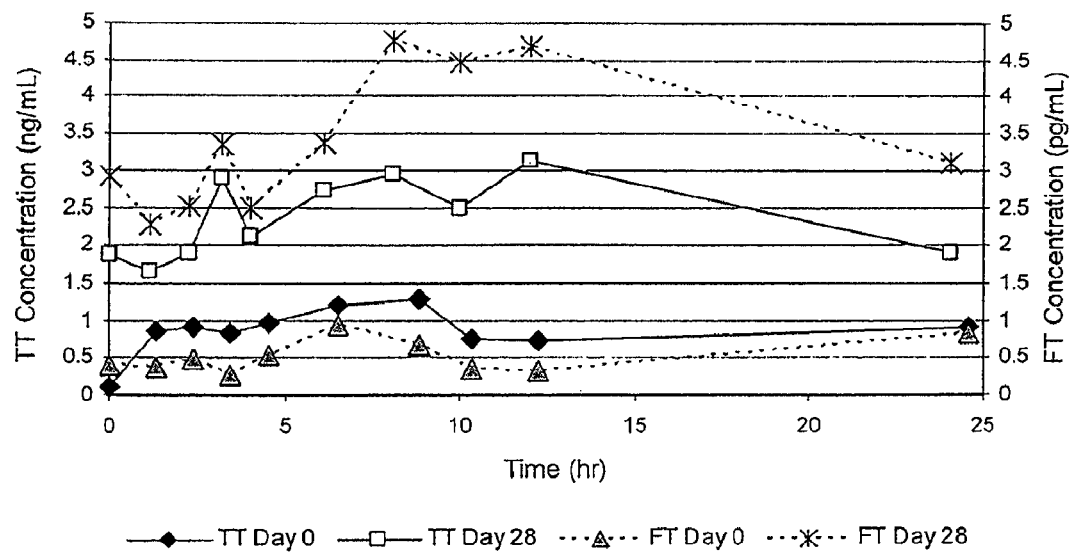
Figure 6F:
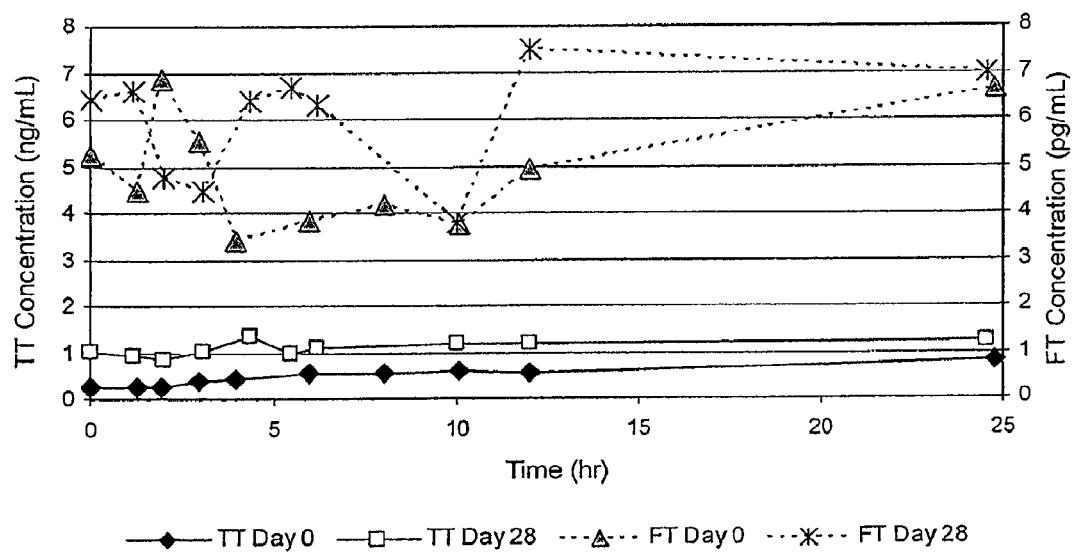
Figure 6G:
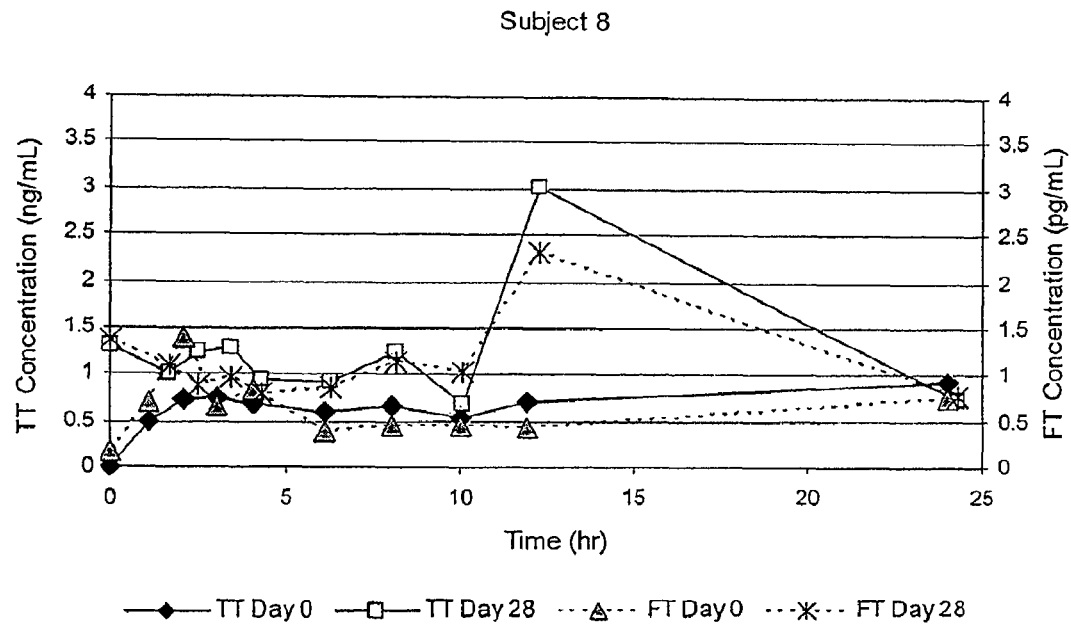
Figure 6H:
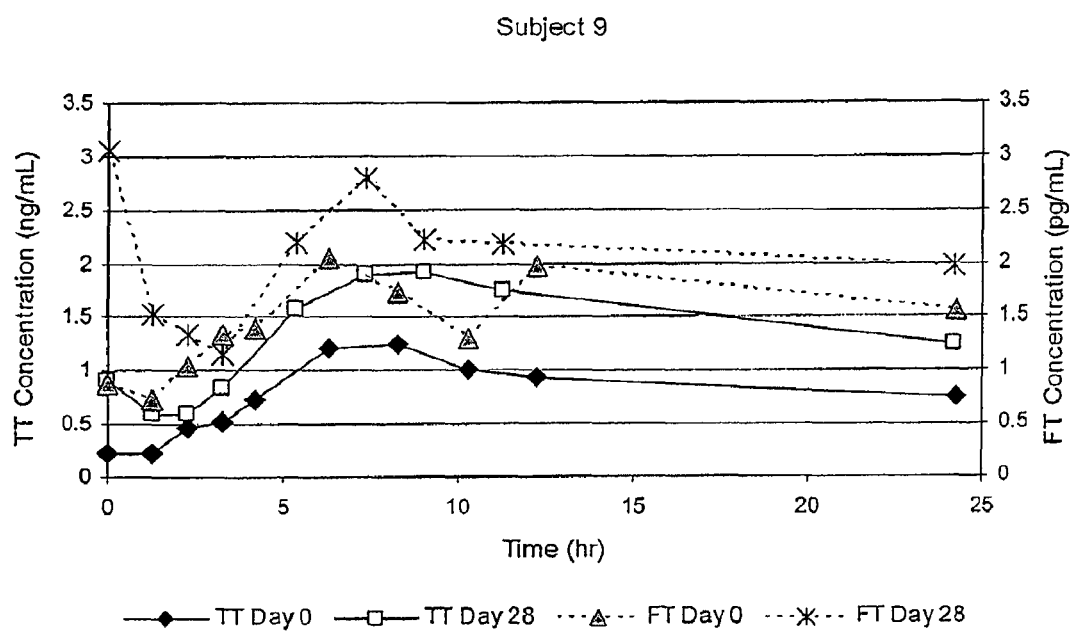
Figure 6I:
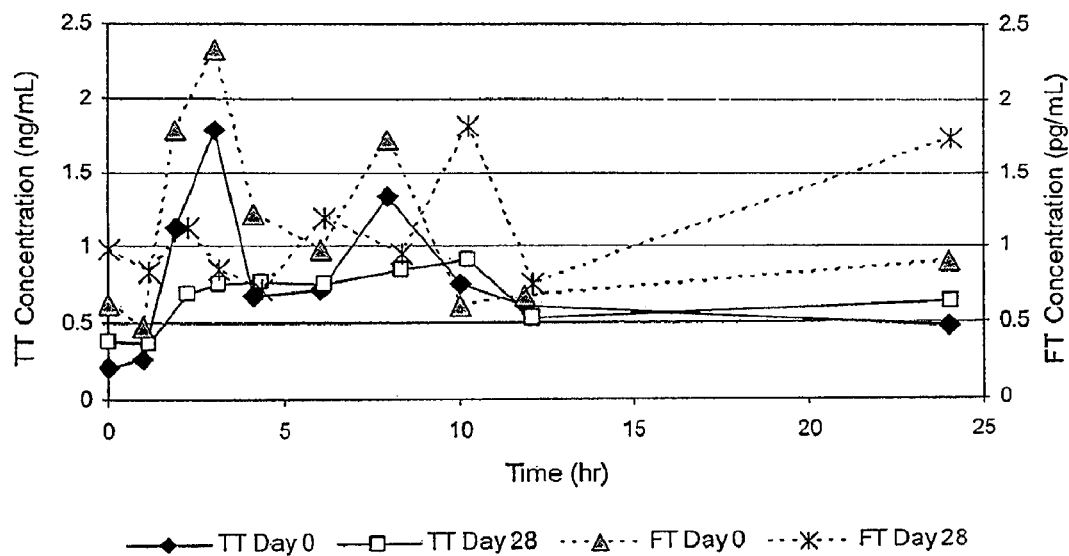
Figure 6J:
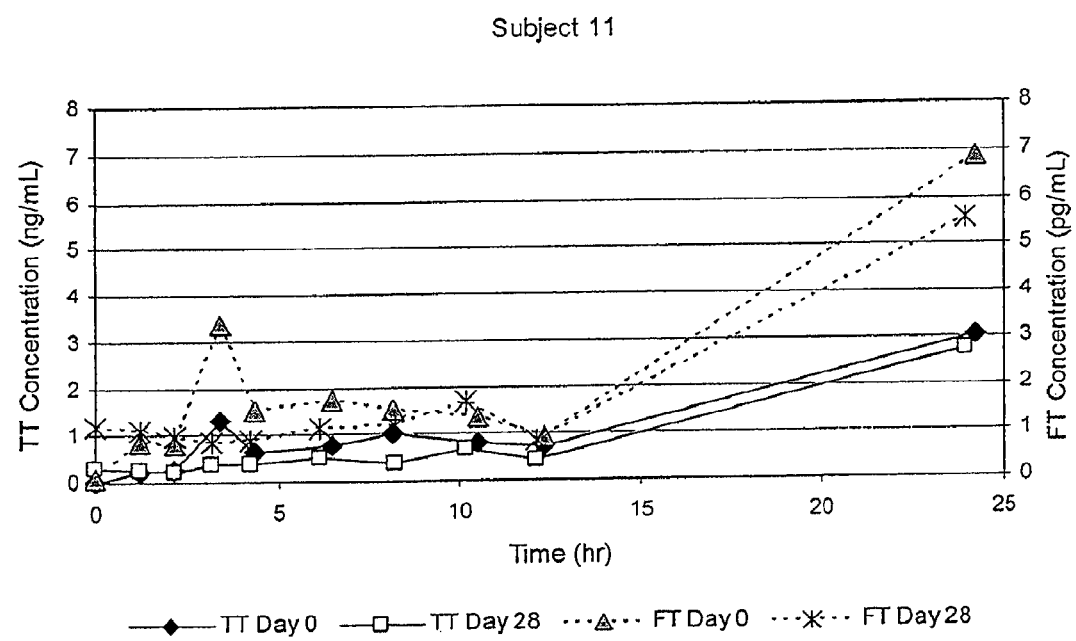
Figure 6K:
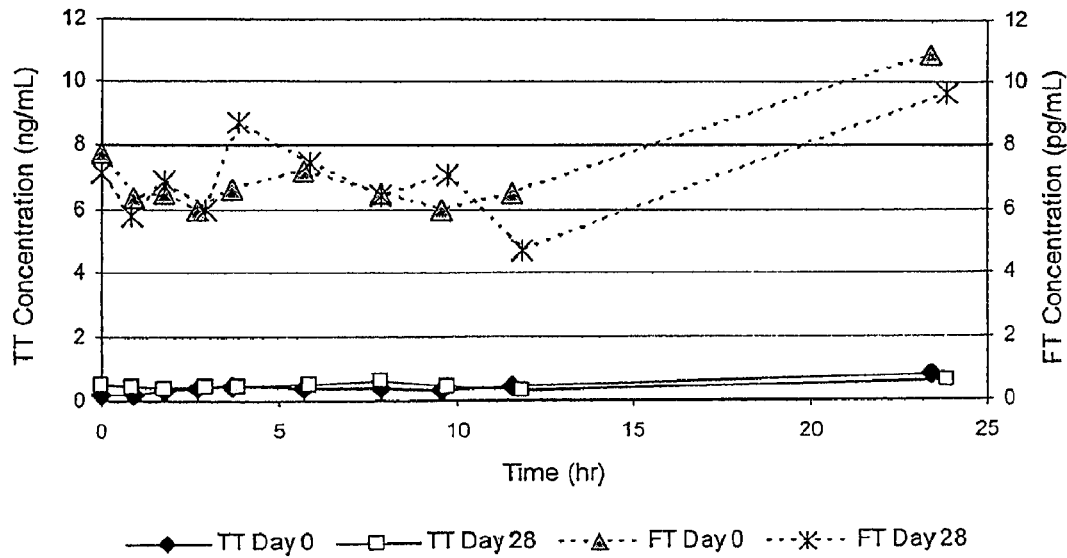
Figure 6L:
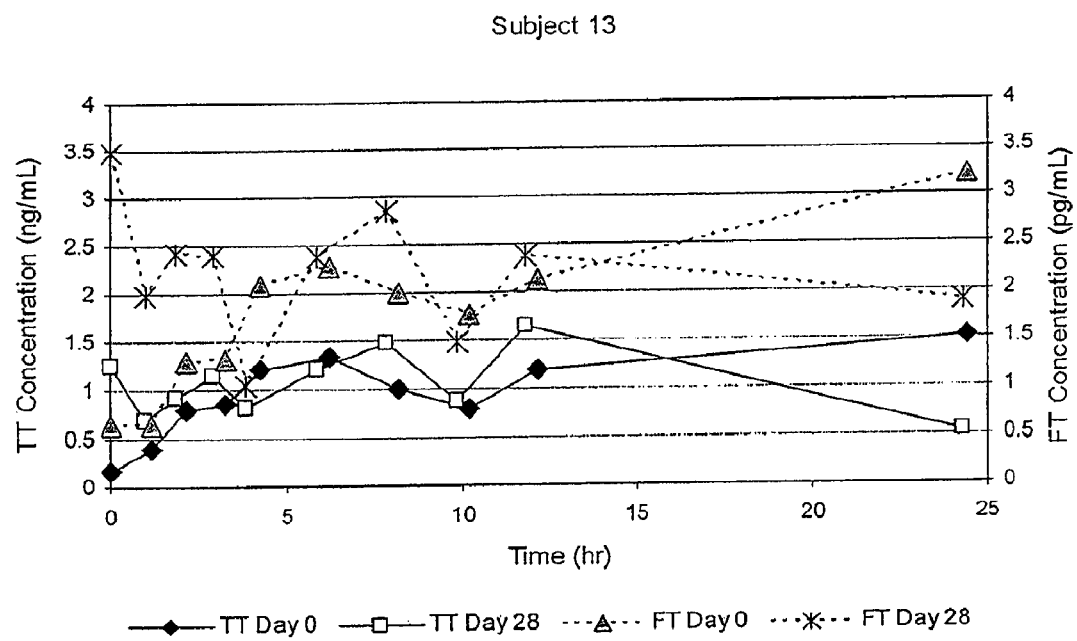
Figure 6M:
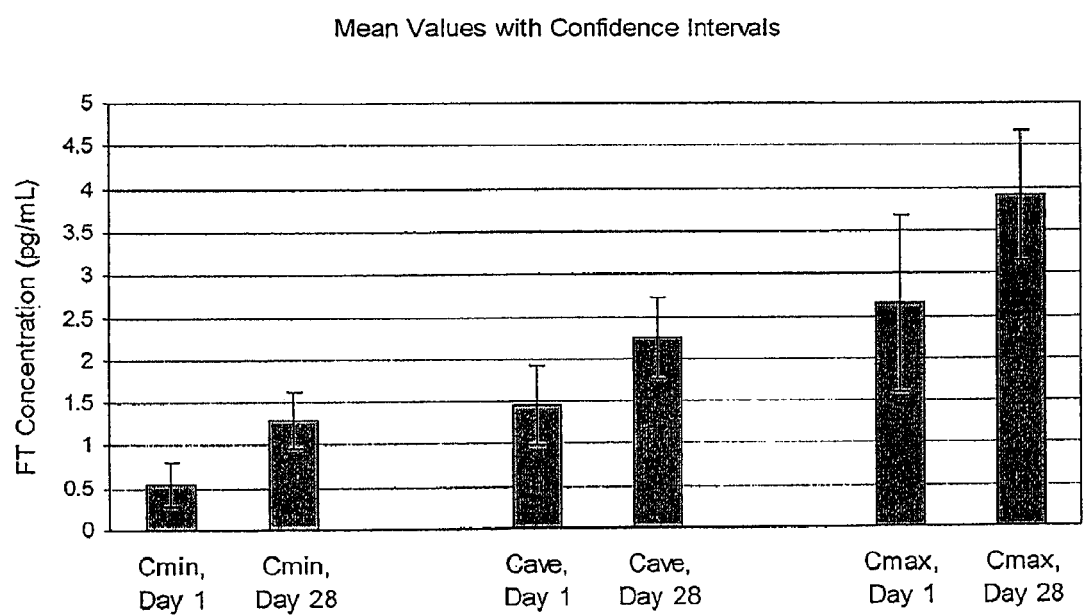

Fibromyalgia-related pain parameters were also evaluated by patient questionnaire using a visual analog scale (VAS) from 0-10. FIGS. 5A-5B show that fibromyalgia symptoms were improved in fibromyalgia patients after testosterone gel therapy. Patients were administered a Patient Questionnaire Form by the study coordinator to assess their feelings of pain. For libido, 10 represents the strongest feelings of libido (sex drive or drive/joy in life; increases expected in response to therapy). For the remaining categories, 10 represents the worst severity of symptoms (decreases expected in response to therapy), with the exception that headache frequency was measured on a scale of 1-4. The dark bars indicate day 1 measurements and the hatched bard indicate day 28 measurements. FIG. 5A shows the parameters that are normally highly prevalent in fibromyalgia patients and FIG. 58 shows parameters that are more weakly prevalent in fibromyalgia patients with the exception of sleeplessness.

Libido (sex drive) was increased in response to testosterone treatment. Muscle pain, stiffness, fatigue upon awakening and tiredness were all decreased during testosterone treatment. For muscle pain, a defining symptom for fibromyalgia, 42% of patients had a greater than 50% improvement in fibromyalgia-related pain. Muscle pain VAS improvement was not dependent on whether the patient had previously had a clinical relationship with the study rheumatologist, and might therefore wish to please the doctor (data not shown).

These findings are consistent with the idea that restoration of premenopausal serum testosterone concentrations relieves symptoms that most specifically relate to testosterone deficiency, e.g., loss of sexual desire, loss of muscle function and increased fatigue. Indeed, patients reported decreased fibromyalgia-related muscle pain, decreased stiffness, decreased fatigue upon awakening, decreased tiredness, and increased libido. Blood tests and physical exam at the end of the study, including cardiac function, liver function and kidney function panel assessment, verified testosterone therapy did not adversely affect the general health of the study patient, and no study patient reported any adverse events that were attributable to the treatment.

Most trials involving hormone replacement therapy have used derivatives of hormones naturally found in women. These derivatized hormones have been promoted because of their patentability and their extended half life. Androgens are no exception since the androgen hormone most prescribed for women is methyltestosterone, where methylation at the C-17 position increases its oral bioavailability. Patients do not tolerate derivatized hormones very well, meaning that those hormones are not good candidates for commercialization. Non-derivatized exogenous hormones that are structurally identical to endogenous hormones have short plasma/serum half lives that range from 10-100 minutes, making oral administration of native hormones problematic. Investigators have begun to develop transdermal delivery systems, which provide sustained delivery while minimizing hepatotoxicity. A testosterone skin patch has been effective in HIV seropositive women with wasting syndrome (Miller, K. 1998. J. Clin. Endocrinol. Metab. 83:2717-2725; Javanbakht, M. 2000. J. Clin. Endocrinol. Metab. 85:2395-2401), but the skin patch causes topical skin irritation in about 30% of women, making its use problematic.

This example involves use of a testosterone formulated as a gel in a concentration that is appropriate for women. The data have shown this formulation to provide effective systemic delivery of testosterone in patients with fibromyalgia. 28 days of therapy with 0.75 g 1% (w/w) testosterone gel per day raised serum concentrations of total and free testosterone in fibromyalgia patients to concentrations approximating those in premenopausal women. At this dose, patients showed significantly decreased fibromyalgia-related muscle pain, decreased stiffness, decreased fatigue and increased libido in response to testosterone therapy. Fibromyalgia-related tender point pain was decreased, as well. These results, from both the pharmacokinetic and pain assessment standpoints, support the use of testosterone replacement therapy to treat individuals with fibromyalgia syndrome.

The following tables contain raw data from the study set forth above. For all these tables, the table patient numbering correlates with the Patient Study Identification Number as listed below. Patient Nos. 7 and 12 (010 and 016, respectively) are outliers with regard to their free testosterone level, and are taken into account as described in paragraph [0079].

| Testosterone B1 Level PK Data Patient ID Number | Study Patient ID Number |
|---|---|
| 1 | 009 |
| 2 | 005 |
| 3 | 007 |
| 4 | 001 |
| 6 | 002 |
| 7 | 010 |
| 8 | 011 |
| 9 | 012 |
| 10 | 017 |
| 11 | 006 |
| 12 | 016 |
| 13 | 018 |

| | | | | | | | | | |
|---|---|---|---|---|---|---|---|---|---|
| | | | | Prelim Q | | | | | |
| Pat ID# Form line-> | Group | interview date-sht 2a | reported Ht | reported Wt | calc'd BMI | FMS? | fatigued? | OV-? | if yes, dos |
| 001 | 1 | | 66 | 155 | 25.1 | 1 | 1 | 0 | |
| 002 | 2 | | 62 | 139 | 25.9 | 1 | 1 | [1] | OV-sheet 3 |
| 005 | 1 | Nov. 9, 2001 | 64 | 150 | 26.0 | 1 | 1 | 0 | |
| 006 | 3 | | 60 | 130 | 25.5 | 1 | 1 | 0 | |
| 007 | 1 | | 62 | 160 | 29.3 | 1 | 1 | 1 | March 1988 |
| 009 | 1 | Oct. 30, 2001 | 67 | 160 | 25.1 | 1 | 1 | 0 | |
| 010 | 2 | Nov. 29, 2001 | 67 | 175 | 27.5 | 1 | 1 | 1 | 1993 |
| 011 | 2 | Dec. 13, 2001 | 62 | 135 | 24.8 | 1 | 1 | 1 | 1981 |
| 012 | 2 | | 62 | 122 | 22.4 | 1 | 1 | 0 | |
| 016 | 3 | | 64 | 140 | 24.3 | 1 | 1 | 0 | |

-continued

| | | | Prelim Q | | | | | |
|---|---|---|---|---|---|---|---|---|
| 017 | 3 | | 62 | 140 | 25.7 | 1 | 1 | 0 |
| 018 | 3 | | 64 | 130 | 22.4 | 1 | 1 | 0 |
| | | | # inches | # field #lbs | cal'd <=30 | 1 = yes 0 = no | 1 = yes 0 = no | 1 = yes 0 = no date field |
| | | | | | | ph II must be fatigued AND have pain | | |

| Pat ID# Form line-> | Group | HRT? | if yes hormones? | willing To discont? | last period | vag bleeding? |
|---|---|---|---|---|---|---|
| 001 | 1 | 0 | | 1 | 1998 | |
| 002 | 2 | | | | | |
| 005 | 1 | 1 | premarin | 0 | | |
| 006 | 3 | 0 | | | | |
| 007 | 1 | 0 | | | Feb. 1, 1988 | |
| 009 | 1 | 1 | estrogen | 1 | 20 yrs | |
| 010 | 2 | 1 | estradiol patch | 1 | | |
| 011 | 2 | 0 | | | | |
| 012 | 2 | 0 | | | May 1, 1992 | |
| 016 | 3 | 0 | | | Feb. 1, 2002 | |
| 017 | 3 | 0 | | | Mar. 31, 2002 | |
| 018 | 3 | 1 | testosterone | 1 | now | |
| | | 1 = yes 0 = no HRT = hormone repl ther | text field | 1 = yes 0 = no | date field ph II MUST DISCONT HRT, antidep | 1 = yes 0 = no |

| ID Study | smoke? | # cig/day? | alcohol? | # drinks/d | med issues? | Specify | skin disease? | do you take StJohn's wort? | willing to exercise? |
|---|---|---|---|---|---|---|---|---|---|
| 001 | 0 | | 0 | | 0 | | 0 | 0 | 1 |
| 002 | | | | | | | | | |
| 005 | 0 | | 1 | occasionally | 0 | | 0 | 0 | 0 |
| 006 | 0 | | 0 | | 1 | zinc,tiazac for HTN | 0 | 0 | 1 |
| 007 | 0 | | 1 | 1x wine/wk | 1 | incr BP | 0 | 0 | 1 |
| 009 | 0 | | 1 | occasionally | 0 | BP 124/60 | 0 | 0 | 1 |
| 010 | 0 | | 0 | | 0 | | 0 | 1 | 1 |
| 011 | 0 | | 0 | | 0 | | 0 | 0 | 1 |
| 012 | 0 | | 1 | 4x wine/wk | 0 | | 0 | 0 | 1 |
| 016 | 0 | | 1 | occasionally | 0 | | 0 | 0 | 1 |
| 017 | 0 | | 0 | | 0 | | 0 | 0 | 1 |
| 018 | 0 | | 0 | | 0 | | 0 | 0 | 1 |
| | 1 = yes 0 = no | # field | 1 = yes 0 = no | # field | 1 = yes 0 = no | text | 1 = yes 0 = no | 1 = yes 0 = no | 1 = yes 0 = no |

Ph II MUST?

PatientQ & Stats

| | | | | | | | wt lbs reported | | ht inches reported | | BMI calc'd | | BP meas'd | | wt lbs meas'd | |
|---|---|---|---|---|---|---|---|---|---|---|---|---|---|---|---|---|
| Pat ID# Form line | Group | interview date d0 | d28 | dob 1 | age 2 | | d0 3 | d28 3 | d0 4 | d28 4 | d0 | d28 | d0 | d28 | d0 | d28 |
| 001 | 1 | not dated | Dec. 13, 2001 | Nov. 20, 1946 | 54 | | 155 | 165 | 66 | 66 | 25.1 | 26.7 | | 110/68 | | |
| 002 | 2 | Feb. 7, 2002 | Mar. 9, 2002 | Sep. 23, 1947 | 54 | | 139 | blank | 62 | blank | 25.5 | | blank | 120/76 | | |
| 005 | 1 | Nov. 9, 2001 | Dec. 13, 2001 | Aug. 15, 1950 | 51 | | 150 | 170 | 64 | 64 | 26.0 | 29.4 | 112/86 | 140/72 | | 162 |
| 006 | 3 | Mar. 23, 2002 | Apr. 20, 2002 | Nov. 6, 1948 | 53 | | 135 | 133 | 61 | 60 | 25.6 | 26.0 | | | | |
| 007 | 1 | Nov. 9, 2001 | Dec. 13, 2001 | Nov. 29, 1946 | 54 | | 160 | 171 | 62 | 62 | 29.3 | 31.4 | 144/86 | 138/68 | 168 | 171 |
| 009 | 1 | Nov. 5, 2001 | Dec. 13, 2001 | Mar. 30, 1948 | 53 | | 160 | 175 | 67 | 67 | 25.1 | 27.5 | 128/72 | 156/76 | 173 | |
| 010 | 2 | Feb. 6, 2002 | Mar. 9, 2002 | Dec. 30, 1956 | 45 | | 196 | 184 | 67 | 57 | 30.8 | 39.9 | 120/80 | 110/70 | | |
| 011 | 2 | Feb. 5, 2002 | Mar. 12, 2002 | Oct. 29, 1951 | 50 | | 135 | 136 | 62 | | 24.8 | | | 84/40 | | |
| 012 | 2 | Feb. 5, 2002 | Mar. 12, 2002 | Jul. 24, 1947 | 54 | | 120 | 120 | 62 | 62 | 22.0 | 22.0 | 110/70 | 110/60 | | |

-continued

| | | | | | | | wt lbs reported | | ht inches reported | | BMI | | BP | | wt lbs | |
|---|---|---|---|---|---|---|---|---|---|---|---|---|---|---|---|---|
| Pat ID# | | interview date | | dob | | age | d0 | d28 | d0 | d28 | calc'd | | meas'd | | meas'd | |
| Form line | Group | d0 | d28 | 1 | | 2 | 3 | 3 | 4 | 4 | d0 | d28 | d0 | d28 | d0 | d28 |
| 016 | 3 | Mar. 23, 2002 | Apr. 20, 2002 | Aug. 23, 2002 | | 55 | 140 | | 64 | | 24.3 | | | | | |
| 017 | 3 | Mar. 23, 2002 | Apr. 20, 2002 | Apr. 2, 1956 | | 45 | 142 | blank | 62 | blank | 26.0 | | | | | |
| 018 | 3 | Mar. 28, 2002 | Apr. 29, 2002 | Sep. 24, 1959 | | 42 | 126 | blank | 64 | blank | 21.7 | | | | | |
| type of field | | | | | | | | | | | | | | | Ph II MUST | |
| | | Nov. 5, 2001 | Apr. 29, 2002 | beginning to end-of-interview dates = | | | | | | | | | | | | |
| | | | | 6 mo duration but Lin Brown was unavailable during part of that time | | | | | | | | | | | | |
| | grp 1 | Nov. 5, 2001 | Dec. 13, 2001 | | | | | | | | | | | | | |
| | grp 2 | Feb. 5, 2002 | Mar. 12, 2002 | | | | | | | | | | | | | |
| | grp 3 | Mar. 23, 2002 | Apr. 29, 2002 | | | | | | | | | | | | | | about 4 months total not including 2 months break between groups 1 and 2, 3
INTERVIEW DATES FOR ALL SUBJECTS Nov. 5, 2001-Apr. 29, 2002 (see tab 2a "PatientQ & stats")
Feb. 15, 2002 BNT meeting at DMS where data were shown (must have been only grp 1)

GYNECOLOGICAL HISTORY

| ID | still menstr? d0 5A | last period? d0 5B | on HRT? d0 5C1 | what hormones? d0 5C1a | any DHEA past month? d0 5C1b | #tot preg? d0 5D | #live births? d0 5E |
|---|---|---|---|---|---|---|---|
| 001 | 2 | 1996 | 0 | none reported | 0 | 2 | 2 |
| 002 | 2 | 1974 | 1 | premarin | 0 | 3 | 3 |
| 005 | 2 | empty | 1 | premarin, stopped 3d before study | 0 | 2 | 2 |
| 006 | 2 | November 2000 | 0 | blank | blank | 2 | 2 |
| 007 | 2 | March 1988 | 0 | | 0 | 0 | 0 |
| 009 | 2 | NA hyst '86 | 1 | estrogen, stopped Nov. 5, 2001 | 0 | 3 | 3 |
| 010 | 2 | Jan. 12, 1997 | 1 | climara | 0 | 3 | 3 |
| 011 | 2 | 26 years ago | 0 | | 0 | blank | 0 |
| 012 | 2 | Jun. 4, 1992 | 0 | none reported | 0 | 2 | 2 |
| 016 | 1 | Jan. 30, 2002 | 0 | none reported | 0 | 2 | 2 |
| 017 | 1 | Mar. 17, 2002 | 0 | none reported | 0 | 3 | 1 |
| 018 | 1 | Mar. 4, 2002 | 1 | T reported | 0 | 3 | 2 |
| | 1 = pre | date field | 1 = yes | text field | 1 = yes | # field | # field |
| | 2 = post 1 yr | | 0 = no | | 0 = no | | |

| | phytoester? | | grape fr? # per wk | | libido sex drive? | | drive/joy | | GENERAL HEALTH Exercise exercise? | | wts? | | stength' g? | | cardiovas? | | #days/wk? | | #min/session? | | # mo in past |
|---|---|---|---|---|---|---|---|---|---|---|---|---|---|---|---|---|---|---|---|---|---|
| | d0 | d28 | d0 | d28 | d0 | d28 | d0 | d28 | d0 | d28 | d0 | d28 | d0 | d28 | d0 | d28 | d0 | d28 | d0 | d28 | d28 |
| ID | 6 A | | 6 B | | 6 Ci | | 6 Cii | | 6 Di1 | | 6 Da1 | | 6 Da2 | | 6 Da3 | | 6 Db | | 6 Dc | | |
| 001 | 1 | 1 | 0 | 0 | 1 | 2 | 7 | 7 | 0 | 1 | 0 | 0 | 1 | 1 | 0 | 1 | 2 | 7 | 60 | >20 | more consistent this month |
| 002 | 0 | 0 | 2 | 0 | 5 | 8 | 10 | 9.5 | 0 | 1 | 0 | 0 | 0 | 0 | 0 | 1 | 2 | 3 | 60 | 20-60 | 3 |
| 005 | 0 | 0 | 0 | 0 | 0 | 8 | 10 | 10 | 0 | 1 | 0 | 0 | 0 | 1 | 0 | 1 | 0 | 6 to 7 | | >20 | 1 mo |
| 006 | 1 | 0 | 0-1 | 0 | 1 | 4 | 5 | 5 | 0 | 1 | 0 | 1 | 0 | 1 | 0 | 1 | 1 to 2 | 3 to 4 | 45 | 20 to 45 | 6 |
| 007 | 0 | 0 | 0 | 0 | 5 | 7.5 | 9 | 9 | 0 | 1 | 0 | 0 | 0 | 1 | 1 | 1 | | 7 | 12.5 | >20 | 1 mo |
| 009 | 0 | 0 | 4 | 10/4 wk | 5 | 8 | 3 | 8 | 1 | 1 | 0 | 0 | 1 | 1 | 1 | 1 | 5 | 7 | | 20 | 1 |
| 010 | 0 | 1, two garden burgers | 0-1 | 2 to 3 | 3 | 6 | 6 | 7 | 0 | 1 | 0 | 0 | 0 | 1 | 0 | 1 | 0 | 7 | 0 | 30 to 60 | 0 |
| 011 | 0 | 0 | 0 | 0 | 0 | 0 | 8 | 10 | 0 | 1 | 0 | 0 | 0 | 1 | 0 | 1 | 0 | 7 | 0 | 20 | 1 |
| 012 | 0 | 1 | 1 | 1 | 2 | 3 | 9 | 9 | 1 | 1 | 0 | 0 | 0 | 1 | 1 | 1 | 5 | 5 | 20-30 | 25-30 | 15+ yrs |
| 016 | blank | no | 1 | 0 | 0 | 1 | 8 | 8 | 0 | 1 | 0 | 0 | 0 | 0 | 1 | 1 | | 5 | 30 | >20 | 1 mo |
| 017 | 0 | 0 | 0 | 0 | 5 | 6 | 6 | 6 | 1 | 1 | 0 | 0 | 0 | 0 | 1 | 1 | 4 | 4 to 5 | 20 | 20 | many |
| 018 | 0 | 0 | 6 | 0 | 0 | 5 | 4 to 5 | 6.5 | 1 | 1 | 1 | 1 | 1 | 1 | 1 | 1 | >5 | 6 | about 30 mins | >45 | >15 yrs |
| | 1 = yes 0 = no | | # field | | # scale 0 = low 10 = high | | # scale 0 = low 10 = high | | 1 = yes 0 = no | | 1 = yes 0 = no | | 1 = yes 0 = no | | 1 = yes 0 = no | | # field | | # field | | |
| | | | | AVE | 2.3 | 4.9 | 7.4 | 7.9 | | | | | | | | | | | | | |
| | | | | STD EV | 2.2 | 2.9 | 2.2 | 1.6 | | | | | | | | | | | | | |
| | | | | SEM | 0.6 | 0.8 | 0.6 | 0.5 | | | | | | | | | | | | | |
| | | | | TTEST 2-tailed paired | 0.0016 | | 0.1842 | | | | | | | | | | | | | | |

| | GENERAL HEALTH-Illness | | | | | | | | | | |
|---|---|---|---|---|---|---|---|---|---|---|---|
| | chronic probs? d0 6E | d28 | Illness 1 d0 6E | since when? d0 | Illness 2 d0 6E2 | since when? d0 6E2 | | Illness 1 d28 | since when? d28 | Illness 2 d28 | since when? d28 |
| 001 | 0 | 1 | glaucoma | no answer | blank | | | glaucoma | as before | blank | blank |
| 002 | 1 | 1 | Fast Pulse | 1999 | acid reflux | 2000 | | Irritable bowel | | aterial flutter | 2000 |
| 005 | 1 | 1 | GERD | 1986 | osteoarthritis | 2001 | | GERD | 1986 | osteoarthritis | 2001 |
| 006 | 1 | 1 | Hyper-tension | May 1979 | High Cholesterol | 1984 | Allergies since 1996, Chronic fatigue syndrome & immune dysfunction by March 1987 | Hypertension | May 1979 | High Cholesterol | 1984 |
| 007 | 1 | 1 | R leg/footpain | July 1997 | blank | | | R foot and leg pain | July 1997 | blank | blank |
| 009 | 1 | 1 | lower back | April 1996 | blank | | | lower back, R leg pain | April 1996 | arthritis both hands | 93 |
| 010 | 0 | 0 | blank | | blank | | | blank | | blank | |
| 011 | 0 | 1 | blank | blank | blank | | | no stomach | 1995 | Hip | 1995 |
| 012 | 0 | 0 | blank | blank | blank | | | | | | |
| 016 | 1 | 1 | bi-polar | February 1997 | | | | bi-polar | April 1973 | IBS | 1974, Sinusitus 2000 |
| 017 | 1 | 1 | Hypothyroid | November 1995 | blank | blank | | Hypothyroid | November 1995 | blank | blank |
| 018 | 0 | 0 | blank | blank | blank | blank | | blank | blank | blank | blank |
| | 1 = yes 0 = no | | text field | date field | | | | | | | |

| | | | | over/ctrd0 | | | | | meds? d28 6Fi | over/ctrd28 List1 d28 | #pills 1 d28 | List2 d28 | #pills 2 d28 | List3 d28 | #pills 3 d28 |
|---|---|---|---|---|---|---|---|---|---|---|---|---|---|---|---|
| ID | meds? d0 6F | List1 d0 6F1 | #pills 1 d0 6F1 | List 2 d0 | #pills 2 d0 6F2 | List3 d0 | #pills 3 d0 | | | | | | | | |

GENERAL HEALTH—over/counter meds

| ID | meds? d0 6F | List1 d0 | #pills 1 d0 6F1 | List 2 d0 | #pills 2 d0 6F2 | List3 d0 | #pills 3 d0 | meds? d28 6Fi | List1 d28 | #pills 1 d28 | List2 d28 | #pills 2 d28 | List3 d28 | #pills 3 d28 |
|---|---|---|---|---|---|---|---|---|---|---|---|---|---|---|
| 001 | 1 | ibuprofen | 4.5/d | | | | | 1 | ibuprofen 200 mg | 6 to 8/day | blank | | blank | |
| 002 | 1 | motrin IB | 1 to 2/d not always | | | | | 1 | motrin IB | 1-2/day, depending | | | | |
| 005 | 1 | advil | 6/wk | Aceta-minophen | 4/wk | ASA 325 mg qd1 | 1/d | 1 | Advil 200 mg | none | acetaminophen 355 mg? | one month | ASA 325 mg | one daily |
| 006 | 1 | advil | 2 to 4/wk | aleve | 1-2/wk | | | 1 | advil | 2 to 4/wk | aleve | 1-2/wk | | |
| 007 | 1 | motrin IB | 2/wk | | | | | 1 | Motrin IB | 4/day | blank | 0 | blank | |
| 009 | 1 | advil | 3/d | Zantec | no entry | | | 1 | advil | 4.5 | zantec | | vicodin (leg pain) | 1.5 |
| 010 | 0 | Cortizone cr PRN, Olocon cr 0.1% PRN, ginger rt PRN stomach aches, Vioxx 50/d Stopped for study: St. John's Wort 300 mg 3/d Ginko 400 mg 2-3/d, Gotu Kola 450 mg 3/d, Ginsing 900 mg 3/d, Zinc 100 mg/d, Primrose oil 1000 mg 2-3/d, Garlic 600 mg 3/d | | | | | | 1 | Vit E B C A/D, Ca; herbal Ginsing 900 mg 3/d, zinc 100 mg/d, primrose oil for only a few days 1000 mg 2-3/d | | | | | |
| 011 | 0 | hydroco | 8/day | Amitri-ptyline | 2/day | Xanflex | 5/day | 0 | hydroco | 8/day | Amitriptyline | 2/day | Xanflex | 5/day |
| 012 | 0 | | | | | | | 0 | | | | | | |
| 016 | 0 | Effexor xr | 3 pills/day | ginger root Tablets | 1 pills/day | Clona-zapam | 3 pills/day | 0 | blank | blank | blank | blank | blank | blank |
| 017 | 0 | 0 | blank | blank | blank | blank | blank | 0 | blank | blank | blank | blank | blank | blank |
| 018 | 0 | blank | blank | blank | blank | blank | blank | 1 = yes 0 = no | blank text field | blank # pills/day ginger root trazodone oral antidepressant inhibits the reuptake of serotonin anxiolytic | blank text field | blank # pills/day | blank text field | blank # pills/day |
| 1 = yes 0 = no | | text field | # pills/day | text field | # pills/day | | | | | | | | | |

| | FMS SYMPTOMS OVER LAST WEEK | | | | | | | | | | | |
|---|---|---|---|---|---|---|---|---|---|---|---|---|
| | muscle pain | | tiredness (fatigue) | | headache severity | | headache how often? | | stiffness | | sleeplessness optimal #hrs | |
| ID | d0 7A | d28 | d0 7B | d28 | d0 7C | d28 | d0 7C1-4 | d28 | d0 7D | d28 | d0 7Ei | d28 |
| 001 | 5 | 4 | 5 | 4 | 0 | 7 | 2 | 2 | 4 | 3 | 9.5 | 10.0 |
| 002 | 8 | 4 | 6 | 5 | 3.5 | 3 | 3 | 3 | 6 | 4 | 8.5 | 8.5 |
| 005 | 10 | 1.5 | 8 | 2 | 10 | 3 | 2 | 2 | 10 | 3 | 8.5 | 8.0 |
| 006 | 5 | 4 | 5 | 4 | 3 | 1 | 3 | 2 | 7 | 8 | 8.5 | 8.5 |
| 007 | 6 | 6.5 | 6 | 7 | 0 | 6 | 2 | 2 | 3 | 5 | 10.0 | 10.0 |
| 009 | 10 | 6 | 8 | 6 | 10 | 5 | 3 | 3 | 8 | 6 | 8.0 | 10.0 |
| 010 | 7 | 1 | 5 | 2 | 3 | 0 | blank | 2 | 7 | 1 | 6.5 | 7.0 |
| 011 | 10 | 0 | 10 | 0 | 3 | 0 | 2 | 2 | 10 | 0 | 2.5 | 3.0 |
| 012 | 6 | 6 | 8 | 8 | 3 | 8 | 3 | 3 | 8 | 6 | 6.0 | 6.0 |
| 016 | 6 | 6 | 7 | 4 | 4 | 8 | 3 | 3 | 6 | 7 | 9.0 | 8.0 |
| 017 | 7 | 5 | 6 | 7 | 1 | 2 | 2 | 2 | 8 | 5 | 9.0 | 9.0 |
| 018 | 6 | 4.5 | 8.5 | 4.5 | 0 | 0 | 1 | 1 | 6 | 5.5 | 6.0 | 6.5 |
| | # scale 0 = low 10 = high | | # scale 0 = none 10 = very | | # scale 0 = none 10 = severe | | 1 = never 2 = seldom 3 = often 4 = always | | # scale 0 = none 10 = very | | # field # hrs 10 = high | |
| AVE | 7.2 | 4.0 | 6.9 | 4.5 | 3.4 | 3.6 | 2.4 | 2.3 | 6.9 | 4.5 | 7.7 | 7.9 |
| STDEV | 1.9 | 2.1 | 1.6 | 2.3 | 3.4 | 3.1 | 0.7 | 0.6 | 2.1 | 2.4 | 2.1 | 2.0 |
| SEM | 0.5 | 0.6 | 0.5 | 0.7 | 1.0 | 0.9 | 0.2 | 0.2 | 0.6 | 0.7 | 0.6 | 0.6 |
| TTEST 2-tailed paired | 0.0096 * | | 0.0222 * | | 0.8755 | | 0.3409 | | 0.0364 | | 0.3388 | |

| | tired upon awakening (awoke rested?) | | anxiety? | | depressed? | | other symptoms? in past wk | |
|---|---|---|---|---|---|---|---|---|
| ID | d0 7Eii | d28 | d0 7F | d28 | d0 7G | d28 | d0 | d28 7H |
| 001 | 4 | 4 | 2 | 2 | 2 | 3 | none reported | 2 headaches- unusual, had normal bowel movements which is not her norm |
| 002 | 7 | 4 | 2 | 9 | 2.5 | 7 | much more pain and muscle spasms since going back to work, especially in neck and shoulder area | blank |
| 005 | 5 | 3 | 5 | 2 | 3 | 1 | upset stomach | breast very tender, breast size grew 2½", increased craving for sweets, wt gain |
| 006 | 9 | 9 | 7 | 4 | 3 | 2 | none reported | none reported |
| 007 | 10 | 5 | 2 | 0 | 2 | 0 | none reported | increased headaches during one month on meds |
| 009 | 10 | 5 | 8 | 5 | 8 | 4 | anxiety | achey & stiff in morning |
| 010 | 6 | 3 | 8 | 2 | 4 | 1 | none reported | none reported |
| 011 | 10 | 7 | 10 | 4 | 10 | 7 | none reported | none reported |
| 012 | 4 | 6 | 7 | 7 | 0 | 0 | none reported | none reported |
| 016 | 7 | 8 | 9 | 8 | 3 | 2 | Light headedness, Oncoming period | High Level of stress, crying to almost hyper- ventilating on a couple of occasions |
| 017 | 8 | 7 | 7 | 6 | 6 | 6 | My thyroid has has been acting up: Tender to the touch, difficulty swallowing, | Brain fog |

-continued

FMS SYMPTOMS OVER LAST WEEK

| | | | | | | | hypothyroid symptoms recurring | |
|---|---|---|---|---|---|---|---|---|
| 018 | 10 | 3.5 | 0 | 0 | 1.5 | 2.5 | none reported | none reported |

| | # scale 0 = rested 10 = very tired | | # scale 0 = not tense 10 = very tense | | # scale 0 = not depr 10 = very depr | | text field | |
|---|---|---|---|---|---|---|---|---|
| AVE | 7.5 | 5.4 | 5.6 | 4.1 | 3.8 | 3.0 | | |
| STDEV | 2.4 | 2.0 | 3.3 | 3.0 | 2.9 | 2.5 | | |
| SEM | 0.7 | 0.6 | 0.9 | 0.9 | 0.8 | 0.7 | | |
| TTEST 2-tailed paired | 0.0167 * | | 0.1544 | | 0.2603 | | | |

9/12 responders
Resp = 75%
* = chosen for power calc by SFBC
25 patients required based on
primary endpoint of VAS for muscle pain
VAS scale data

WORK/EMPLOYMENT

| | % activity prior to FMS | | employed? | | #hrs/wk | | #d/wk felt good? | | #d/wk missed work? | | pain when did work? | |
|---|---|---|---|---|---|---|---|---|---|---|---|---|
| | d0 | d28 | d0 | d28 | employed? | | d0 | d28 | d0 | d28 | d0 | d28 |
| ID | 7I | | 7J | | d0 | d28 | 7J1 | | 7J2 | | 7J3 | |
| 001 | 50% | 50% | 0 | 0 | blank | 0 | 4 | 5 | blank | NA | 10 | NA |
| 002 | 90% | 95% | 1 | 1 | 40 | 40 | 2 | 3 | 0 | 0 | I don't allow | 3 |
| 005 | 0% | 100% | 1 | 1 | 40 | 38.5 | 1 | 7 | 0 | 0 | 10 | 0 |
| 006 | 20% | 40% | 1 | 1 | 25 | 20 | 0 | 4 | blank | blank | 5 | 6 |
| 007 | 90% | 100% | 1 | 1 | 40 | 40 | 4 | 5 | 0 | 0 | no ans | 0 |
| 009 | 25% | 50% | 0 | 0 | blank | blank | 0 | 0 | blank | blank | NA | 8 |
| 010 | 90% | 100% | 1 | 1 | 35 | 45 | blank | 7 | blank | blank | 3 | 0 |
| 011 | 1% | 56% | 1 | 1 | 20 | 25 | 1 | 3 | 3 | 0 | 10 | 3 |
| 012 | 35% | 60% | 1 | 1 | 1 | 1 | 2 | 3 | blank | blank | 8 | 7 |
| 016 | 40% | 40% | 0 | | blank | blank | 4 | | blank | | 8 | |
| 017 | 20% | 20% | 1 | 0 | 1.5 | 2 | 2 | 3 | blank | blank | can't sustai | 5 |
| 018 | 100% | 100% | 1 | 1 | 40 | 40 | 0 | 0 | 0 | not zer | 0 | 4 |

| | % field | | 1 = yes 0 = no | | #hrs field | | # field | | # field | | # scale 0 = no prob 10 = very difficult | |
|---|---|---|---|---|---|---|---|---|---|---|---|---|
| AVE | 0.5 | 0.7 | | | 26.9 | 25.2 | 1.8 | 3.6 | 0.6 | 0.0 | 6.8 | 3.6 |
| STDEV | 0.4 | 0.3 | | | 16.3 | 18.3 | 1.6 | 2.3 | 1.3 | 0.0 | 3.7 | 3.0 |
| SEM | 0.1 | 0.1 | | | 4.7 | 5.3 | 0.5 | 0.7 | 0.4 | 0.0 | 1.1 | 0.9 |
| TTEST 2-tailed paired | 0.0333 | | McNemar test p = 0.32 | | 0.4989 | | 0.0192 | | 0.3910 | | 0.2617 | |

| | | | | | | | d28 no | | d28 yes | |
|---|---|---|---|---|---|---|---|---|---|---|
| | | d0 | | | no | | 2 | | 0 | |
| | | d0 | | | yes | | 1 | | 8 | |
| | | | | | | not sign if | | | | |

GENERAL HEALTH-over/counter meds d0

| ID # | List 1 | # pills 1 | List 2 | # pills 2 | List 3 | # pills 3 |
|---|---|---|---|---|---|---|
| 001 | Ibuprofen | 4.5/d | | | | |
| 002 | Motrin IB | 0 to 2/d | | | | |
| 005 | Advil | 6/wk | Acetaminophen | 4/wk | ASA 325 mg qdl | 1/d |
| 006 | Advil | 2 to 4/wk | Aleve | 1-2/wk | | |
| 007 | Motrin IB | 2/wk | | | | |

-continued

| ID # | List 1 | # pills 1 | List 2 | # pills 2 | List 3 | # pills 3 |
|---|---|---|---|---|---|---|
| | | | GENERAL HEALTH-over/counter meds d0 | | | |
| 009 | Advil | 3/d | Zantec | | no entry | |
| 010 | Cortizone cr PRN, O bcon cr 0.1% PRN, ginger rt PRN stomachaches, Vioxx 50/d; Stopped for study: St. John's Wort 300 mg 3/d, Ginko 440 mg 2-3/d, Gotu Kola 450 mg 3/d, Ginsing 900 mg 3/d, Zinc 100 mg/d, Primrose oil 1000 mg 2-3/d, Garlic 600 mg 3/d | | | | | |
| 011 | hydroco | 8/day | Amitriptyline | 2/day | Xanflex | 5/day |
| 012 | | | | | | |
| 016 | Effexor xr | 3 pills/day | ginger rt Tab | 1 pills/day | Clonazepam | 3 pills/day |
| 017 | no entry | blank | blank | blank | blank | blank |
| 018 | blank | blank | blank | blank | blank | blank |

| Patient ID # | GENERAL HEALTH - non-over/counter meds d28 meds? | |
|---|---|---|
| 001 | 1 | amitriptyline, nasalcrom, E 285 IU, Centrum (vit), carotenoid complex, B complex, glucosamine, magnesium/Ca, formula 4 enzymes lipids sterols, glaucoma opthalmics |
| 002 | 0 | |
| 005 | 1 | ?celebrex daily Tiazac 240 mg, Ziac 5/6.25, Lipitor, 40 Mg, Semprex-D 60 Mg, Atrovent Nasal Spray, Paxil 20 Mg, Synthroid, 50 |
| 006 | 1 | Mg, Nexiun, Centrum Silver, Vitamin C, 250 Mg, Vitamin E, 400 iu, Caltrate & soy |
| 007 | 1 | Multivits occas |
| 009 | 1 | protein drinks |
| 010 | 1 | Trazodone 150 mg/d, Zyrtec 10 mg/d, Valtrex 1 g/d, Wellbutrin |
| | | sr 150 mg 2/d, Albuterol 90 ug as needed hydrocodone 2q4h (10/500 mg), Amitriptyline 200 mg qhs (200 mg qhs), Zanflex 5 tabs/d (4 mg), Orycontin |
| 011 | 0 | 2q8h (40 mg) |
| 012 | 1 | Trazodone (for sleep), calcium, mutivitamin |
| 016 | 1 | Prilosec, Effexor xR, Trazodone, Clonazepam, Levsin, Relefen |
| 017 | 1 | multi Vitamin-mineral: 1/day, Balanced B-100: 1/day, Vit E 400 IU: 1/day, Vit C 250 mg: 1/day. Primadophilus-Bilidus 290 mg: 1/day |
| 018 | 0 | Blank |

| Pat ID # | Group | BL date d0 | Phys Exam date | BL Date d29 | TT pre | TT d29 | CHOLEST d29 | | HDL d29 | | LDL d29 | | TRIG d29 | |
|---|---|---|---|---|---|---|---|---|---|---|---|---|---|---|
| | | | | | incl criteria | | | | | | | | | |
| | | | | | <=0.4 | <=N | normal range | | normal range | | normal range | | <=300 mg/L | |
| | | | | | TT | TT | lipid normal values | lipid | lipid | lipid | lipid | lipid | lipid | lipid |
| | | | | | 0.1-0.8 ng/ml | <240 mg/dL | >35-95 mg/dL | | <80-210 mg/dL | | 10-190 mg/dL | | | |
| 001 | 1 | Oct. 2, 2001 | Nov. 7, 2001 | Dec. 8, 2001 | 0.21 | | 151 | 142 | 64 | 62 | 66 | 62 | 103 | 88 |
| 002 | 2 | Feb. 7, 2002 | Oct. 4, 2001 | Mar. 9, 2002 | 0.23 | | 188 | 173 | 58 | 53 | 93 | 106 | 184 | 71 |
| 005 | 1 | Oct. 2, 2001 | Nov. 9, 2001 | Dec. 8, 2001 | 0.31 | | 228 | 278 | 86 | 76 | 112 | 171 | 151 | 153 |
| 006 | 3 | Mar. 23, 2002 | Mar. 23, 2002 | Apr. 20, 2002 | 0.11 | | 294 | 225 | 84 | 79 | 157 | 112 | 265 | 172 |
| 007 | 1 | Oct. 2, 2001 | Nov. 9, 2001 | Dec. 8, 2001 | 0.23 | | 255 | 221 | 67 | 58 | 170 | 143 | 90 | 101 |
| 009 | 1 | Nov. 1, 2001 | Nov. 5, 2001 | Dec. 8, 2001 | 0.27 | | 213 | 201 | 63 | 48 | 116 | 103 | 170 | 248 |
| 010 | 2 | Feb. 6, 2002 | Nov. 29, 2001 | Mar. 9, 2002 | 0.22 | | 207 | 150 | 66 | 56 | 113 | 82 | 140 | 59 |
| 011 | 2 | Feb. 5, 2002 | Dec. 13, 2001 | Mar. 12, 2002 | 0.09 | | 141 | 168 | 47 | 54 | 79 | 92 | 75 | 111 |
| 012 | 2 | Feb. 5, 2002 | Jan. 24, 2002 | Mar. 12, 2002 | 0.25 | | 201 | 185 | 63 | 58 | 123 | 115 | 77 | 60 |
| 016 | 3 | Mar. 23, 2002 | Mar. 23, 2002 | Apr. 20, 2002 | 0.28 | | 203 | 209 | 42 | 41 | 129 | 140 | 161 | 142 |
| 017 | 3 | Mar. 23, 2002 | Mar. 23, 2002 | Apr. 20, 2002 | 0.12 | | 228 | 208 | 67 | 52 | 131 | 124 | 152 | 161 |
| 018 | 3 | Mar. 28, 2002 | Mar. 28, 2002 | Apr. 29, 2002 | 0.33 | | 130 | 130 | 50 | 49 | 68 | 68 | 58 | 67 |

INTERVIEW DATES FOR ALL SUBJECTS Nov. 5, 2001-Apr. 29, 2002 (see tab 2a "PatentQ & stats")

| Study # | Reason ineligible/dropped out |
|---|---|
| 003 | Dexascan revealed osteoporosis, advised not to stop HRT |
| 004 | Not post menopausal per labs |
| 008 | Personal reasons |
| 013 | High testosterone level |
| 014 | Normal testosterone |
| 015 | High cholesterol, trriglycerides 2/18 not eligible due to T higher than cut off |

| | ALT $\leq$=1.5N | d29 | ALK P $\leq$=2xN | d29 | AST $\leq$=1.5N | d29 | ALB d29 normal range | | TB ili $\leq$=N | d29 | DB ili $\leq$=N | d29 |
|---|---|---|---|---|---|---|---|---|---|---|---|---|
| | Liver | Liver | Liver | Liver | Liver | Liver | Liver nrml values | Liver | Liver | Liver | Liver | Liver |
| ID | 0-40 U/L | | 40-120 U/L | | 10-30 U/L | | 3.2-5.2 g/dL | | 0.2-1.3 mg/dL | | 0.0-0.3 mg/dL | |
| 001 | 23 | 19 | 72 | 83 | 18 | 20 | 4.0 | 4.1 | 0.3 | 0.4 | 0.1 | 0.1 |
| 002 | 10 | 34 | 72 | 76 | 12 | 24 | 3.3 | 3.9 | 0.3 | 0.3 | 0.1 | 0.1 |
| 005 | 8 | 18 | 72 | 65 | 15 | 22 | 4.0 | 4.1 | 0.2 | 0.3 | 0.1 | 0.1 |
| 006 | 44 | 34 | 194 | 156 | 41 | 44 | 4.2 | 4.2 | 0.4 | 0.5 | 0.1 | 0.1 |
| 007 | 20 | 20 | 56 | 53 | 24 | 23 | 4.2 | 4.1 | 0.3 | 0.3 | 0.1 | 0.0 |
| 009 | 20 | 30 | 97 | 94 | 27 | 26 | 3.9 | 3.9 | 0.3 | 0.3 | 0.1 | 0.1 |
| 010 | 31 | 18 | 72 | 70 | 33 | 29 | 4.1 | 4.3 | 0.3 | 0.4 | 0.1 | 0.1 |
| 011 | 11 | 8 | 103 | 89 | 22 | 28 | 3.5 | 3.5 | 0.3 | 0.2 | 0.1 | 0.0 |
| 012 | 11 | 9 | 55 | 63 | 17 | 18 | 4.2 | 4.2 | 0.5 | 0.5 | 0.1 | 0.1 |
| 016 | 8 | 10 | 85 | 84 | 20 | 32 | 3.7 | 3.9 | 0.2 | 0.2 | 0.1 | 0.0 |
| 017 | 16 | 10 | 75 | 67 | 24 | 19 | 4.1 | 3.9 | 0.5 | 0.3 | 0.1 | 0.1 |
| 018 | 11 | 15 | 62 | 72 | 16 | 18 | 4.3 | 4.3 | 0.6 | 0.6 | 0.2 | 0.1 |

| ID | BUN $\leq$=2xN Kidney 8-18 mg/dL | d29 Kidney | CRE $\leq$=N Kidney 0.7-1.2 mg/dL | d29 Kidney | FSH* >=22 incl 5-20 pre <200 post IU/L | CBC HGB CBC 12-16 g/dL | d29 CBC | chr fatigue | difficult sleep? | WT | BP $\leq$=160/95 | comments |
|---|---|---|---|---|---|---|---|---|---|---|---|---|
| 001 | 13 | 14 | 0.8 | 0.7 | 118.6 | 13.1 | 13.3 | 1 | 1 | 165 | 110/68 | |
| 002 | 13 | 16 | 0.7 | 0.6 | Ov- | 12.0 | 11.9 | 1 | 0 | 120 | 110/60 | |
| 005 | 22 | 17 | 0.8 | 0.7 | hrt 40.1 | 13.0 | 12.8 | 1 | 0 | 169 | 140/72 | |
| 006 | 23 | 20 | 0.9 | 0.9 | 114.8 | 14.3 | 14.0 | 1 | Blank | 133 | | PM, LB: recom not accept, refer int med/gastroent; chgd crit |
| 007 | 18 | 19 | 0.7 | 0.8 | Ov- 44.1 | 13.3 | 13.4 | 0 | | 171 | 138/68 | |
| 009 | 16 | 17 | 0.8 | 0.7 | hrt 22.4 | 11.1 | 11.2 | | | 175 | 156/76 | |
| 010 | 11 | 18 | 0.8 | 0.8 | hrt Ov-32 | 11.3 | 12.1 | 1 | 1 | 184 | 110/70 | |
| 011 | 9 | 14 | 0.9 | 1.0 | Ov-N/A | 10.1 | 10.3 | 1 | 1 | 136 | 84/40 | |
| 012 | 14 | 15 | 0.7 | 0.7 | 98.3 | 13.8 | 13.5 | 1 | 1 | 120 | 110/60 | |
| 016 | 19 | 17 | 0.8 | 0.7 | N/A | 13.1 | 12.4 | 1 | 0 | 140 | | |
| 017 | 14 | 16 | 0.7 | 0.7 | N/A | 14.3 | 13.5 | 1 | 1 | 144-145 | | |
| 018 | 14 | 18 | 0.8 | 0.8 | N/A | 13.2 | 13.2 | 1 | 1 | 120 | | |

High BUN due to pre/post renal azotemia or dehydration or high protein diet
BUN/Crea ratios:
normal 10/1
dehydration 15-20/1
pre/postrenal >10/1
renal disease <10/1

*FSH
5-20 IU/L follicular phase
15-30 IU/L abrupt rise
5-15 IU/L luteal phase
up to 200 IU/L post menopausal
Inclusion if FSH >= 22 or willing to use adequate contraception
If no menses for 1 yr & on HRT
    don't test for FSH (will be low); physician counseling
    If Ov-dont test for FSH
pH II must get FSH test regardless
BSO = bilateralsalpingo-oophorectomy
TAH = total abdominal hysterectomy
002, had early menopause, had TAH/BSO at age 30
011, early menopause, comorbidities, alcohol abuse, long surgical hx, Ph IIMUST GET
1 = yes    1 = yes
0 = no    0 = no
note: CLR value on PhysQ

| Pat ID # | | interview dates | | widespread pain? | | 11/18 TP? | | ID | DOLORIMETER-> 11R | |
|---|---|---|---|---|---|---|---|---|---|---|
| Form line-> | Group | d0 | d28 | d0 | d28 | d0 | d28 | | d0 | d28 |
| | | | | | | | | | trap R | |
| 001 | 1 | Nov. 7, 2001 | Dec. 5, 2001 | 0 | 1 | 0 | 0 | 001 | blank | 9 |
| 002 | 2 | Feb. 7, 2002 | Mar. 9, 2002 | 1 | 1 | 1 | 1 | 002 | 4 | 6 |
| 005 | 1 | Nov. 9, 2001 | Dec. 7, 2001 | 1 | 0 | 1 | 0 | 005 | 6.5 | 7 |
| 006 | 3 | Mar. 23, 2002 | Apr. 20, 2002 | 1 | 0 | 1 | 0 | 006 | 4 | 3.5 |
| 007 | 1 | Nov. 9, 2001 | Dec. 5, 2001 | 1 | 1 | no input | 0 | 007 | 6 | 9 |
| 009 | 1 | Nov. 5, 2001 | Dec. 3, 2001 | no input | 1 | no input | 0 | 009 | 4 | blank |
| 010 | 2 | Feb. 6, 2002 | Mar. 9, 2002 | 1 | generally better | 1 | blank | 010 | 4.5 | 7.1 |

-continued

| | | | | | | | | | | |
|---|---|---|---|---|---|---|---|---|---|---|
| 011 | 2 | Feb. 5, 2002 | Mar. 12, 2002 | 1 | mild | 1 | blank | 011 | 2 | 4.5 |
| 012 | 2 | Feb. 5, 2002 | Feb. 12, 2002 | 1 | 1 | 1 (tender not painful) | (+/−) | 012 | 6 | 6.5 |
| 016 | 3 | | Apr. 20, 2002 | | no input | | no input | 016 | 3.5 | 5 |
| 017 | 3 | Mar. 23, 2002 | Apr. 20, 2002 | | no input | | 1 | 017 | 5 | 3.5 |
| 018 | 3 | Mar. 28, 2002 | Apr. 20, 2992 | 1 | no input | no input | 1 | 018 | 3.5 | 2 |
| | | | | 1 = yes 0 = no | 1 = yes 0 = no | 1 = yes 0 = no | 1 = yes 0 = no | | | Trapezius |
| | | | | | | | | | | trapezius at midpt of the upper border LB: "trap" on the top of the shoulder toward the back (flat triangular muscle posterior neck and shoulder) C |
| | | | AVE | 0.9 | 0.7 | 0.8 | 0.4 | AVE | 4.5 | 5.7 |
| | | | STDEV | 0.3 | 0.5 | 0.4 | 0.5 | STDEV | 1.3 | 2.3 |
| | | | SEM | 0.1 | 0.1 | 0.1 | 0.1 | SEM | 0.4 | 0.7 |
| | | | TTEST 2-tailed paired | 0.61 | | 0.18 | | TTEST 2-tailed paired | 0.12 | |

INTERVIEW DATES FOR ALL SUBJECTS Nov. 5, 2001-Apr. 29, 2002
(see tab 2a "PatientQ & stats")

| Pat ID # | DOLORIMETER-> | | range 2-9 | | | |
|---|---|---|---|---|---|---|
| | 12L | | 3R | | 4L | |
| Form line-> | d0 | d28 | d0 | d28 | d0 | d28 |
| | trap L | | 2nd ics R | | 2nd ics L | | TotD0 | Totd28 |

| | | | | | | |
|---|---|---|---|---|---|---|
| 001 | blank | 9 | blank | 6 | blank | 6 |
| 002 | 3.5 | 6 | 3.5 | 4.5 | 3 | 6 |
| 005 | 6 | 7 | 6 | 7 | 5.5 | 7 |
| 006 | 4 | 3 | 4 | 4 | 4 | 3.5 |
| 007 | 6 | 9 | 5 | 5.5 | 4 | 6 |
| 009 | 4 | blank | 4 | blank | 4 | blank |
| 010 | 3 | 6 | 3.5 | 7.1 | 3 | 4.5 |
| 011 | 2 | 4 | 3 | 3 | 2 | 3 |
| 012 | 7 | 6.5 | 6 | 4 | 4.5 | 4 |
| 016 | 4.5 | 3.5 | 3.5 | 5 | 4 | 4.5 |
| 017 | 4 | 3 | 4 | 3 | 4 | 2.5 |
| 018 | 3 | 2 | 3 | 2 | 2 | 2 |

Second rib
2nd costochondral
junction (rib-cartil)
LB: "2nd ics"
on the breast
bone
D

| | | | | | |
|---|---|---|---|---|---|
| 4.3 | 5.4 | 4.1 | 4.6 | 3.6 | 4.5 |
| 1.5 | 2.4 | 1.1 | 1.7 | 1.1 | 1.6 |
| 0.4 | 0.7 | 0.3 | 0.5 | 0.3 | 0.5 |
| 0.25 | | 0.49 | | 0.14 | |

| DOLORIMETER-> overall dolorimeter range 2-9 | | | | | | | | | | | | |
|---|---|---|---|---|---|---|---|---|---|---|---|---|
| 11R | | | 12L | | | 3R | | | 4L | | | |
| d0 | d28 | diff | d0 | d28 | diff | d0 | d28 | diff | d0 | d28 | diff | SUMMATION VALUES |
| trap R | | | trap L | | | 2nd ics R | | | 2nd ics L | | | d0 | d28 | diff d28-d0 |

| | | | | | | | | | | | | | | | |
|---|---|---|---|---|---|---|---|---|---|---|---|---|---|---|---|
| 001 | blank | 9.0 | | blank | 9.0 | | blank | 6.0 | | blank | 6.0 | | | 30.0 | |
| 002 | 4.0 | 6.0 | 2.0 | 3.5 | 6.0 | 2.5 | 3.5 | 4.5 | 1.0 | 3.0 | 6.0 | 3.0 | 14.0 | 22.5 | 8.5 |
| 005 | 6.5 | 7.0 | 0.5 | 6.0 | 7.0 | 1.0 | 6.0 | 7.0 | 1.0 | 5.5 | 7.0 | 1.5 | 24.0 | 28.0 | 4.0 |
| 006 | 4.0 | 3.5 | −0.5 | 4.0 | 3.0 | −1.0 | 4.0 | 4.0 | 0.0 | 4.0 | 3.5 | −0.5 | 16.0 | 14.0 | −2.0 |
| 007 | 6.0 | 9.0 | 3.0 | 6.0 | 9.0 | 3.0 | 5.0 | 5.5 | 0.5 | 4.0 | 6.0 | 2.0 | 21.0 | 29.5 | 8.5 |
| 009 | 4.0 | blank | | 4.0 | blank | | 4.0 | blank | | 4.0 | blank | | 16.0 | | |
| 010 | 4.5 | 7.1 | 2.6 | 3.0 | 6.0 | 3.0 | 3.5 | 7.1 | 3.6 | 3.0 | 4.5 | 1.5 | 14.0 | 24.7 | 10.7 |
| 011 | 2.0 | 4.5 | 2.5 | 2.0 | 4.0 | 2.0 | 3.0 | 3.0 | 0.0 | 2.0 | 3.0 | 1.0 | 9.0 | 14.5 | 5.5 |
| 012 | 6.0 | 6.5 | 0.5 | 7.0 | 6.5 | −0.5 | 6.0 | 4.0 | −2.0 | 4.5 | 4.0 | −0.5 | 23.5 | 21.0 | −2.5 |
| 016 | 3.5 | 5.0 | 1.5 | 4.5 | 3.5 | −1.0 | 3.5 | 5.0 | 1.5 | 4.0 | 4.5 | 0.5 | 15.5 | 18.0 | 2.5 |
| 017 | 5.0 | 3.5 | −1.5 | 4.0 | 3.0 | −1.0 | 4.0 | 3.0 | −1.0 | 4.0 | 2.5 | −1.5 | 17.0 | 12.0 | −5.0 |

-continued

| DOLORIMETER-> overall dolorimeter range 2-9 | | | | | | | | | | | | | |
|---|---|---|---|---|---|---|---|---|---|---|---|---|---|
| | 11R | | | 12L | | | 3R | | | 4L | | | |
| | d0 | d28 | diff | d0 | d28 | diff | d0 | d28 | diff | d0 | d28 | diff | SUMMATION VALUES |
| | trap R | | | trap L | | | 2nd ics R | | | 2nd ics L | | d0 d28 diff d28-d0 | |
| 018 | 3.5 | 2.0 | −1.5 | 3.0 | 2.0 | −1.0 | 3.0 | 2.0 | −1.0 | 2.0 | 2.0 | 0.0 | 11.5 8.0 −3.5 |
| AVERAGE of the change | | | 0.9 | | | | | | 0.4 | | | | 2.7 AVE |
| STDEV of the change | | | 1.7 | | | | | | 1.6 | | | | 5.7 STDEV |
| (change of d28 minus d0) | | | | | | | | | | | | | 1.8 SEM |
| therapy should raise | | | | | | Dolorimeter, | | | | | | | see below TTEST |
| the number | | | | | | use for | | | | | | | |
| i.e. raise the pain | | | | | | secondary | | | | | | 002 | 14.0 22.5 8.5 |
| threshold | | | | | | endpt values | | | | | | 005 | 24.0 28.0 4.0 |
| n = 10 | | | | | | | | | | | | 006 | 16.0 14.0 −2.0 |
| TTEST see above, | | | | | | | | | | | | 007 | 21.0 29.5 8.5 |
| same here | | | | | | | | | | | | 010 | 14.0 24.7 10.7 |
| | | | | | | | | | | | | 011 | 9.0 14.5 5.5 |
| | | | | | | | | | | | | 012 | 23.5 21.0 −2.5 |
| | | | | | | | | | | | | 016 | 15.5 18.0 2.5 |
| | | | | | | | | | | | | 017 | 17.0 12.0 −5.0 |
| | | | | | | | | | | | | 018 | 11.5 8.0 −3.5 |
| | | | | | | | | | | | | Dolorimeter: n = 10 | 0.17 TTEST |

| TENDER POINT VALUES | | | | | | | | | | | | | | | |
|---|---|---|---|---|---|---|---|---|---|---|---|---|---|---|---|
| | d0 | d28 | d0 | d28 | d0 | d28 | d0 | d28 | d0 | d28 | d0 | d28 | d0 | d28 | |
| ID | 1R | | 2L | | 3R | | 4L | | 5R | | 6L | | 7R | | 8L |
| 001 | 0 | 0 | 0 | 0 | 0 | 0 | 0 | 0 | 0 | 0 | 0 | 0 | 0 | 4 | 0 0 |
| 002 | 6 | 5 | 6 | 5 | 6 | 5 | 6 | 5 | 4 | 0 | 4 | 0 | 6 | 3 | 6 3 |
| 005 | 8 | 5 | 0 | 5 | 8 | 0 | 8 | 3 | 0 | 0 | 6 | 0 | 10 | 5 | 10 0 |
| 006 | 7 | 1 | 7 | 4 | 7 | 2 | 7 | 2 | 6 | 4 | 6 | 4 | 4 | 1 | 4 1 |
| 007 | 8 | 5 | 8 | 5 | 4 | 5 | 4 | 5 | 0 | 4 | 0 | 4 | 8 | 5 | 8 5 |
| 009 | 8 | 7 | 8 | 7.5 | 8 | 5 | 8 | 5 | 8 | 3 | 1 | 3 | 8 | 8.5 | 8 8 |
| 010 | 8 | 2 | 8 | 4 | 8 | 4 | 8 | 2 | 8 | 3 | 8 | 0.5 | 8 | 3.5 | 8 5 |
| 011 | 10 | 3 | 10 | 3 | 10 | 4 | 10 | 4 | 10 | 3 | 10 | 3 | 10 | 6 | 10 6 |
| 012 | 4 | 2 | 7 | 2 | 4 | 3 | 7 | 3 | 0 | 0 | 0 | 0 | 7 | 3 | 7 3 |
| 016 | 4 | 9 | 4 | 7 | 4 | 9 | 4 | 9 | 3 | 4 | 3 | 4 | 6 | 7 | 6 2 |
| 017 | 8 | 6 | 8 | 6 | 8 | 6 | 8 | 6 | 8 | 6 | 8 | 6 | 8 | 7 | 8 7 |
| 018 | 6 | 5 | 6 | 5 | 6 | 5 | 6 | 5 | 5 | 5 | 5 | 5 | 0 | 2 | 0 2 |

| | Cervical | Second rib | Lateral epicondyle | Gluteal |
|---|---|---|---|---|
| | lower cervical | 2nd costochondral | 2 cm distal to | upper outer quadrant |
| | paraspinals | junction (rib-cartil) | lateral epicondyle | of buttock (gluteal) |
| green = worse pain | | LB: "2nd ics" | in forearm | |
| 36/216 = 17% worse TPs | | blue = no change | | |
| on a per TP basis | | 25/216 = 12% no change on a per TP basis | | |
| | at the base | on the breast | on the outer edge of | on the outside |
| | of the neck | bone | the forearm about | of the hip |
| | in the back | | an inch below the | |
| (red = ave of patient reported range) | | | elbow | |
| black/red = improvement ~71% on a per TP basis | | | | |

| | 1 | | 2 | | 3 | | 4 | | 5 | | 6 | | 15 7 | 16 | 8 | |
|---|---|---|---|---|---|---|---|---|---|---|---|---|---|---|---|---|
| 2-tailed | B Cervical | | | | D Second rib | | | | E Lateral epicondyle | | | | H Gluteal | | | |
| paired | R | | L | | R | | L | | R | | L | | R | | L | |
| AVE | 6.4 | 4.2 | 6.0 | 4.5 | 6.1 | 4.0 | 6.3 | 4.1 | 4.3 | 3.1 | 4.3 | 2.5 | 6.3 | 4.6 | 6.3 | 3.5 |
| STDEV | 2.7 | 2.6 | 3.2 | 2.1 | 2.7 | 2.5 | 2.6 | 2.3 | 3.7 | 2.8 | 3.5 | 2.2 | 3.4 | 2.2 | 3.4 | 2.7 |
| SEM | 0.8 | 0.8 | 0.9 | 0.6 | 0.8 | 0.7 | 0.8 | 0.7 | 1.1 | 0.8 | 1.0 | 0.6 | 1.0 | 0.6 | 1.0 | 0.8 |
| TTEST (P value) | 0.03 | | 0.13 | | 0.06 | | 0.04 | | 0.27 | | 0.12 | | 0.07 | | 0.01 | |
| AVE d0 | 6.4 | | 6.0 | | 6.1 | | 6.3 | | 4.3 | | 4.3 | | 6.3 | | 6.3 | |
| AVE d0-d28 | 2.3 | | 1.5 | | 2.1 | | 2.3 | | 1.3 | | 1.8 | | 1.7 | | 2.8 | |

| | d0 | d28 | d0 | d28 | d0 | d28 | d0 | d28 | d0 | d28 | d0 | d28 |
|---|---|---|---|---|---|---|---|---|---|---|---|---|
| ID | 9R | | 10L | | 11R | | 12L | | 13R | | 14L | |
| 001 | 0 | 0 | 0 | 0 | 0 | 0 | 0 | 0 | 0 | 0 | 0 | 0 |
| 002 | 6 | 5 | 6 | 5 | 6 | 5 | 6 | 5 | 6 | 4 | 6 | 4 |
| 005 | 8 | 0 | 8 | 0 | 8 | 3 | 8 | 3 | 8 | 0 | 8 | 0 |

-continued

TENDER POINT VALUES

| 006 | 7  | 4 | 7  | 4 | 7  | 4 | 7  | 4 | 7  | 1 | 7  | 1 |
|-----|----|---|----|---|----|---|----|---|----|---|----|---|
| 007 | 9  | 6 | 9  | 4 | 1  | 6 | 1  | 6 | 3  | 5 | 3  | 5 |
| 009 | 8  | 5 | 8  | 5 | 8  | 5 | 8  | 5 | 1  | 5 | 1  | 5 |
| 010 | 8  | 4 | 8  | 4 | 8  | 1 | 8  | 1 | 8  | 4 | 8  | 4 |
| 011 | 10 | 3 | 10 | 3 | 10 | 6 | 10 | 6 | 10 | 6 | 10 | 6 |
| 012 | 0  | 2 | 0  | 2 | 5  | 2 | 5  | 2 | 5  | 2 | 5  | 2 |
| 016 | 4  | 9 | 4  | 3 | 4  | 9 | 4  | 9 | 4  | 9 | 4  | 3 |
| 017 | 8  | 6 | 8  | 6 | 8  | 6 | 8  | 6 | 8  | 7 | 8  | 7 |
| 018 | 7  | 6 | 7  | 6 | 8  | 4 | 8  | 4 | 8  | 4 | 8  | 4 |

| Occiput | Trapezius | Supraspinatus |
|---|---|---|
| suboccipital muscle insertions at occiput at the base of the skull beside the spinal col | trapezius at midpt of the upper border LB: "trap" on the top of the shoulder toward the back (flat triangular muscle posterior neck and shoulder) | supraspinatus at its origin above medial scapular spine over the shoulder blade |

| 2-tailed paired | 9<br>A Occiput<br>R | | 10<br><br>L | | 11<br>C Trapezius<br>R | | 12<br><br>L | | 13<br>F Supraspinatus<br>R | | 14<br><br>L | |
|---|---|---|---|---|---|---|---|---|---|---|---|---|
| AVE | 6.3 | 4.2 | 6.3 | 3.5 | 6.1 | 4.3 | 6.1 | 4.3 | 5.7 | 3.9 | 5.7 | 3.4 |
| STDEV | 3.3 | 2.6 | 3.3 | 2.0 | 3.1 | 2.5 | 3.1 | 2.5 | 3.1 | 2.8 | 3.1 | 2.3 |
| SEM | 0.9 | 0.8 | 0.9 | 0.6 | 0.9 | 0.7 | 0.9 | 0.7 | 0.9 | 0.8 | 0.9 | 0.7 |
| TTEST (P value) | 0.07 | | 0.01 | | 0.11 | | 0.11 | | 0.15 | | 0.04 | |
| AVE d0 | 6.3 | | 6.3 | | 6.1 | | 6.1 | | 5.7 | | 5.7 | |
| AVE d0-d28 | 2.1 | | 2.8 | | 1.8 | | 1.8 | | 1.8 | | 2.3 | |

| ID | d0<br>15R | d28 | d0<br>16L | d28 | d0<br>17R | d28 | d0<br>18L | d28 | Totd0<br>SUM | Totd28<br>SUM |
|---|---|---|---|---|---|---|---|---|---|---|
| 001 | 0  | 0 | 0  | 0 | 0  | 0 | 0   | 0 | 0     | 4   |
| 002 | 6  | 3 | 6  | 3 | 6  | 2 | 6   | 2 | 104   | 64  |
| 005 | 9  | 0 | 9  | 0 | 5  | 0 | 5   | 0 | 126   | 24  |
| 006 | 4  | 1 | 4  | 1 | 6  | 1 | 6   | 1 | 110   | 41  |
| 007 | 8  | 6 | 8  | 4 | 3  | 5 | 3   | 5 | 88    | 90  |
| 009 | 8  | 5 | 8  | 5 | 8  | 5 | 8   | 6 | 123   | 98  |
| 010 | 8  | 5 | 8  | 3 | 8  | 4 | 8   | 4 | 144   | 58  |
| 011 | 10 | 6 | 10 | 6 | 10 | 3 | 10  | 3 | 180   | 80  |
| 012 | 1  | 2 | 1  | 2 | 0  | 3 | 0.5 | 3 | 58.5  | 38  |
| 016 | 6  | 6 | 6  | 2 | 4  | 5 | 4   | 2 | 78    | 113 |
| 017 | 8  | 8 | 8  | 8 | 8  | 8 | 8   | 8 | 144   | 120 |
| 018 | 5  | 3 | 5  | 3 | 5  | 1 | 0   | 1 | 95    | 70  |

| Greater trochanter | Knee |
|---|---|
| greater trochanter at the top of the hip | knee just proximal to the medial joint line on the fat pad over the knee |

| 2-tailed paired | 7<br>15<br>G Greater trochanter<br>R | | 8<br>16<br><br>L | | 17<br>I Knee<br>R | | 18<br><br>L | | | |
|---|---|---|---|---|---|---|---|---|---|---|
| AVE | 6.1 | 3.8 | 6.1 | 3.1 | 5.3 | 3.1 | 4.9 | 2.9 | 104.2 | 66.7 |
| STDEV | 3.1 | 2.6 | 3.1 | 2.4 | 3.1 | 2.4 | 3.4 | 2.5 | 46.5 | 35.7 |
| SEM | 0.9 | 0.8 | 0.9 | 0.7 | 0.9 | 0.7 | 1.0 | 0.7 | 13.4 | 10.3 |
| TTEST (P value) | 0.01 | | 0.002 | | 0.04 | | 0.05 | | 0.012 | |
| AVE d0 | 6.1 | | 6.1 | | 5.3 | | 4.9 | | 104.2 | |
| AVE d0-d28 | 2.3 | | 3.0 | | 2.2 | | 2.0 | | 37.5 | |

Using a paired TTEST, you first find the differences, then use these values to obtain AVE and StDev values; thus the AVE and TTEST values above are ok, but use the STDEV values below 36% 36%

| | TENDER POINT VALUES Cervical | | | | Lateral epicondyle | | | Occiput | | | USING THE SUMMATION of all TP: i.e. SUM of all 18 tp per subj: | | |
|---|---|---|---|---|---|---|---|---|---|---|---|---|---|
| | d0 | d28 | diff | | d0 | d28 | diff | d0 | d28 | diff | d0 | d28 | diff |
| % change | | 1R | | | | 5R | | | 10L | | | | |
| | | | | | | | | | | | 0 | 4 | −4 |
| | 0 | 0 | 0 | | 0 | 0 | 0 | 0 | 0 | 0 | 104 | 64 | 40 |
| | 6 | 5 | 1 | | 4 | 0 | 4 | 6 | 5 | 1 | 126 | 24 | 102 |
| | 8 | 5 | 3 | | 0 | 0 | 0 | 8 | 0 | 8 | 110 | 41 | 69 |
| | 7 | 1 | 6 | | 6 | 4 | 2 | 7 | 4 | 3 | 88 | 90 | −2 |
| | 8 | 5 | 3 | | 0 | 4 | −4 | 9 | 4 | 5 | 123 | 98 | 25 |
| | 8 | 7 | 1 | | 8 | 3 | 5 | 8 | 5 | 3 | 144 | 58 | 86 |
| | 8 | 2 | 6 | | 8 | 3 | 5 | 8 | 4 | 4 | 180 | 80 | 100 |
| | 10 | 3 | 7 | | 10 | 3 | 7 | 10 | 3 | 7 | 58.5 | 38 | 20.5 |
| | 4 | 2 | 2 | primary endpt as sum | 0 | 0 | 0 | 0 | 2 | −2 | 78 | 113 | −35 |
| | 4 | 9 | −5 | | 3 | 9 | −6 | 4 | 3 | 1 | 144 | 120 | 24 |
| | 8 | 6 | 2 | | 8 | 6 | 2 | 8 | 6 | 2 | 4 Nov. 2003 | 95 | 70 | 25 |
| | 6 | 5 | 1 | | 5 | 5 | 0 | 7 | 6 | 1 | AVE (ave diff) | | 37.5 |
| AVERAGE | | | 2.3 | the greater the diff the better | | | 1.3 | | | 2.8 | STDEV (of diff) | | 43.4 |
| STDEV | | | 3.2 | the lower the spread the better | | | 3.8 | | | 2.9 | SEM (of diff) | | 12.5 |
| SEM | | | 0.9 | | | | 1.1 | | | 0.8 | TTEST | 2 tailed | 0.012 |
| change of d0 minus d28 | | | | | | | | | | | | 1 tailed | 0.006 |
| therapy should lower the number | | | | | | | | | | | ave diff/18= | | 2.086 |
| i.e. lower the pain sensation | | | | | | | | | | | TTEST | array1 sum of TPs d1 | |
| n | | | 12 | | | | 12 | | | 12 | array2 sum of TPs d28 | | |
| | SFBC: | | | | | | | | | | 2 = 2 tailed | | |
| | | | | | | | | | | | 1 = paired | | |

| | 3R. Second rib PT | 3R. Second rib d28 | 4L. Second rib PT | 4L. Second rib d28 | 11R. Trapezius PT | 11R. Trapezius d28 | 12L. Trapezius PT | 12L. Trapezius d28 |
|---|---|---|---|---|---|---|---|---|
| AVE | 4.14 | 4.65 | 3.64 | 4.45 | 4.45 | 5.74 | 4.27 | 5.36 |
| STD EV | 1.07 | 1.66 | 1.05 | 1.63 | 1.33 | 2.27 | 1.51 | 2.43 |
| SEM | 0.31 | 0.48 | 0.30 | 0.47 | 0.38 | 0.65 | 0.43 | 0.70 |

TP dolorimetry readings for graphing
PT = pretreatment

| Pat ID # | Group | interview dates d0 | d28 | Skin d0 | Skin d28 | Neck d0 | Neck d28 | Lungs d0 | Lungs d28 | Cardiovascular CV d0 | d28 |
|---|---|---|---|---|---|---|---|---|---|---|---|
| 001 | 1 | Nov. 7, 2001 | Dec. 5, 2001 | check | mild pruritus resolved | | | | clear | no m | |
| 002 | 2 | Feb. 7, 2002 | Mar. 9, 2002 | photosenssitive rash; ox- lupers HCQ -> "stomach intol; nl x back skin rash | | | | | | tachycardia | |
| 005 | 1 | Nov. 9, 2001 | Dec. 7, 2001 | R knee scar | | no LN | some L side neck pain | clear | | no m | |
| 006 | 3 | Mar. 23, 2002 | Apr. 20, 2002 | clear | | | | clear | | | |
| 007 | 1 | Nov. 9, 2001 | Dec. 5, 2001 | no lesions through scar over nose | rash on day 1 of gel; did not occur-was on r forearm | no LN | | clear | | no m | |
| 009 | 1 | Nov. 5, 2001 | Dec. 3, 2001 | check | | no LN, +incr thyroid | | clear | | grade 2/6 SEM in A (anterior) & P (posterior) area, nl pulses palps on occasion; heart m | |
| 010 | 2 | Feb. 6, 2002 | Mar. 9, 2002 | scabies in fall | | | | | | | |

-continued

| Pat ID # | Group | interview dates d0 | d28 | Skin d0 | Skin d28 | Neck d0 | Neck d28 | Lungs d0 | Lungs d28 | Cardiovascular CV d0 | d28 |
|---|---|---|---|---|---|---|---|---|---|---|---|
| 011 | 2 | Feb. 5, 2002 | Mar. 12, 2002 | | | | | | clear | GR 2/6 syst. M at LLS B; no exertional C.P., + m | |
| 012 | 2 | Feb. 5, 2002 | Mar. 12, 2002 | | | | | | nl | nl heart, c.p. assoc. w/chest wall | |
| 016 | 3 | Mar. 23, 2002 | Apr. 20, 2002 | clear | | | | | clear | Gr1/6 non rad murmur | |
| 017 | 3 | Mar. 23, 2002 | Apr. 20, 2002 | no acne | | | | | clear | | |
| 018 | 3 | Mar. 28, 2002 | Apr. 20, 2002 | clear | | | | | nl | nl murmur | |

INTERVIEW DATES FOR ALL SUBJECTS Nov. 5, 2001- Apr. 29, 2002
(see tab 2a "PatientQ & stats")

| | Abdominal d0 | d28 | Edema d0 | d28 | Head Eyes Ears Nose Throat HEENT d0 | d28 | Thyroid d0 | d28 |
|---|---|---|---|---|---|---|---|---|
| 001 | no incr L/S, no masses | | | | no mucosal abnl, no conjunctival/ scleral injection | | no incr thyroid | |
| 002 | IBS | | | | | | hypothyroidism, takes premarin | |
| 005 | no incr liver or RUQ, tenderness, chole. Scar | | | | | | nl | |
| 006 | nl liver span (8 cm) | | tr. Edema | | | | hypothyroidism | |
| 007 | no incr liver | | | | | | nl | |
| 009 | no incr L/S | | neg | | | | | |
| 010 | IBS | | | | eyes feel unforcused even w/ glasses | | neg thyroid disease | |
| 011 | tender abd w/o organomeg | | | | | | no incr thyroid | |
| 012 | nl | | | | | | no incr thyroid | |
| 016 | liver nl | | Ext-no edema | | | | | |
| 017 | | | | | | | hypothyroid | throid adjustment occured at same time. No change in symptoms |
| 018 | chole, cholecystechtomy RUQ, rt upper quadrant L/S? | | | | | | nl, normal | |

| | neuro d0 | neuro d28 | Joints d0 | Joints d28 | Other d0 | Other d28 |
|---|---|---|---|---|---|---|
| 001 | | 2 H.A. since on Testosterone-bad; not like this since menopause | sl boggy knees, nl hips | no major change in c/o | | constipation resloved |
| 002 | daily H.A. | | FMS - 1993 (ortho) | | | 002, early menopause, TAH/BSO at age 30 |
| 005 | DTRs nl | | | decr pain, incr energy | looks well | incr breast size, wgt gain5-6 lbs |
| 006 | h/o H.A. but now more sinus/ allergy related | | some joint pain esp fingers responsive to NSAID | | pos synuritis scattered MCP's, PIP's & L Knee eff. | no symptomatic change |
| 007 | DTRs nl | incr freq of H.A. and usually doesn't have, esp. over thanksgiving holiday more achey, esp. am. No change in fatigue. | | | plump, moves w/ease, neg SLR | possible allergy to latex |
| 009 | decr DTR R ankle c/w L, muscle | R leg pain; now on vicodin (new) | nl | FMS | no signif PMH x for 4 breast lumps, pos | |

-continued

| | neuro d0 | neuro d28 | Joints d0 | Joints d28 | Other d0 | Other d28 |
|---|---|---|---|---|---|---|
| | loss R lat prox calf assoc w/leg pain & weakness | | | | ecchymosis over L knee 2o fall | |
| 010 | pos h/o H.A.; R supraorbital sharp transient pain | | FMS dx by Pat Ford Approx 2 years ago | | surgeries: L knee arthroscopic surg.; TAH/BSO. Allergies: dust/tree pollen/venom desensitiztion; asthma (mild) | |
| 011 | | | 0 ankle DTRs, others 2+ sym | | absent R fingers 4 & 5; tender mcp - +/− STS on L 1 + STS on R; fatigue, widespread ms pain - legs hurt the most | 011, early menopause, alcohol abuse, long surgical hx, did surprisingly well, did not find TAH/BSO in electronic chart; OV- noted elsewhere |
| 012 | some H.A. | | | | Surgeries: GB 1991; TAH June 1992 0 BSO, has ovaries; nl vibratory sense, 3+ DTRs | |
| 016 | | | | | prior study patient; pos bi-polar illness on Effexor | |
| 017 | | | | | pos ms pain all over; fatiuge, IBS, pos rosacea | |
| 018 | pos H.A. | | | | excellent health; pos FMS & c/o hand pain | tender points seemed exquisitely painful (point 1, 2, 3, 4, 9, 10, 11, 12, 13, 14), but pt rated them 4 of 10 |

DTR, deep tender reflexes
c/w = compared with

PMH, past medical history
x(with line over it), except SLR?

Free T WNL Results

| Subject No. | Day | Cmax | Tmax | Cmin | Tmin | AUC0-24 | Cave | | | |
|---|---|---|---|---|---|---|---|---|---|---|
| 1 | 1 | 3.32 | 24.5 | 1.35 | 0 | 54.4 | 2.27 | 1 | 009 | |
| 1 | 28 | 4.10 | 24.1 | 1.27 | 6.1 | 68.0 | 2.83 | 2 | 005 | |
| 2 | 1 | 1.46 | 24.8 | 0.344 | 8.3 | 19.9 | 0.83 | 3 | 007 | |
| 2 | 28 | 5.19 | 10.2 | 1.98 | 12.2 | 72.6 | 3.02 | 4 | 001 | |
| 3 | 1 | 3.13 | 4.3 | 1.08 | 8.3 | 43.2 | 1.80 | 6 | 002 | |
| 3 | 28 | 4.21 | 1.6 | 1.10 | 11.5 | 42.7 | 1.78 | 7 | 010 | FT outlyer |
| 4 | 1 | 1.74 | 4.3 | 0.262 | 0 | 24.3 | 1.01 | 8 | 011 | |
| 4 | 28 | 4.64 | 2.2 | 1.75 | 0 | 51.4 | 2.14 | 9 | 012 | |
| 6 | 1 | 0.949 | 6.5 | 0.261 | 3.4 | 13.7 | 0.569 | 10 | 017 | |
| 6 | 28 | 4.75 | 8.1 | 2.27 | 1.2 | 90.1 | 3.75 | 11 | 006 | |
| 7 | 1 | 6.86 | 1.9 | 3.40 | 4.0 | 126.7 | 5.28 | 12 | 016 | FT outlyer |
| 7 | 28 | 7.49 | 12.0 | 3.77 | 10.0 | 157.7 | 6.57 | 13 | 018 | |
| 8 | 1 | 1.40 | 2.1 | 0.175 | 0 | 14.2 | 0.592 | | | |
| 8 | 28 | 2.32 | 12.3 | 0.775 | 24.3 | 32.3 | 1.35 | | | |
| 9 | 1 | 2.05 | 6.3 | 0.720 | 1.3 | 39.2 | 1.63 | | | |
| 9 | 28 | 3.05 | 0 | 1.15 | 3.3 | 50.0 | 2.08 | | | |
| 10 | 1 | 2.32 | 3 | 0.473 | 1.0 | 23.6 | 0.982 | | | |
| 10 | 28 | 1.81 | 10.3 | 0.714 | 4.3 | 27.9 | 1.16 | | | |
| 11 | 1 | 6.86 | 24.2 | 0.091 | 0 | 64.1 | 2.67 | | | |
| 11 | 28 | 5.58 | 23.9 | 0.830 | 3.2 | 51.6 | 2.15 | | | |
| 12 | 1 | 10.9 | 23.4 | 5.99 | 2.7 | 178.1 | 7.42 | | | |
| 12 | 28 | 9.63 | 23.9 | 4.73 | 11.8 | 166.8 | 6.95 | | | |
| 13 | 1 | 3.21 | 24.5 | 0.648 | 1.2 | 53.7 | 2.24 | | | |
| 13 | 28 | 3.49 | 0 | 1.04 | 3.8 | 52.2 | 2.18 | | | |

Free T WNL Results All Subjects, Day 1

| Subject No. | Subject | Day | Cmax | Tmax | Cmin | Tmin | AUC0-24 | Cave |
|---|---|---|---|---|---|---|---|---|
| 1 | | 1 | 3.32 | 24.5 | 1.35 | 0 | 54.4 | 2.27 |
| 2 | | 1 | 1.46 | 24.8 | 0.344 | 8.3 | 19.9 | 0.83 |
| 3 | | 1 | 3.13 | 4.3 | 1.08 | 8.3 | 43.2 | 1.80 |

| Free T WNL Results All Subjects, Day 1 | | | | | | (from Cmin page) | |
|---|---|---|---|---|---|---|---|
| Subject No. | Subject | Day | Cmax | Tmax | Cmin | Tmin | AUC0-24 | Cave |
| 4 | | 1 | 1.74 | 4.3 | 0.262 | 0 | 24.3 | 1.01 |
| 6 | | 1 | 0.949 | 6.5 | 0.261 | 3.4 | 13.7 | 0.569 |
| 7 | | 1 | 6.86 | 1.9 | 3.40 | 4.0 | 126.7 | 5.28 |
| 8 | | 1 | 1.40 | 2.1 | 0.175 | 0 | 14.2 | 0.592 |
| 9 | | 1 | 2.05 | 6.3 | 0.720 | 1.3 | 39.2 | 1.63 |
| 10 | | 1 | 2.32 | 3 | 0.473 | 1.0 | 23.6 | 0.982 |
| 11 | | 1 | 6.86 | 24.2 | 0.091 | 0 | 64.1 | 2.67 |
| 12 | | 1 | 10.9 | 23.4 | 5.99 | 2.7 | 178.1 | 7.42 |
| 13 | | 1 | 3.21 | 24.5 | 0.648 | 1.2 | 53.7 | 2.24 |
| | Mean | | 3.68 | | 1.23 | | 54.6 | 2.27 |
| | SD | | 2.99 | | 1.75 | | 49.8 | 2.08 |
| | Median | | 2.72 | 6.38 | 0.561 | 1.21 | 41.2 | 1.72 |
| | Min | | 0.949 | 1.92 | 0.0910 | 0 | 13.7 | 0.569 |
| | Max | | 10.9 | 24.8 | 5.99 | 8.28 | 178 | 7.42 |
| | Geomean | | 2.84 | | 0.606 | | 39.8 | 1.66 |
| | CI diff | +/− | 1.69 | | 0.989 | | 28.2 | 1.17 |
| | CI lower | | 1.99 | | 0.244 | | 26.4 | 1.10 |
| | CI upper | | 5.37 | | 2.22 | | 82.8 | 3.45 |

| Free T WNL Results Without Subjects 7 and 12, Day 1 | | | | | (from Cmin page) | | | | TOTAL T from Cmin tab: | | RATIO | |
|---|---|---|---|---|---|---|---|---|---|---|---|---|
| | | | | | | | | | Day 1 | Day 28 | Day 28/1 | Day 28/1 |
| Subject No. | Day | Cmax | Tmax | Cmin | Tmin | AUC0-24 | Cave | Subject No. | TT Cmin | TT Cmin | Cmin TT | Cmin TT |
| 1 | 1 | 3.32 | 24.5 | 1.35 | 0 | 54.4 | 2.27 | 1 | 0.25 | 0.48 | 1.92 | 0.23 |
| 2 | 1 | 1.46 | 24.8 | 0.344 | 8.3 | 19.9 | 0.83 | 2 | 0.37 | 1.47 | 3.97 | 1.10 |
| 3 | 1 | 3.13 | 4.3 | 1.08 | 8.3 | 43.2 | 1.80 | 3 | 0.13 | 0.61 | 4.69 | 0.48 |
| 4 | 1 | 1.74 | 4.3 | 0.262 | 0 | 24.3 | 1.01 | 4 | 0.09 | 0.77 | 8.56 | 0.68 |
| 6 | 1 | 0.949 | 6.5 | 0.261 | 3.4 | 13.7 | 0.569 | 6 | 0.11 | 1.67 | 15.18 | 1.56 |
| | | | | | | | | 7 | 0.25 | 0.85 | 3.40 | 0.60 |
| 8 | 1 | 1.40 | 2.1 | 0.175 | 0 | 14.2 | 0.592 | 8 | 0 | 0.68 | nc | 0.68 |
| 9 | 1 | 2.05 | 6.3 | 0.720 | 1.3 | 39.2 | 1.63 | 9 | 0.22 | 0.6 | 2.73 | 0.38 |
| 10 | 1 | 2.32 | 3 | 0.473 | 1.0 | 23.6 | 0.982 | 10 | 0.21 | 0.37 | 1.76 | 0.16 |
| 11 | 1 | 6.86 | 24.2 | 0.091 | 0 | 64.1 | 2.67 | 11 | 0.02 | 0.21 | 10.50 | 0.19 |
| | | | | | | | | 12 | 0.19 | 0.32 | 1.68 | 0.13 |
| 13 | 1 | 3.21 | 24.5 | 0.648 | 1.2 | 53.7 | 2.24 | 13 | 0.17 | 0.55 | 3.24 | 0.38 |
| Mean | | 2.64 | | 0.541 | | 35.0 | 1.46 | | | | | |
| SD | | 1.70 | | 0.412 | | 18.3 | 0.762 | | | | | |
| Median | | 2.19 | 6.38 | 0.409 | 1.09 | 31.8 | 1.32 | | | | | |
| Min | | 0.949 | 2.08 | 0.0910 | 0 | 13.7 | 0.569 | | | | | |
| Max | | 6.86 | 24.8 | 1.35 | 8.28 | 64.1 | 2.67 | | | | | |
| Geomean | | 2.27 | | 0.406 | | 30.5 | 1.27 | | | | | |
| CI diff +/− | | 1.05 | | 0.255 | | 11.3 | 0.473 | | | | | |
| CI lower | | 1.59 | | 0.285 | | 23.7 | 0.987 | | | | | |
| CI upper | | 3.69 | | 0.796 | | 46.4 | 1.93 | | | | | |

| Free T WNL Results: All Subjects, Day 28 | | | | | | | | Day 28/Day 1 Ratios | | | | Day 28-Day 1 Differential | | | |
|---|---|---|---|---|---|---|---|---|---|---|---|---|---|---|---|
| Subject No. | Day | Cmax | Tmax | Cmin | Tmin | AUC0-24 | Cave | Cmax | Cmin | AUC0-24 | Cave | Cmax | Cmin | AUC0-24 | Cave |
| 1 | 28 | 4.10 | 24.1 | 1.27 | 6.1 | 68.0 | 2.83 | 1.24 | 0.94 | 1.25 | 1.25 | 0.78 | −0.08 | 13.62 | 0.57 |
| 2 | 28 | 5.19 | 10.2 | 1.98 | 12.2 | 72.6 | 3.02 | 3.56 | 5.76 | 3.64 | 3.64 | 3.73 | 1.64 | 52.65 | 2.19 |
| 3 | 28 | 4.21 | 1.6 | 1.10 | 11.5 | 42.7 | 1.78 | 1.35 | 1.01 | 0.99 | 0.99 | 1.08 | 0.02 | −0.41 | −0.02 |
| 4 | 28 | 4.64 | 2.2 | 1.75 | 0 | 51.4 | 2.14 | 2.67 | 6.69 | 2.11 | 2.11 | 2.91 | 1.49 | 27.01 | 1.13 |
| 6 | 28 | 4.75 | 8.1 | 2.27 | 1.2 | 90.1 | 3.75 | 5.01 | 8.71 | 6.60 | 6.60 | 3.80 | 2.01 | 76.42 | 3.18 |

| Free T WNL Results: All Subjects, Day 28 | | | | | | | | Day 28/Day 1 Ratios | | | | Day 28-Day 1 Differential | | | |
|---|---|---|---|---|---|---|---|---|---|---|---|---|---|---|---|
| Subject No. | Day | Cmax | Tmax | Cmin | Tmin | AUC0-24 | Cave | Cmax | Cmin | AUC0-24 | Cave | Cmax | Cmin | AUC0-24 | Cave |
| 7 | 28 | 7.49 | 12.0 | 3.77 | 10.0 | 157.7 | 6.57 | 1.09 | 1.11 | 1.25 | 1.25 | 0.63 | 0.37 | 31.05 | 1.29 |
| 8 | 28 | 2.32 | 12.3 | 0.775 | 24.3 | 32.3 | 1.35 | 1.66 | 4.43 | 2.27 | 2.27 | 0.92 | 0.60 | 18.11 | 0.75 |
| 9 | 28 | 3.05 | 0 | 1.15 | 3.3 | 50.0 | 2.08 | 1.49 | 1.60 | 1.28 | 1.28 | 1.00 | 0.43 | 10.80 | 0.45 |
| 10 | 28 | 1.81 | 10.3 | 0.714 | 4.3 | 27.9 | 1.16 | 0.78 | 1.51 | 1.19 | 1.19 | −0.51 | 0.24 | 4.37 | 0.18 |
| 11 | 28 | 5.58 | 23.9 | 0.830 | 3.2 | 51.6 | 2.15 | 0.81 | 9.12 | 0.81 | 0.81 | −1.28 | 0.74 | −12.47 | −0.52 |
| 12 | 28 | 9.63 | 23.9 | 4.73 | 11.8 | 166.8 | 6.95 | 0.89 | 0.79 | 0.94 | 0.94 | −1.24 | −1.26 | −11.31 | −0.47 |
| 13 | 28 | 3.49 | 0 | 1.04 | 3.8 | 52.2 | 2.18 | 1.09 | 1.61 | 0.97 | 0.97 | 0.28 | 0.40 | −1.41 | −0.06 |
| Mean | | 4.69 | | 1.78 | | 72.0 | 3.00 | 1.80 | 3.61 | 1.94 | 1.94 | 1.01 | 0.550 | 17.4 | 0.724 |
| SD | | 2.17 | | 1.27 | | 45.5 | 1.90 | 1.30 | 3.19 | 1.67 | 1.67 | 1.71 | 0.871 | 26.3 | 1.10 |
| Median | | 4.43 | 10.2 | 1.21 | 5.21 | 51.9 | 2.16 | 1.29 | 1.60 | 1.25 | 1.25 | 0.852 | 0.413 | 12.2 | 0.509 |
| Min | | 1.81 | 0 | 0.7140 | 0 | 27.9 | 1.16 | 0.78 | 0.79 | 0.81 | 0.81 | −1.28 | −1.26 | −12.5 | −0.519 |
| Max | | 9.63 | 24.1 | 4.73 | 24.3 | 167 | 6.95 | 5.01 | 9.12 | 6.60 | 6.60 | 3.80 | 2.01 | 76.4 | 3.18 |
| Geomean | | 4.26 | | 1.48 | | 61.8 | 2.58 | 1.50 | 2.44 | 1.55 | 1.55 | | | | |
| CI diff | +/− | 1.23 | | 0.717 | | 25.7 | 1.07 | 0.74 | 1.80 | 0.95 | 0.95 | 0.968 | 0.493 | 14.9 | 0.620 |
| CI lower | | 3.46 | | 1.07 | | 46.2 | 1.93 | 1.07 | 1.80 | 0.99 | 0.99 | 0.040 | 0.057 | 2.48 | 0.103 |
| CI upper | | 5.92 | | 2.50 | | 97.7 | 4.07 | 2.54 | 5.41 | 2.89 | 2.89 | 1.98 | 1.04 | 32.3 | 1.34 |

| Free T WNL Results FREE TESTOSTERONE- Without Subjects 7 and 12, Day 28 | | | | | | | | FREE TESTOSTERONE Day 28/Day 1 Ratio | | | |
|---|---|---|---|---|---|---|---|---|---|---|---|
| Subject No. | Day | Cmax | Tmax | Cmin | Tmin | AUC0-24 | Cave | Cmax | Cmin | AUC0-24 | Cave |
| 1 | 28 | 4.10 | 24.1 | 1.27 | 6.1 | 68.0 | 2.83 | 1.24 | 0.94 | 1.25 | 1.25 |
| 2 | 28 | 5.19 | 10.2 | 1.98 | 12.2 | 72.6 | 3.02 | 3.56 | 5.76 | 3.64 | 3.64 |
| 3 | 28 | 4.21 | 1.6 | 1.10 | 11.5 | 42.7 | 1.78 | 1.35 | 1.01 | 0.99 | 0.99 |
| 4 | 28 | 4.64 | 2.2 | 1.75 | 0 | 51.4 | 2.14 | 2.67 | 6.69 | 2.11 | 2.11 |
| 6 | 28 | 4.75 | 8.1 | 2.27 | 1.2 | 90.1 | 3.75 | 5.01 | 8.71 | 6.60 | 6.60 |
| 8 | 28 | 2.32 | 12.3 | 0.775 | 24.3 | 32.3 | 1.35 | 1.66 | 4.43 | 2.27 | 2.27 |
| 9 | 28 | 3.05 | 0 | 1.15 | 3.3 | 50.0 | 2.08 | 1.49 | 1.60 | 1.28 | 1.28 |
| 10 | 28 | 1.81 | 10.3 | 0.714 | 4.3 | 27.9 | 1.16 | 0.78 | 1.51 | 1.19 | 1.19 |
| 11 | 28 | 5.58 | 23.9 | 0.830 | 3.2 | 51.6 | 2.15 | 0.81 | 9.12 | 0.81 | 0.81 |
| 13 | 28 | 3.49 | 0 | 1.04 | 3.8 | 52.2 | 2.18 | 1.09 | 1.61 | 0.97 | 0.97 |
| Mean | | 3.91 | | 1.29 | | 53.9 | 2.25 | 1.96 | 4.14 | 2.11 | 2.11 |
| SD | | 1.23 | | 0.54 | | 18.7 | 0.78 | 1.38 | 3.24 | 1.80 | 1.80 |
| Median | | 4.16 | 9.1 | 1.12 | 4.1 | 51.5 | 2.15 | 1.42 | 3.02 | 1.26 | 1.26 |
| Min | | 1.81 | 0 | 0.714 | 0 | 27.9 | 1.16 | 0.780 | 0.941 | 0.805 | 0.805 |
| Max | | 5.58 | 24.1 | 2.27 | 24.3 | 90.1 | 3.75 | 5.01 | 9.12 | 6.60 | 6.60 |
| Geomean | | 3.71 | | 1.20 | | 51.0 | 2.12 | 1.63 | 2.95 | 1.67 | 1.67 |
| CI diff | +/− | 0.763 | | 0.332 | | 11.6 | 0.483 | 0.853 | 2.01 | 1.11 | 1.11 |
| CI lower | | 3.15 | | 0.956 | | 42.3 | 1.76 | 1.11 | 2.13 | 1.00 | 1.00 |
| CI upper | | 4.68 | | 1.62 | | 65.5 | 2.73 | 2.82 | 6.15 | 3.22 | 3.22 |

| Free T WNL Results FREE TESTOSTERONE- Without Subjects 7 and 12, Day 28 | | FREE TESTOSTERONE Day 28-Day 1 Differential | | | | TOTAL TESTOSTERONE (ng/mL)RATIO | | | |
|---|---|---|---|---|---|---|---|---|---|
| | | | | | | Day 1 | Day 28 | Day 28/1 | Day 28/1 |
| Subject No. | Day | Cmax | Cmin | AUC0-24 | Cave | TT Cmin | TT Cmin | Cmin TT | Cmin TT |
| 1 | 28 | 0.78 | −0.08 | 13.62 | 0.57 | 0.25 | 0.48 | 1.92 | 0.23 |
| 2 | 28 | 3.73 | 1.64 | 52.65 | 2.19 | 0.37 | 1.47 | 3.97 | 1.10 |
| 3 | 28 | 1.08 | 0.02 | −0.41 | −0.02 | 0.13 | 0.61 | 4.69 | 0.48 |
| 4 | 28 | 2.91 | 1.49 | 27.01 | 1.13 | 0.09 | 0.77 | 8.56 | 0.68 |
| 6 | 28 | 3.80 | 2.01 | 76.42 | 3.18 | 0.11 | 1.67 | 15.18 | 1.56 |
| | | | | | | 0.25 | 0.85 | 3.40 | 0.60 |
| 8 | 28 | 0.92 | 0.60 | 18.11 | 0.75 | 0 | 0.68 | nc | 0.68 |
| 9 | 28 | 1.00 | 0.43 | 10.80 | 0.45 | 0.22 | 0.6 | 2.73 | 0.38 |
| 10 | 28 | −0.51 | 0.24 | 4.37 | 0.18 | 0.21 | 0.37 | 1.76 | 0.16 |
| 11 | 28 | −1.28 | 0.74 | −12.47 | −0.52 | 0.02 | 0.21 | 10.50 | 0.19 |
| | | | | | | 0.19 | 0.32 | 1.68 | 0.13 |
| 13 | 28 | 0.28 | 0.40 | −1.41 | −0.06 | 0.17 | 0.55 | 3.24 | 0.38 |

|  |  |  |  |  |  |  |  |  |
|---|---|---|---|---|---|---|---|---|
| Mean | | 1.27 | 0.748 | 18.9 | 0.786 | 0.17 | 0.72 | 5.24 | 0.55 |
| SD | | 1.71 | 0.720 | 27.1 | 1.13 | 0.10 | 0.44 | 4.35 | 0.42 |
| Median | | 0.959 | 0.516 | 12.2 | 0.509 | 0.18 | 0.61 | 3.40 | 0.43 |
| Min | | −1.28 | −0.079 | −12.5 | −0.519 | 0.00 | 0.21 | 1.68 | 0.13 |
| Max | | 3.80 | 2.01 | 76.4 | 3.18 | 0.37 | 1.67 | 15.18 | 1.56 |
| Geomean | | | | | | | | | |
| CI diff | +/− | 1.059 | 0.446 | 16.8 | 0.699 | 0.06 | 0.25 | 2.57 | 0.24 |
| CI lower | | 0.211 | 0.302 | 2.10 | 0.088 | 0.11 | 0.47 | 2.67 | 0.31 |
| CI upper | | 2.33 | 1.19 | 35.6 | 1.48 | 0.23 | 0.96 | 7.81 | 0.79 |

| Free T WNL Results | | | Concentration |
|---|---|---|---|
| Subject No. | Day | Time (hr) | (pg/mL) |
| 1 | 1 | 0.00 | 1.348 |
| 1 | 1 | 1.50 | 1.457 |
| 1 | 1 | 2.33 | 1.887 |
| 1 | 1 | 3.08 | 1.554 |
| 1 | 1 | 3.83 | 1.606 |
| 1 | 1 | 5.97 | 1.524 |
| 1 | 1 | 8.08 | 1.643 |
| 1 | 1 | 9.87 | 1.905 |
| 1 | 1 | 12.00 | 2.158 |
| 1 | 1 | 24.50 | 3.321 |
| 2 | 1 | 0.00 | 1.165 |
| 2 | 1 | 1.67 | 0.908 |
| 2 | 1 | 2.47 | 0.830 |
| 2 | 1 | 3.43 | 0.872 |
| 2 | 1 | 4.50 | 0.897 |
| 2 | 1 | 6.37 | 0.636 |
| 2 | 1 | 8.25 | 0.344 |
| 2 | 1 | 10.33 | 0.517 |
| 2 | 1 | 12.17 | 0.392 |
| 2 | 1 | 24.75 | 1.458 |
| 3 | 1 | 0.00 | 1.182 |
| 3 | 1 | 2.08 | 1.804 |
| 3 | 1 | 3.25 | 2.075 |
| 3 | 1 | 4.30 | 3.125 |
| 3- | 1 | 6.25 | 1.964 |
| 3 | 1 | 8.28 | 1.083 |
| 3 | 1 | 10.22 | 1.529 |
| 3 | 1 | 12.20 | 1.546 |
| 3 | 1 | 24.42 | 1.959 |
| 4 | 1 | 0.00 | 0.262 |
| 4 | 1 | 1.75 | 0.564 |
| 4 | 1 | 2.50 | 0.899 |
| 4 | 1 | 3.38 | 1.127 |
| 4 | 1 | 4.33 | 1.736 |
| 4 | 1 | 6.33 | 0.584 |
| 4 | 1 | 8.30 | 0.814 |
| 4 | 1 | 10.17 | 0.630 |
| 4 | 1 | 12.15 | 1.013 |
| 4 | 1 | 24.50 | 1.279 |
| 6 | 1 | 0.00 | 0.394 |
| 6 | 1 | 1.33 | 0.383 |
| 6 | 1 | 2.40 | 0.484 |
| 6 | 1 | 3.42 | 0.261 |
| 6 | 1 | 4.52 | 0.543 |
| 6 | 1 | 6.50 | 0.949 |
| 6 | 1 | 8.83 | 0.678 |
| 6 | 1 | 10.33 | 0.358 |
| 6 | 1 | 12.25 | 0.311 |
| 6 | 1 | 24.58 | 0.834 |
| 7 | 1 | 0.00 | 5.253 |
| 7 | 1 | 1.25 | 4.482 |
| 7 | 1 | 1.92 | 6.859 |
| 7 | 1 | 2.97 | 5.518 |
| 7 | 1 | 3.95 | 3.397 |
| 7 | 1 | 5.95 | 3.846 |
| 7 | 1 | 8.00 | 4.190 |
| 7 | 1 | 10.08 | 3.748 |
| 7 | 1 | 12.00 | 4.929 |
| 7 | 1 | 24.75 | 6.654 |
| 8 | 1 | 0.00 | 0.175 |
| 8 | 1 | 1.08 | 0.713 |
| 8 | 1 | 2.08 | 1.395 |
| 8 | 1 | 3.00 | 0.666 |
| 8 | 1 | 4.08 | 0.840 |
| 8 | 1 | 6.08 | 0.377 |
| 8 | 1 | 8.00 | 0.439 |
| 8 | 1 | 10.00 | 0.451 |
| 8 | 1 | 11.92 | 0.438 |
| 8 | 1 | 24.00 | 0.750 |
| 9 | 1 | 0.00 | 0.880 |
| 9 | 1 | 1.25 | 0.720 |
| 9 | 1 | 2.25 | 1.044 |
| 9 | 1 | 3.25 | 1.338 |
| 9 | 1 | 4.20 | 1.405 |
| 9 | 1 | 6.25 | 2.052 |
| 9 | 1 | 8.25 | 1.736 |
| 9 | 1 | 10.25 | 1.301 |
| 9 | 1 | 12.22 | 1.973 |
| 9 | 1 | 24.25 | 1.555 |
| 10 | 1 | 0.00 | 0.617 |
| 10 | 1 | 1.00 | 0.473 |
| 10 | 1 | 1.93 | 1.781 |
| 10 | 1 | 3.00 | 2.324 |
| 10 | 1 | 4.08 | 1.219 |
| 10 | 1 | 6.00 | 0.981 |
| 10 | 1 | 7.93 | 1.716 |
| 10 | 1 | 10.00 | 0.612 |
| 10 | 1 | 11.88 | 0.670 |
| 10 | 1 | 24.00 | 0.905 |
| 11 | 1 | 0.00 | 0.091 |
| 11 | 1 | 1.25 | 0.835 |
| 11 | 1 | 2.17 | 0.795 |
| 11 | 1 | 3.42 | 3.350 |
| 11 | 1 | 4.33 | 1.503 |
| 11 | 1 | 6.50 | 1.716 |
| 11 | 1 | 8.17 | 1.531 |
| 11 | 1 | 10.50 | 1.355 |
| 11 | 1 | 12.33 | 0.939 |
| 11 | 1 | 24.20 | 6.861 |
| 12 | 1 | 0.00 | 7.753 |
| 12 | 1 | 0.92 | 6.322 |
| 12 | 1 | 1.75 | 6.469 |
| 12 | 1 | 2.67 | 5.987 |
| 12 | 1 | 3.67 | 6.603 |
| 12 | 1 | 5.67 | 7.137 |
| 12 | 1 | 7.82 | 6.456 |
| 12 | 1 | 9.58 | 5.998 |
| 12 | 1 | 11.53 | 6.478 |
| 12 | 1 | 23.38 | 10.876 |
| 13 | 1 | 0.00 | 0.654 |
| 13 | 1 | 1.17 | 0.648 |
| 13 | 1 | 2.17 | 1.286 |
| 13 | 1 | 3.25 | 1.314 |
| 13 | 1 | 4.25 | 2.089 |
| 13 | 1 | 6.17 | 2.275 |
| 13 | 1 | 8.17 | 1.992 |
| 13 | 1 | 10.17 | 1.766 |

| Free T WNL Results | | | Concentration |
|---|---|---|---|
| Subject No. | Day | Time (hr) | (pg/mL) |
| 13 | 1 | 12.17 | 2.120 |
| 7 | 1 | 24.45 | 3.209 |
| 1 | 28 | 0.00 | 2.116 |
| 1 | 28 | 1.25 | 2.643 |
| 1 | 28 | 2.00 | 2.007 |
| 1 | 28 | 2.92 | 1.354 |
| 1 | 28 | 4.08 | 1.409 |
| 1 | 28 | 6.08 | 1.269 |
| 1 | 28 | 8.00 | 2.161 |
| 1 | 28 | 10.08 | 3.252 |
| 1 | 28 | 11.83 | 2.954 |
| 1 | 28 | 24.05 | 4.104 |
| 2 | 28 | 0.00 | 2.503 |
| 2 | 28 | 1.17 | 2.373 |
| 2 | 28 | 2.08 | 2.629 |
| 2 | 28 | 3.00 | 2.298 |
| 2 | 28 | 4.25 | 2.818 |
| 2 | 28 | 6.25 | 3.151 |
| 2 | 28 | 7.83 | 2.473 |
| 2 | 28 | 10.17 | 5.187 |
| 2 | 28 | 12.17 | 1.980 |
| 2 | 28 | 24.42 | 3.805 |
| 3 | 28 | 0.00 | 3.802 |
| 3 | 28 | 0.90 | 2.984 |
| 3 | 28 | 1.62 | 4.209 |
| 3 | 28 | 2.72 | 2.380 |
| 3 | 28 | 3.57 | 2.147 |
| 3 | 28 | 5.25 | 1.949 |
| 3 | 28 | 7.40 | 2.282 |
| 3 | 28 | 9.48 | 1.143 |
| 3 | 28 | 11.48 | 1.098 |
| 3 | 28 | 23.32 | 1.902 |
| 4 | 28 | 0.00 | 1.752 |
| 4 | 28 | 1.25 | 1.776 |
| 4 | 28 | 2.17 | 4.643 |
| 4 | 28 | 3.17 | 3.282 |
| 4 | 28 | 4.25 | 2.260 |
| 4 | 28 | 6.25 | 2.285 |
| 4 | 28 | 8.00 | 1.864 |
| 4 | 28 | 10.17 | 2.164 |
| 4 | 28 | 12.17 | 1.833 |
| 4 | 28 | 24.33 | 1.901 |
| 6 | 28 | 0.00 | 2.922 |
| 6 | 28 | 1.17 | 2.274 |
| 6 | 28 | 2.25 | 2.510 |
| 6 | 28 | 3.17 | 3.335 |
| 6 | 28 | 4.00 | 2.486 |
| 6 | 28 | 6.08 | 3.377 |
| 6 | 28 | 8.08 | 4.753 |
| 6 | 28 | 10.00 | 4.470 |
| 6 | 28 | 12.00 | 4.692 |
| 6 | 28 | 24.08 | 3.107 |
| 7 | 28 | 0.00 | 6.445 |
| 7 | 28 | 1.17 | 6.604 |
| 7 | 28 | 2.00 | 4.770 |
| 7 | 28 | 3.08 | 4.463 |
| 7 | 28 | 4.33 | 6.394 |
| 7 | 28 | 5.42 | 6.668 |
| 7 | 28 | 6.17 | 6.315 |
| 7 | 28 | 10.00 | 3.766 |
| 7 | 28 | 12.00 | 7.489 |
| 7 | 28 | 24.58 | 6.984 |
| 8 | 28 | 0.00 | 1.376 |
| 8 | 28 | 1.67 | 1.095 |
| 8 | 28 | 2.50 | 0.874 |
| 8 | 28 | 3.42 | 0.955 |
| 8 | 28 | 4.28 | 0.781 |
| 8 | 28 | 6.25 | 0.858 |
| 8 | 28 | 8.17 | 1.134 |
| 8 | 28 | 10.08 | 1.017 |
| 8 | 28 | 12.25 | 2.315 |
| 8 | 28 | 24.33 | 0.775 |
| 9 | 28 | 0.00 | 3.049 |
| 9 | 28 | 1.25 | 1.529 |
| 9 | 28 | 2.25 | 1.337 |
| 9 | 28 | 3.25 | 1.151 |
| 9 | 28 | 5.33 | 2.201 |
| 9 | 28 | 7.33 | 2.793 |
| 9 | 28 | 9.00 | 2.220 |
| 9 | 28 | 11.25 | 2.183 |
| 9 | 28 | 24.17 | 1.970 |
| 10 | 28 | 0.00 | 0.984 |
| 10 | 28 | 1.17 | 0.827 |
| 10 | 28 | 2.25 | 1.123 |
| 10 | 28 | 3.13 | 0.843 |
| 10 | 28 | 4.33 | 0.714 |
| 10 | 28 | 6.12 | 1.190 |
| 10 | 28 | 8.33 | 0.949 |
| 10 | 28 | 10.25 | 1.813 |
| 10 | 28 | 12.08 | 0.759 |
| 10 | 28 | 24.08 | 1.735 |
| 11 | 28 | 0.00 | 1.173 |
| 11 | 28 | 1.25 | 1.083 |
| 11 | 28 | 2.17 | 0.951 |
| 11 | 28 | 3.20 | 0.830 |
| 11 | 28 | 4.25 | 0.879 |
| 11 | 28 | 6.13 | 1.126 |
| 11 | 28 | 8.22 | 1.171 |
| 11 | 28 | 10.17 | 1.667 |
| 11 | 28 | 12.12 | 0.855 |
| 11 | 28 | 23.92 | 5.577 |
| 12 | 28 | 0.00 | 7.080 |
| 12 | 28 | 0.83 | 5.774 |
| 12 | 28 | 1.75 | 6.827 |
| 12 | 28 | 2.90 | 5.976 |
| 12 | 28 | 3.83 | 8.649 |
| 12 | 28 | 5.83 | 7.441 |
| 12 | 28 | 7.83 | 6.406 |
| 12 | 28 | 9.75 | 7.007 |
| 12 | 28 | 11.83 | 4.732 |
| 12 | 28 | 23.87 | 9.634 |
| 13 | 28 | 0.00 | 3.486 |
| 13 | 28 | 1.00 | 1.975 |
| 13 | 28 | 1.83 | 2.413 |
| 13 | 28 | 2.92 | 2.386 |
| 13 | 28 | 3.83 | 1.043 |
| 13 | 28 | 5.83 | 2.384 |
| 13 | 28 | 7.83 | 2.860 |
| 13 | 28 | 9.83 | 1.476 |
| 13 | 28 | 11.83 | 2.367 |
| 13 | 28 | 24.33 | 1.900 |

| Cmin sheet | Day 1 | | | Day 28 | | | Day 1 | | | |
|---|---|---|---|---|---|---|---|---|---|---|
| | | TT | FT | | TT | FT | | | | |
| Subject No. | Time (hr) | Conc (ng/mL) | Conc (pg/mL) | Time (hr) | Conc (ng/mL) | Conc. (pg/mL) | TT Cmin | TT Tmin | FT Cmin | FT Tmin |
| 1 | 0.00 | 0.25 | 1.348 | 0.00 | 0.51 | 2.116 | 0.25 | 0 | 1.348 | 0 |
| 1 | 1.50 | 0.44 | 1.457 | 1.25 | 0.53 | 2.643 | | | | |
| 1 | 2.33 | 0.53 | 1.887 | 2.00 | 0.51 | 2.007 | | | | |
| 1 | 3.08 | 0.48 | 1.554 | 2.92 | 0.53 | 1.354 | | | | |

-continued

| | | | | | | | | | |
|---|---|---|---|---|---|---|---|---|---|
| 1 | 3.83 | 0.49 | 1.606 | 4.08 | 0.48 | 1.409 | | | |
| 1 | 5.97 | 0.39 | 1.524 | 6.08 | 0.55 | 1.269 | | | |
| 1 | 8.08 | 0.51 | 1.643 | 8.00 | 0.64 | 2.161 | | | |
| 1 | 9.87 | 0.47 | 1.905 | 10.08 | 0.72 | 3.252 | | | |
| 1 | 12.00 | 0.53 | 2.158 | 11.83 | 0.63 | 2.954 | | | |
| 1 | 24.50 | 0.37 | 3.321 | 24.05 | 0.57 | 4.104 | | | |
| 2 | 0.00 | 0.37 | 1.165 | 0.00 | 1.71 | 2.503 | 0.37 | 0 | 0.344 | 8.25 |
| 2 | 1.67 | 1.14 | 0.908 | 1.17 | 1.5 | 2.373 | | | |
| 2 | 2.47 | 1.38 | 0.830 | 2.08 | 1.83 | 2.629 | | | |
| 2 | 3.43 | 1.48 | 0.872 | 3.00 | 2.22 | 2.298 | | | |
| 2 | 4.50 | 1.27 | 0.897 | 4.25 | 2.78 | 2.818 | | | |
| 2 | 6.37 | 1.24 | 0.636 | 6.25 | 2.39 | 3.151 | | | |
| 2 | 8.25 | 0.91 | 0.344 | 7.83 | 1.89 | 2.473 | | | |
| 2 | 10.33 | 0.92 | 0.517 | 10.17 | 2.16 | 5.187 | | | |
| 2 | 12.17 | 0.86 | 0.392 | 12.17 | 1.47 | 1.980 | | | |
| 2 | 24.75 | 1.3 | 1.458 | 24.42 | 2.2 | 3.805 | | | |
| 3 | 0.00 | 0.13 | 1.182 | 0.00 | 1.66 | 3.802 | 0.13 | 0 | 1.083 | 8.2833 |
| 3 | 1.33 | | | 0.90 | 1.6 | 2.984 | | | |
| 3 | 2.08 | 0.31 | 1.804 | 1.62 | 1.67 | 4.209 | | | |
| 3 | 3.25 | 0.37 | 2.075 | 2.72 | 1.29 | 2.380 | | | |
| 3 | 4.30 | 0.34 | 3.125 | 3.57 | 1.51 | 2.147 | | | |
| 3 | 6.25 | 0.43 | 1.964 | 5.25 | 1.44 | 1.949 | | | |
| 3 | 8.28 | 0.45 | 1.083 | 7.40 | 1.18 | 2.282 | | | |
| 3 | 10.22 | 0.32 | 1.529 | 9.48 | 0.77 | 1.143 | | | |
| 3 | 12.20 | 0.43 | 1.546 | 11.48 | 0.75 | 1.098 | | | |
| 3 | 24.42 | 0.55 | 1.959 | 23.32 | 0.61 | 1.902 | | | |
| 4 | 0.00 | 0.09 | 0.262 | 0.00 | 0.91 | 1.752 | 0.09 | 0 | 0.262 | 0 |
| 4 | 1.75 | 0.40 | 0.564 | 1.25 | 0.85 | 1.776 | | | |
| 4 | 2.50 | 0.57 | 0.899 | 2.17 | 1.87 | 4.643 | | | |
| 4 | 3.38 | 0.58 | 1.127 | 3.17 | 2.5 | 3.282 | | | |
| 4 | 4.33 | 0.51 | 1.736 | 4.25 | 1.57 | 2.260 | | | |
| 4 | 6.33 | 0.57 | 0.584 | 6.25 | 1.16 | 2.285 | | | |
| 4 | 8.30 | 0.54 | 0.814 | 8.00 | 1.23 | 1.864 | | | |
| 4 | 10.17 | 0.56 | 0.630 | 10.17 | 1.31 | 2.164 | | | |
| 4 | 12.15 | 0.48 | 1.013 | 12.17 | 1.07 | 1.833 | | | |
| 4 | 24.50 | 0.55 | 1.279 | 24.33 | 0.77 | 1.901 | | | |
| 6 | 0.00 | 0.11 | 0.394 | 0.00 | 1.86 | 2.922 | 0.11 | 0 | 0.261 | 3.4167 |
| 6 | 1.33 | 0.86 | 0.383 | 1.17 | 1.67 | 2.274 | | | |
| 6 | 2.40 | 0.91 | 0.484 | 2.25 | 1.90 | 2.510 | | | |
| 6 | 3.42 | 0.83 | 0.261 | 3.17 | 2.89 | 3.335 | | | |
| 6 | 4.52 | 0.96 | 0.543 | 4.00 | 2.11 | 2.486 | | | |
| 6 | 6.50 | 1.20 | 0.949 | 6.08 | 2.72 | 3.377 | | | |
| 6 | 8.83 | 1.28 | 0.678 | 8.08 | 2.95 | 4.753 | | | |
| 6 | 10.33 | 0.75 | 0.358 | 10.00 | 2.48 | 4.470 | | | |
| 6 | 12.25 | 0.72 | 0.311 | 12.00 | 3.13 | 4.692 | | | |
| 6 | 24.58 | 0.92 | 0.834 | 24.08 | 1.90 | 3.107 | | | |
| 7 | 0.00 | 0.25 | 5.253 | 0.00 | 1.04 | 6.445 | 0.25 | 0 | 3.397 | 3.95 |
| 7 | 1.25 | 0.27 | 4.482 | 1.17 | 0.93 | 6.604 | | | |
| 7 | 1.92 | 0.27 | 6.859 | 2.00 | 0.85 | 4.770 | | | |
| 7 | 2.97 | 0.37 | 5.518 | 3.08 | 1.04 | 4.463 | | | |
| 7 | 3.95 | 0.41 | 3.397 | 4.33 | 1.37 | 6.394 | | | |
| 7 | 5.95 | 0.54 | 3.846 | 5.42 | 0.99 | 6.668 | | | |
| 7 | 8.00 | 0.57 | 4.190 | 6.17 | 1.12 | 6.315 | | | |
| 7 | 10.08 | 0.58 | 3.748 | 10.00 | 1.19 | 3.766 | | | |
| 7 | 12.00 | 0.57 | 4.929 | 12.00 | 1.19 | 7.489 | | | |
| 7 | 24.75 | 0.82 | 6.654 | 24.58 | 1.25 | 6.984 | | | |
| 8 | 0.00 | 0.00 | 0.175 | 0.00 | 1.30 | 1.376 | 0 | 0 | 0.175 | 0 |
| 8 | 1.08 | 0.50 | 0.713 | 1.67 | 1.01 | 1.095 | | | |
| 8 | 2.08 | 0.72 | 1.395 | 2.50 | 1.24 | 0.874 | | | |
| 8 | 3.00 | 0.74 | 0.666 | 3.42 | 1.29 | 0.955 | | | |
| 8 | 4.08 | 0.68 | 0.840 | 4.28 | 0.94 | 0.781 | | | |
| 8 | 6.08 | 0.60 | 0.377 | 6.25 | 0.93 | 0.858 | | | |
| 8 | 8.00 | 0.67 | 0.439 | 8.17 | 1.24 | 1.134 | | | |
| 8 | 10.00 | 0.54 | 0.451 | 10.08 | 0.68 | 1.017 | | | |
| 8 | 11.92 | 0.70 | 0.438 | 12.25 | 3.02 | 2.315 | | | |
| 8 | 24.00 | 0.91 | 0.750 | 24.33 | 0.73 | 0.775 | | | |
| 9 | 0.00 | 0.22 | 0.880 | 0.00 | 0.92 | 3.049 | 0.22 | 1.25 | 0.720 | 1.25 |
| 9− | 1.25 | 0.22 | 0.720 | 1.25 | 0.60 | 1.529 | | | |
| 9 | 2.25 | 0.47 | 1.044 | 2.25 | 0.60 | 1.337 | | | |
| 9 | 3.25 | 0.53 | 1.338 | 3.25 | 0.83 | 1.151 | | | |
| 9 | 4.20 | 0.73 | 1.405 | 5.33 | 1.58 | 2.201 | | | |
| 9 | 6.25 | 1.21 | 2.052 | 7.33 | 1.90 | 2.793 | | | |
| 9 | 8.25 | 1.25 | 1.736 | 9.00 | 1.91 | 2.220 | | | |
| 9 | 10.25 | 1.01 | 1.301 | 11.25 | 1.75 | 2.183 | | | |
| 9 | 12.22 | 0.94 | 1.973 | 24.17 | 1.24 | 1.970 | | | |
| 9 | 24.25 | 0.74 | 1.555 | | | | | | |
| 10 | 0.00 | 0.21 | 0.617 | 0.00 | 0.39 | 0.984 | 0.21 | 0 | 0.473 | 1 |
| 10 | 1.00 | 0.27 | 0.473 | 1.17 | 0.37 | 0.827 | | | |
| 10 | 1.93 | 1.12 | 1.781 | 2.25 | 0.69 | 1.123 | | | |

-continued

| | | | | | | | | | |
|---|---|---|---|---|---|---|---|---|---|
| 10 | 3.00 | 1.78 | 2.324 | 3.13 | 0.75 | 0.843 | | | |
| 10 | 4.08 | 0.67 | 1.219 | 4.33 | 0.77 | 0.714 | | | |
| 10 | 6.00 | 0.71 | 0.981 | 6.12 | 0.75 | 1.190 | | | |
| 10 | 7.93 | 1.34 | 1.716 | 8.33 | 0.84 | 0.949 | | | |
| 10 | 10.00 | 0.76 | 0.612 | 10.25 | 0.91 | 1.813 | | | |
| 10 | 11.88 | 0.61 | 0.670 | 12.08 | 0.53 | 0.759 | | | |
| 10 | 24.00 | 0.47 | 0.905 | 24.08 | 0.64 | 1.735 | | | |
| 11 | 0.00 | 0.02 | 0.091 | 0.00 | 0.29 | 1.173 | 0.02 | 0 | 0.091 | 0 |
| 11 | 1.25 | 0.23 | 0.835 | 1.25 | 0.27 | 1.083 | | | |
| 11 | 2.17 | 0.25 | 0.795 | 2.17 | 0.21 | 0.951 | | | |
| 11 | 3.42 | 1.3 | 3.350 | 3.20 | 0.37 | 0.830 | | | |
| 11 | 4.33 | 0.63 | 1.503 | 4.25 | 0.39 | 0.879 | | | |
| 11 | 6.50 | 0.76 | 1.716 | 6.13 | 0.49 | 1.126 | | | |
| 11 | 8.17 | 1.00 | 1.531 | 8.22 | 0.39 | 1.171 | | | |
| 11 | 10.50 | 0.81 | 1.355 | 10.17 | 0.67 | 1.667 | | | |
| 11 | 12.33 | 0.7 | 0.939 | 12.12 | 0.42 | 0.855 | | | |
| 11 | 24.20 | 3.05 | 6.861 | 23.92 | 2.72 | 5.577 | | | |
| 12 | 0.00 | 0.2 | 7.753 | 0.00 | 0.53 | 7.080 | 0.19 | 0.9167 | 5.987 | 2.67 |
| 12 | 0.92 | 0.19 | 6.322 | 0.83 | 0.46 | 5.774 | | | |
| 12 | 1.75 | 0.3 | 6.469 | 1.75 | 0.39 | 6.827 | | | |
| 12 | 2.67 | 0.38 | 5.987 | 2.90 | 0.42 | 5.976 | | | |
| 12 | 3.67 | 0.43 | 6.603 | 3.83 | 0.42 | 8.649 | | | |
| 12 | 5.67 | 0.37 | 7.137 | 5.83 | 0.5 | 7.441 | | | |
| 12 | 7.82 | 0.36 | 6.456 | 7.83 | 0.62 | 6.406 | | | |
| 12 | 9.58 | 0.34 | 5.998 | 9.75 | 0.47 | 7.007 | | | |
| 12 | 11.53 | 0.41 | 6.478 | 11.83 | 0.32 | 4.732 | | | |
| 12 | 23.38 | 0.79 | 10.876 | 23.87 | 0.63 | 9.634 | | | |
| 13 | 0.00 | 0.17 | 0.654 | 0.00 | 1.26 | 3.486 | 0.17 | 0 | 0.648 | 1.17 |
| 13 | 1.17 | 0.4 | 0.648 | 1.00 | 0.69 | 1.975 | | | |
| 13 | 2.17 | 0.79 | 1.286 | 1.83 | 0.92 | 2.413 | | | |
| 13 | 3.25 | 0.85 | 1.314 | 2.92 | 1.14 | 2.386 | | | |
| 13 | 4.25 | 1.20 | 2.089 | 3.83 | 0.82 | 1.043 | | | |
| 13 | 6.17 | 1.34 | 2.275 | 5.83 | 1.20 | 2.384 | | | |
| 13 | 8.17 | 1.00 | 1.992 | 7.83 | 1.48 | 2.860 | | | |
| 13 | 10.17 | 0.79 | 1.766 | 9.83 | 0.88 | 1.476 | | | |
| 13 | 12.17 | 1.18 | 2.120 | 11.83 | 1.64 | 2.367 | | | |
| 13 | 24.45 | 1.53 | 3.209 | 24.33 | 0.55 | 1.900 | | | |

| Cmin sheet Subject No. | Day 28 | | | | Day 28/Day 1 | |
|---|---|---|---|---|---|---|
| | TT Cmin | TT Tmin | FT Cmin | FT Tmin | Cmin TT | Cmin FT |
| 1 | 0.48 | 4.08 | 1.269 | 6.08 | 1.92 | 0.941 |
| 1 | | | | | | |
| 1 | | | | | | |
| 1 | | | | | | |
| 1 | | | | | | |
| 1 | | | | | | |
| 1 | | | | | | |
| 1 | | | | | | |
| 1 | | | | | | |
| 1 | | | | | | |
| 2 | 1.47 | 12.17 | 1.980 | 12.17 | 3.97 | 5.76 |
| 2 | | | | | | |
| 2 | | | | | | |
| 2 | | | | | | |
| 2 | | | | | | |
| 2 | | | | | | |
| 2 | | | | | | |
| 2 | | | | | | |
| 2 | | | | | | |
| 3 | 0.61 | 23.32 | 1.098 | 11.48 | 4.69 | 1.01 |
| 3 | | | | | | |
| 3 | | | | | | |
| 3 | | | | | | |
| 3 | | | | | | |
| 3 | | | | | | |
| 3 | | | | | | |
| 3 | | | | | | |
| 3 | | | | | | |
| 3 | | | | | | |
| 4 | 0.77 | 24.33 | 1.752 | 0.00 | 8.56 | 6.69 |
| 4 | | | | | | |
| 4 | | | | | | |
| 4 | | | | | | |
| 4 | | | | | | |

-continued

| | | | | | | |
|---|---|---|---|---|---|---|
| 4 | | | | | | |
| 4 | | | | | | |
| 4 | | | | | | |
| 4 | | | | | | |
| 4 | | | | | | |
| 6 | 1.67 | 1.17 | 2.274 | 1.17 | 15.2 | 8.71 |
| 6 | | | | | | |
| 6 | | | | | | |
| 6 | | | | | | |
| 6 | | | | | | |
| 6 | | | | | | |
| 6 | | | | | | |
| 6 | | | | | | |
| 6 | | | | | | |
| 7 | 0.85 | 2.00 | 3.766 | 10.00 | 3.40 | 1.11 |
| 7 | | | | | | |
| 7 | | | | | | |
| 7 | | | | | | |
| 7 | | | | | | |
| 7 | | | | | | |
| 7 | | | | | | |
| 7 | | | | | | |
| 7 | | | | | | |
| 8 | 0.68 | 10.08 | 0.775 | 24.33 | nc | 4.43 |
| 8 | | | | | | |
| 8 | | | | | | |
| 8 | | | | | | |
| 8 | | | | | | |
| 8 | | | | | | |
| 8 | | | | | | |
| 8 | | | | | | |
| 8 | | | | | | |
| 9 | 0.6 | 3.50 | 1.151 | 3.25 | 2.73 | 1.60 |
| 9– | | | | | | |
| 9 | | | | | | |
| 9 | | | | | | |
| 9 | | | | | | |
| 9 | | | | | | |
| 9 | | | | | | |
| 9 | | | | | | |
| 9 | | | | | | |
| 10 | 0.37 | 1.17 | 0.714 | 4.33 | 1.76 | 1.51 |
| 10 | | | | | | |
| 10 | | | | | | |
| 10 | | | | | | |
| 10 | | | | | | |
| 10 | | | | | | |
| 10 | | | | | | |
| 10 | | | | | | |
| 11 | 0.21 | 2.17 | 0.830 | 3.20 | 10.5 | 9.12 |
| 11 | | | | | | |
| 11 | | | | | | |
| 11 | | | | | | |
| 11 | | | | | | |
| 11 | | | | | | |
| 11 | | | | | | |
| 11 | | | | | | |
| 12 | 0.32 | 11.83 | 4.732 | 11.83 | 1.68 | 0.79 |
| 12 | | | | | | |
| 12 | | | | | | |
| 12 | | | | | | |
| 12 | | | | | | |
| 12 | | | | | | |
| 12 | | | | | | |
| 12 | | | | | | |
| 12 | | | | | | |
| 13 | 0.55 | 24.33 | 1.043 | 3.83 | 3.24 | 1.61 |
| 13 | | | | | | |
| 13 | | | | | | |
| 13 | | | | | | |

-continued

| |
|---|
| 13 |
| 13 |
| 13 |
| 13 |
| 13 |
| 13 |

FT is free testosterone;
TT is total testosterone;
d0 is day zero (=day 1), first day gel therapy applied at 8 am (0 hr);
gel applied at ~8 am 1 cc/d × 28 days; all at 1 dose 0.75 g of 1% w/w T gel;
blood draws on day 1 and day 28 at 0 hr [baseline on d1], 1, 2, 3, 4, 6, 8, 10, 12, 24 hr (10 time points);

| Cmin sheet | | Day 1 | | | | Day 28 | | | | Day 28/Day 1 | |
|---|---|---|---|---|---|---|---|---|---|---|---|
| | | TT Cmin | TT Tmin | FT Cmin | FT Tmin | TT Cmin | TT Tmin | FT Cmin | FT Tmin | Cmin TT | Cmin FT |
| All Subjects | Mean | 0.168 | | 1.23 | | 0.715 | | 1.78 | | 5.24 | 3.61 |
| | SD | 0.105 | | 1.75 | | 0.441 | | 1.27 | | 4.35 | 3.19 |
| | Median | 0.180 | 0 | 0.561 | 1.21 | 0.605 | 7.08 | 1.21 | 5.21 | 3.40 | 1.60 |
| | Min | 0 | 0 | 0.091 | 0 | 0.21 | 1.17 | 0.714 | 0 | 1.68 | 0.790 |
| | Max | 0.370 | 1.25 | 5.99 | 8.28 | 1.67 | 24.3 | 4.73 | 24.3 | 15.2 | 9.12 |
| Without Subjects 7 and 12 | Mean | 0.157 | | 0.541 | | 0.741 | | 1.29 | | 5.84 | 4.14 |
| | SD | 0.111 | | 0.412 | | 0.467 | | 0.536 | | 4.60 | 3.24 |
| | Median | 0.150 | 0 | 0.409 | 1.09 | 0.605 | 7.08 | 1.12 | 4.08 | 3.97 | 3.02 |
| | Min | 0 | 0 | 0.091 | 0 | 0.210 | 1.17 | 0.714 | 0 | 1.76 | 0.941 |
| | Max | 0.370 | 1.25 | 1.35 | 8.28 | 1.67 | 24.3 | 2.27 | 24.3 | 15.2 | 9.12 |

| Cmin sheet | Subject No. | Day 1 | | | | Day 28 | | | | RATIO Day 28/Day 1 | | DIFFERENTIAL Day 28/Day 1 | |
|---|---|---|---|---|---|---|---|---|---|---|---|---|---|
| | | TT Cmin | TT Tmin | FT Cmin | FT Tmin | TT Cmin | TT Tmin | FT Cmin | FT Tmin | Cmin TT | Cmin FT | Cmin TT | Cmin FT |
| | 1 | 0.25 | 0 | 1.348 | 0 | 0.48 | 4.08 | 1.269 | 6.08 | 1.92 | 0.941 | 0.23 | −0.079 |
| | 2 | 0.37 | 0 | 0.344 | 8.25 | 1.47 | 12.17 | 1.980 | 12.17 | 3.97 | 5.76 | 1.1 | 1.636 |
| | 3 | 0.13 | 0 | 1.083 | 8.2833 | 0.61 | 23.32 | 1.098 | 11.48 | 4.69 | 1.01 | 0.48 | 0.015 |
| | 4 | 0.09 | 0 | 0.262 | 0 | 0.77 | 24.33 | 1.752 | 0.00 | 8.56 | 6.69 | 0.68 | 1.490 |
| | 6− | 0.11 | 0 | 0.261 | 3.4167 | 1.67 | 1.17 | 2.274 | 1.17 | 15.2 | 8.71 | 1.56 | 2.013 |
| | 7 | 0.25 | 0 | 3.397 | 3.95 | 0.85 | 2.00 | 3.766 | 10.00 | 3.40 | 1.11 | 0.6 | 0.369 |
| | 8 | 0 | 0 | 0.175 | 0 | 0.68 | 10.08 | 0.775 | 24.33 | nc | 4.43 | 0.68 | 0.600 |
| | 9 | 0.22 | 1.25 | 0.720 | 1.25 | 0.6 | 3.50 | 1.151 | 3.25 | 2.73 | 1.60 | 0.38 | 0.431 |
| | 10 | 0.21 | 0 | 0.473 | 1 | 0.37 | 1.17 | 0.714 | 4.33 | 1.76 | 1.51 | 0.16 | 0.241 |
| | 11 | 0.02 | 0 | 0.091 | 0 | 0.21 | 2.17 | 0.830 | 3.20 | 10.5 | 9.12 | 0.19 | 0.739 |
| | 12 | 0.19 | 0.9167 | 5.987 | 2.67 | 0.32 | 11.83 | 4.732 | 11.83 | 1.68 | 0.79 | 0.13 | −1.255 |
| | 13 | 0.17 | 0 | 0.648 | 1.17 | 0.55 | 24.33 | 1.043 | 3.83 | 3.24 | 1.61 | 0.38 | 0.395 |

| | | Day 1 | | | | Day 28 | | | | Day 28/Day 1 Ratios | | | |
|---|---|---|---|---|---|---|---|---|---|---|---|---|---|
| | | TT Cmin | TT Tmin | FT Cmin | FT Tmin | TT Cmin | TT Tmin | FT Cmin | FT Tmin | Cmin TT | Cmin FT | Day 28/Day 1 Differential | |
| All Subjects | Mean | 0.168 | | 1.23 | | 0.715 | | 1.78 | | 5.24 | 3.61 | | |
| | SD | 0.105 | | 1.75 | | 0.441 | | 1.27 | | 4.35 | 3.19 | | |
| | Median | 0.180 | 0 | 0.561 | 1.21 | 0.605 | 7.08 | 1.21 | 5.21 | 3.40 | 1.60 | | |
| | Min | 0 | 0 | 0.091 | 0 | 0.21 | 1.17 | 0.714 | 0 | 1.68 | 0.790 | | |
| | Max | 0.370 | 1.25 | 5.99 | 8.28 | 1.67 | 24.3 | 4.73 | 24.3 | 15.2 | 9.12 | | |
| Without Subjects 7 and 12 | Mean | 0.157 | | 0.541 | | 0.741 | | 1.29 | | 5.84 | 4.14 | | |
| | SD | 0.111 | | 0.412 | | 0.467 | | 0.536 | | 4.60 | 3.24 | | |
| | Median | 0.150 | 0 | 0.409 | 1.09 | 0.605 | 7.08 | 1.12 | 4.08 | 3.97 | 3.02 | | |
| | Min | 0 | 0 | 0.091 | 0 | 0.210 | 1.17 | 0.714 | 0 | 1.76 | 0.941 | | |
| | Max | 0.370 | 1.25 | 1.35 | 8.28 | 1.67 | 24.3 | 2.27 | 24.3 | 15.2 | 9.12 | | |

Example 2

This study will be performed to confirm the results of the trial discussed in Example 1 above. The study will be employ a randomized, double blind placebo controlled design in eighty to one hundred patients. In the previous open label study of 12 patients, we tested the hypothesis that the fibromyalgia muscle pain and fatigue symptoms of women, aged 40-60 with Fibromyalgia Syndrome (FMS), are caused by abnormally low circulating levels of testosterone. Further, we tested the hypothesis that treatment of FMS patients with testosterone gel delivered transdermally will decrease the fibromyalgia-related pain and fatigue in these patients. The goals for this blinded efficacy study are very similar. Specifically, the goals are to conduct a placebo controlled study in FMS. for testosterone treatment for fibromyalgia-related pain and fatigue in FMS patients. Patients will be treated for 3 months, have a possible extension to 6 months, and will employ symptomatic FMS efficacy endpoints, as in Example 1.

This study will be performed to confirm the dose of testosterone gel that is appropriate for fibromyalgia subjects. The doses of testosterone gel used in the previous study approximate the blood levels expected for testosterone replacement therapy in Fibromyalgia Syndrome (FMS) patients. The drug dose is based on the testosterone gel treatment in the 12 patients, as discussed in Example 1. In our previous trial, FMS patients were on the drug for 28 days and were tested for serum testosterone levels pharmacokinetically over a 24 hr period both on day 1 and at the end of treatment on day 28. The dose of drug used for that study resulted in increased free testosterone serum levels that were largely within the reference range.

The planned study will be performed to confirm the safety of the dose of testosterone gel and the blood levels achieved with those doses. In this study, safety checks will take place at weeks 4, 8, and 12 to monitor the levels of testosterone in the blood. Dose reduction is an option if needed for safety purposes. A dose increase is an option, within the limitations of safety, if needed for efficacy.

This study will be performed to assess testosterone blood levels due to the testosterone treatment. The study will further continue to assess the interpatient variation of testosterone blood levels achieved at the doses of testosterone used and identify any remaining confounding factors when assessing testosterone levels.

The planned twelve-week research study will look at whether testosterone replacement therapy can lessen the symptoms of fibromyalgia over 3-6 months' time. Patients that are selected to participate in the study will receive either testosterone gel or placebo gel and undergo an evaluation and blood tests once every four weeks. In addition, study participants will complete patient questionnaires once every four weeks, take part in an exercise program and fill out daily medicine and exercise logs.

The target patients for this study will be 40-60 year old women who have been diagnosed as having fibromyalgia. The patients can be pre- or post-menopausal, but should not be using hormone therapy (or will be willing to cease such therapy). In addition, the patients should not use St. John's Wort, antidepressants, ginger root (or will be willing to cease such use). In addition, in order to be selected for the study, patients will be required to exercise at least 20 minutes per day, five days a week, including stretching and aerobic exercise (walking, running, bicycling, climbing stairs, etc.).

The physical examination used to select participants for the study will include a "tender point" examination, which tests the intensity of fibromyalgia-related muscle pain for each of the 18 commonly recognized tender points that fibromyalgia patients are known to have. The tender point examination will be repeated every four weeks.

Prospective study participants will be notified of the risks, and the likelihood of their occurrence. The risks include increased libido (likely to occur); deepening of the voice, increased facial hair, temporal balding, acne, menstrual irregularities, lipid abnormalities and heart disease; liver toxicity (unlikely to occur); and hepatocellular carcinoma (rare occurrence). Patients whose blood levels are maintained within the appropriate reference range for androgens are unlikely to have the toxicity risks associated with blood levels above the reference range.

This double blinded, placebo-controlled study with dose titration for safety (see below) is designed to show in a controlled study that testosterone replacement therapy results in decreased fibromyalgia-related pain and fatigue in women with Fibromyalgia Syndrome (FMS). Female patients aged 40-60 who have been diagnosed with FMS and meet other eligibility criteria will be considered for this Phase I/II study. A total of 80-100 outpatients will be enrolled, 40-50 for each arm, drug versus placebo, and with randomization to initial treatment versus placebo. Menstruating women will be started on drug within 10 days of their d1 of menses to initially control for reproductive endocrine state. A dose of testosterone gel, about 800 mg gel at 0.8% w/w testosterone/gel (about 6.4 mg testosterone; at the commonly accepted 10% bioavailability of drug in a gel=0.64 mg bioavailable testosterone, that is essentially equivalent to that previously determined by us as appropriate for women (about 750 mg gel of 1% w/w testosterone/gel) versus placebo gel, will be applied to the subject's abdominal skin at 0 hr on Day 1 (at 8:00 AM), and each morning thereafter once a day for 4 weeks. At 4 weeks, after serum testing for testosterone levels, gel will be adjusted upward from 800 mg to 1200 mg for patients whose levels remain in the low range (S about 1.9 pg/mL free testosterone, DSL test), and the gel will be adjusted downward from about 800 mg to about 400 mg for patients whose levels are high (>about 3.3 pg/mL free testosterone, DSL test). Serum will be tested again at 8 weeks and the dose readjusted similarly if necessary. Equivalent values will be used if Mayo Medical Labs testing is used.

This dose adjustment is important due to the individual variation we have found between FMS subjects in response to testosterone therapy. This variation could be due to variation in catabolism rates, SHBG affinity, etc. Our preliminary data (Example 1) allow us to predict that we can safely maintain subjects on a dose between 1-3 packets of about 400 mg/packet about 0.8% testosterone gel per day. Testosterone levels will be blinded to treatment staff and study investigators via use of a "Study Dosing Coordinator" who is distinct from the Study Coordinator. The three month open label (no placebo) continuation study may be extended to provide 6 month safety data for those patients originally on drug, and to allow patients on placebo to go on drug for 3 months. The dose will be adjusted similarly to how adjustments were made in the first 12 weeks, and we will use the same approach for testing.

To test for serum levels of testosterone (total and free), the study coordinator will take blood samples (7 mL) by venipuncture prior to the study (for eligibility) and at 4, 8, and 12 weeks (and at 16, 20, 24 weeks if the extension study is performed), between 8:00 and 9:00 AM prior to application of gel and after fasting since midnight the evening before. Estradiol will be tested at d1, 12 wks (and 24 wk if the extension study is performed) to rule out conversion from testosterone to estradiol in the circulation via aromatase. The limited data available indicates that no such conversion takes place. Subjects will be instructed to fast from midnight the evening before for all blood draws.

For general health parameters, pre-study baseline samples and end-of-study samples will be collected at screening (Visit 1), 12 weeks (and 24 weeks for the extension study) for standard test panels (see Appendix 1): cardiac health (Lipid Profile: total cholesterol, HDL, LDL, triglyceride), liver function (hepatic function panel: ALT, ALP, AST, albumin, TBil, DBil), kidney function (BUN, creatinine) and CBC (to obtain hemoglobin levels since androgens are known to stimulate the production of red blood cells by enhancing erythropoietin production. FSH will be tested at the screening phase to discriminate pre- and post-menopausal women and to allow for subgrouping in the analysis phase (high levels indicate the patient is postmenopausal). As noted previously, premenopausal women will be entered into drug treatment within 10d of d1 of menses to initially control for endocrine state.

Testing for total testosterone serum levels will be conducted, as well as for free testosterone serum levels. Testing for total testosterone is most frequently done due to its lower cost, but free testosterone levels allow for assessment of the biologically active compartment. Although free testosterone levels have been found to correlate well with total testosterone levels, both are required for full analysis and both will be tested here. Serum estradiol levels in these women were found to be well within the reference range. Dihydrotestosterone (DHT) will not be measured since testosterone is converted to DHT within cells, and testosterone is the norm for testing in women. DHT is dependent on testosterone levels and can be assumed to correlate with testosterone levels.

Sex hormone binding globulin (SHBG) reversibly binds testosterone resulting in a bioavailable form (bioavailable testosterone is composed of free testosterone+testosterone loosely associated with globulin) versus a non-bioavailable form (SHBG bound). Testosterone and its more form dihydrotestosterone have a higher affinity than estradiol for SHBG (Becker, p 938). Androgens can decrease the binding affinity of SHBG for hormone, resulting in an increased bioavailability of both 17beta-hydroxyandrogens (testosterone and DHT) and estradiol (Becker, p 837). Our testing of estradiol will allow us to determine how testosterone therapy affects serum estradiol levels in our subjects. Estrogen administration is associated with a decrease in bioavailable testosterone (Davis 1997). The patients studied here will not be on estrogen or any other hormone therapy at the time of testosterone therapy.

Testosterone formulated in about an 0.8% (w/w) hydroalcoholic gel by an FDA licensed manufacturer, at about 800 mg gel/day (see details under "Dose of testosterone gel" below), will be prescribed for transdermal delivery. The initial dose at about 800 mg will be adjusted to about 400 mg or about 1200 mg as specified above based on free testosterone serum levels tested at 4 week intervals. A packet-based or metered-dose method can be used to ensure delivery of an accurate quantity of gel. Other delivery systems can be contemplated as well, as long as the desired blood levels are met. The gel will be applied to abdominal skin, above the waistline, for transdermal delivery by percutaneous absorption. The gel dries in minutes and is colorless, comfortable and non-staining. The form of testosterone used will be USP grade material of a composition identical in potency to a currently marketed transdermal gel which is FDA approved for men with hypogonadism.

The gel proposed for this study will be similar in composition to the marketed gel, but packaged and titrated for a female dosage regimen. The gel will be compounded at an FDA-approved manufacturing site using GMP conditions appropriate for this stage of development, and will be monitored for stability for the duration of the study. The gel will be metered using a filled packet calibrated to deliver the required dose. The packets will be assembled in kits with the appropriate number of packets as determined by the Study Dose Coordinator, and with package insert instructions for the patient and scissors to snip the end of the packet.

Testosterone is a schedule C-III controlled substance as defined by the Anabolic Steroids Control Act. The materials must be produced under a DEA license. The amounts dispensed are insufficient for abuse potential, and the samples will be itemized and accounted for. All unused materials containing the scheduled substance testosterone must be returned to the Researcher at the end of the study.

A transdermal route of delivery should provide benefits to the patient beyond those found with oral delivery. The hormone is delivered over a more sustained time and at lower doses with improved bioavailability, thereby reducing the risk of hepatotoxic side effects. The injectable or transdermal (gel, patch) forms of hormone largely circumvent the possible hepatotoxicity issues associated with orally administered hormones. Currently, the oral route of delivery is the predominant route used by women on estrogen/progestin sex steroid hormone replacement therapy. Delivery of testosterone via gel should be superior to oral delivery. With regards to different vehicles for transdermal delivery, a testosterone patch is currently being studied in women for AIDS related wasting syndrome (Miller 1998, Javanbakht 2000). We prefer transdermal delivery via gel, rather than patch, which will avoid the local skin irritation experienced by patients using the patch system since ~30% of patients get contact dermatitis with the patch (P&G's Intrinsa testosterone patch for the subset of female sexual dysfunction (FSD) called Hypoactive Sexual Desire Disorder (HSDD).

Relatively high doses of androgens were given to patients in the earliest studies by others. The current thinking is to use these drugs for amelioration of hormone deficiency at relatively low doses in an attempt to reconstitute normal levels. The planned study is in keeping with this minimalist rationale. To determine the appropriate dose for our previous pharmacokinetic study using FMS patients (Example 1), we estimated the dose of testosterone gel based on the FDA approved testosterone gel product. Our pharmacokinetic methodology was similar to that used for men in prior clinical trials.

All patients will be started with 2 packets of about 0.8% Testosterone or Placebo gel per day for the first 4 weeks. Each packet has 400 mg of 0.8% Testosterone gel (3.2 mg Testosterone, to deliver 10% or 320 μg bioavailable Testosterone) or 400 mg Placebo gel in it. The patient will be shown where to rub the gel on her abdomen. After the 4 wk blood draw, any patient who tests>3.3 pg/mL for serum free Testosterone (HiT, DSL test), decreases dose by 1 gel packet/d; any patient who tests≤1.9 pg/mL for serum free Testosterone (LoT, DSL test), increases dose by 1 gel packet/d. Equivalent cut-off levels will be used if Mayo Medical Labs testing is done instead. The decision to adjust the testosterone dose will be made again after the 8 wk blood draw. Our preliminary data allow us to predict that we can safely maintain subjects on a dose between 1-3 packets of 400 mg 0.8% testosterone/packet per day. In order to maintain the blind for the patient and the treating study staff, placebo patients will be split into three groups at week 4, with a third given 1 packet, a third maintained at 2 packets and a third given 3 packets of Placebo.

The trial will be scheduled for 12 weeks to start, with a possibility of extending the trial to a total of 24 weeks. If the study is able to be extended, all patients will receive open label testosterone starting at 12 weeks, with the 12 week time point serving as the baseline for the Placebo patients. Placebo patients will receive 2 packets of Testosterone gel for the next 4 weeks. Possible dose adjustment for these patients will take place after 16 weeks and again after 20 weeks, based on achieved free serum testosterone levels. Adjustments for all patients will be made based on the same criteria as described above for weeks 4 and 8. For the subjects who were on drug during the first 12 weeks, the additional 12 weeks of continuation will provide confirmation of efficacy and extended safety data. For the Placebo patients, the continuation study will ensure all patients in the study have a trial of active therapy.

The Study Coordinator or Study Resident will administer the FMS Preliminary Patient Questionnaire (FIG. 7). The Study Coordinator or Study Resident will fill out the Eligibility Criteria Form (FIG. 8) and give it to the physician. The Dosing Coordinator will fill out the Dose Coordinator Serum Testosterone Values Form (FIG. 9) and use it to communicate with the pharmacist and adjust the dose.

Figure 10:
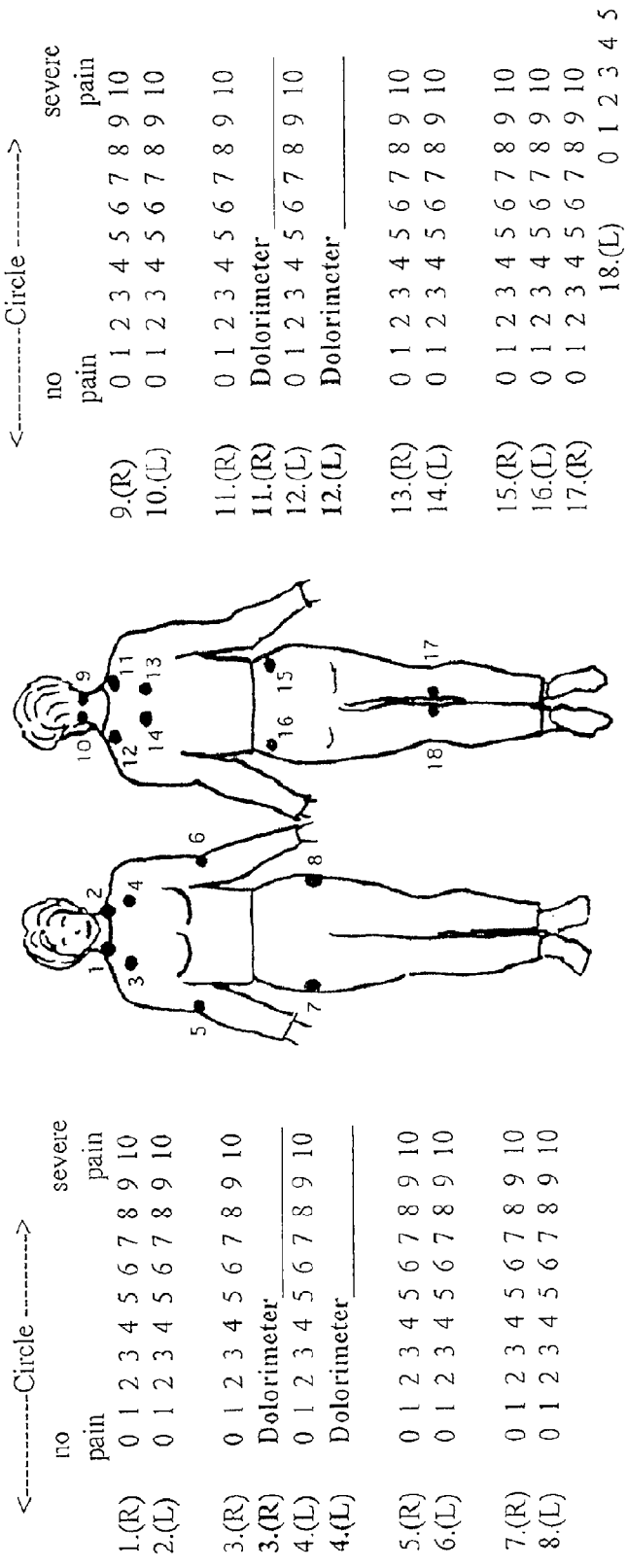
FIG. 10 is an example of a Physician Evaluation Form (Tender Points).

The physician will fill out a Physician Evaluation Form (FIG. 10) that includes the FMS Tender Point Exam prior to therapy to verify that the patient fulfills the criteria for FMS, as defined by the American College of Rheumatology, and to document the intensity of fibromyalgia-related muscle pain for each of the 18 commonly recognized tender points that patients with FMS are known to have (Okifuji, Turk 1997). A dolorimeter will be used to quantify a subset of painful points, similar to the tender point subsets used in our previous PK study: second costochondral (rib-cartilage) junction and trapezius at the midpoint of the upper border, both for right and left sides, thus 4 TP sites. The Physician's Form (FIG. 10) will be filled out at the end of the study at 12 weeks (and 24 weeks, if necessary), to allow a comparison of parameters before and after treatment.

The study coordinator (or study designated resident) will administer a Patient Questionnaire Form (FIGS. 12A-12D) to the study patient to assess their symptoms and level of fibromyalgia-related pain in a semi-quantitative manner, prior to therapy and at the end of the 12 weeks of therapy (or at the time of early dropout from the study, and at 24 weeks if the extension study is done) to allow a comparison of parameters before and after treatment. Our Patient Questionnaire Form (FIGS. 12A-12D) is the same form as that used in our previous pharmacokinetic and efficacy study (Example 1) and is based on the validated Fibromyalgia Impact Questionnaire or FIQ (Burckhardt 1991). However, this form includes additional questions on gynecological history, exercise habits and use of analgesics, for example. The questionnaires and physical exam together include evaluation parameters that are common to published and validated FMS patient questionnaires, such as fibromyalgia-related pain (e.g., tender point exam), sleeplessness, feeling refreshed, fatigue, headache and stiffness (Wolfel 990; Goldenberg 1996; Burckhardt 1991). A 100 mm visual analogue scale (VAS) will be used.

An initial summary assessment of the patient's general health via standard physical exam will be noted on the Physician's General Health Form (FIG. 11). For purposes of analysis, the study patient will be administered the MOS SF-36 (Medical Outcomes Study Short Form with 36 questions, FIGS. 13A-13F) to assess global health (Ware 1992, Picavet 2004). This validated form was favorably reviewed by the FDA for evaluation of the general functional capacity to be used along with the pain instruments. It will be administered by the study coordinator prior to study for baseline, and at 12 wk (and 24 wk) at the end of study. The SF-36 health survey form is a standard instrument for assessment of global health.

The Mannerkorpi functional movement test will be administered by the study coordinator prior to study for baseline, and at 12 wk (and 24 wk) at the end of study. This instrument was chosen because of its outstanding ability to discriminate between FMS subjects and a control group for range of motion and fibromyalgia-related pain perceived during range-of-motion testing using a VAS scale of 1-100 mm (Mannerkorpi 1999, P values at 0.0001 for pain perceived). This instrument has been validated for FMS patients.

Figure 18:
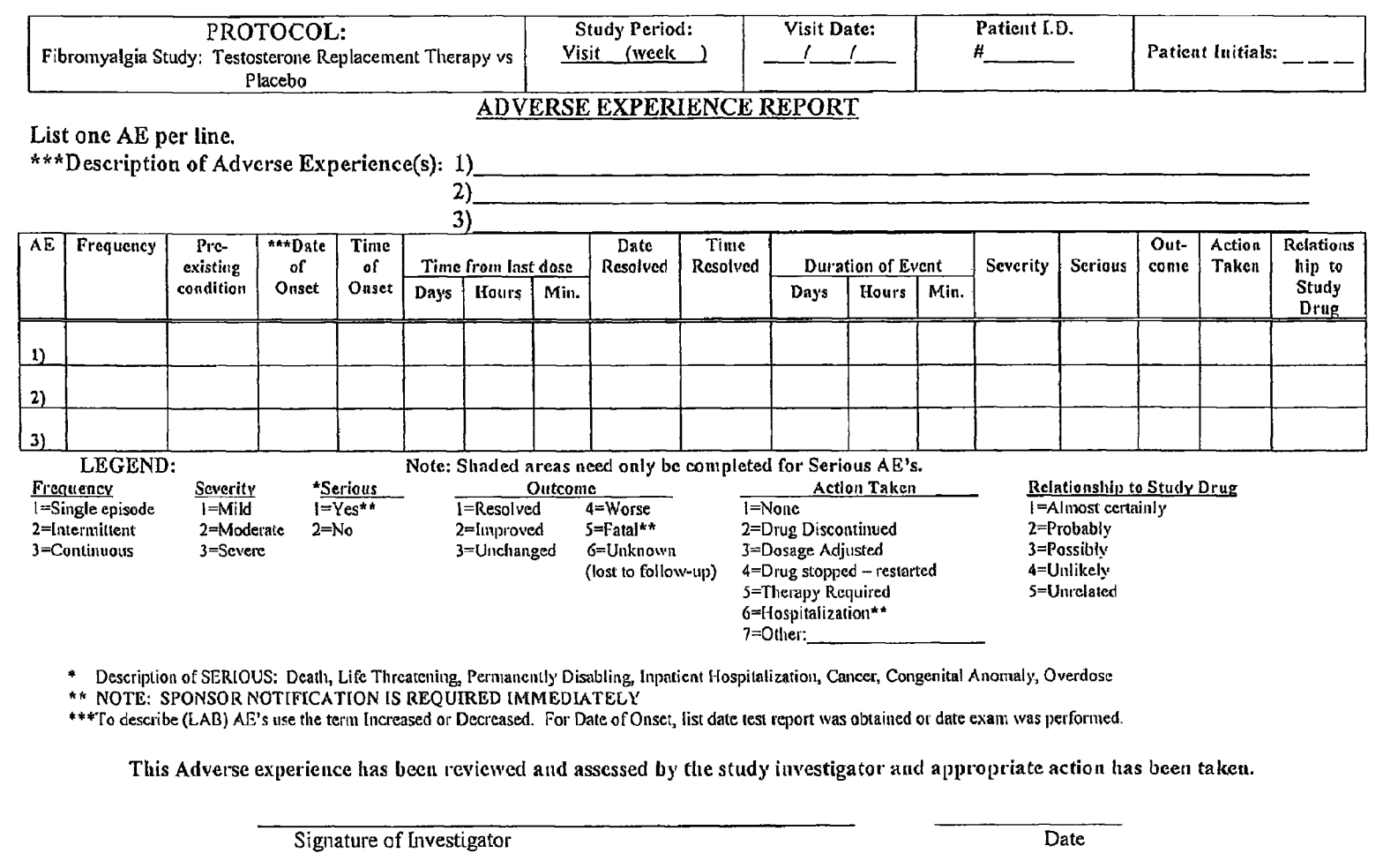

Patients will also be followed for changes in blood pressure and weight. At the end of the study, analyses will be conducted to show: 1) the percentage of patients achieving>30% versus>50% improvement in their pain scores by VAS, 2) the percentage of patients in the active arm who would like to continue on with their same medication, 3) versus the percentage of patients in the placebo arm who would like to continue on with their same medication, 4) an analysis of use of pain relief network pain medication in both arms, and 5) an analysis of dropouts due to lack of efficacy from both arms. The patients will be required to complete the examinations, questionnaires, blood draws, study gel logs (FIG. 16), and exercise logs (FIG. 17). The patients, if any occur, will also be required to fill out an Adverse Event Form (FIG. 18). Each adverse event will be investigated by the study investigator.

Other forms that can be administered by the physician or Dose Coordinator for this study include the FMS Movement Test Form (FIGS. 14A-14B).

Having now fully described the invention, it will be understood by those of ordinary skill in the art that the same can be performed within a wide and equivalent range of conditions, formulations and other parameters without affecting the scope of the invention or any embodiment thereof. All patents, patent applications, and publications cited herein are fully incorporated by reference in their entirety.

What is claimed is:

1. A method of alleviating the symptoms of a condition which is associated with deficient serum testosterone levels in a female human patient in need thereof comprising transdermally administering daily, to said patient suffering from deficient serum testosterone levels, a safe and effective amount of testosterone which is both effective for alleviating the female patient's condition associated with testosterone deficiency and for consistently raising the female patient's serum testosterone levels from baseline level to the middle or upper level of the female reference range, wherein the composition contains a daily dose of testosterone and is formulated to provide steady state total testosterone serum levels without raising free testosterone serum levels or twenty-four hour free testosterone AUC above the levels required for both therapeutic efficacy and safety, wherein said symptoms are at least one or more of muscle pain, stiffness, fatigue, tiredness, and lack of libido.

2. A method of reducing fibromyalgia-related tender point pain in a female human patient in need thereof, comprising transdermally administering daily, to said patient suffering from deficient serum testosterone levels, a safe and effective amount of testosterone which is both effective for reducing the female patient's fibromyalgia-related tender point pain and for consistently raising the female patient's serum testosterone levels from baseline level to the middle or upper level of the female reference range, wherein the composition contains a daily dose of testosterone and is formulated to provide steady state total testosterone serum levels without raising free testosterone serum levels or twenty-four hour free testosterone AUC above the levels required for both therapeutic efficacy and safety.

3. A method of increasing fibromyalgia-related tender point pain threshold in a female human patient in need thereof, comprising transdermally administering daily, to said patient suffering from deficient serum testosterone levels, a safe and effective amount of testosterone which is both effective for increasing the female patient's fibromyalgia-related tender point pain threshold and for consistently raising the female patient's serum testosterone levels from baseline level to the middle or upper level of the female reference range, wherein the composition contains a daily dose of testosterone and is formulated to provide steady state total testosterone serum levels without raising free testosterone serum levels or twenty-four hour free testosterone AUC above the levels required for both therapeutic efficacy and safety.

4. The method of claim 1, wherein the testosterone is selected from the group consisting of testosterone, dihydrotestosterone, methyltestosterone, and testosterone esters.

5. The method of claim 4, wherein the testosterone ester is selected from the group consisting of testosterone enanthate and testosterone cypionate.

6. The method of claim 1, wherein the testosterone is administered in a transdermal daily unit dose of about 1.0 mg to about 12.8 mg of the testosterone.

7. The method of claim 6, wherein the daily unit dose of the testosterone is from about 2.5 mg to about 10.0 mg.

8. The method of claim 7, wherein the daily unit dose of the testosterone is from about 3.2 mg to about 9.6 mg.

9. The method of claim 8, wherein the daily unit dose of the testosterone is from about 6.0 mg to about 8.0 mg.

10. The method of claim 1, wherein the daily unit dose of the testosterone is selected to maintain steady state total testosterone serum levels within a range of between about 0.9 ng/mL to about 1.4 ng/mL for at least 24 hours after administration.

11. The method of claim 10, wherein the free testosterone serum levels are raised to about 1.00 pg/mL to about 3.30 pg/mL and the twenty-four hour free testosterone AUC levels are raised to about 40.00 pg-h/mL to about 65.00 pg-h/mL.

12. The method of claim 1, wherein the concentration of testosterone is present in an amount of about 1% on a weight basis.

13. The method of claim 1, wherein the condition which is associated with deficient serum testosterone levels is selected from the group consisting of fibromyalgia, chronic fatigue syndrome, and decreased sexual desire; and the safe female effective unit dose is an amount which will raise the female human patient's steady state serum androgen level and avoid side effects.

14. The method of claim 1, wherein the composition delivers a therapeutically effective and safe daily amount of the testosterone to the patient's serum over each 24 hour period to alleviate the patient's symptoms and avoid side effects.

15. The method of claim 14, wherein the testosterone is administered in a transdermal daily unit dose of about 1.0 mg to about 12.8 mg of the testosterone, wherein the administration delivers a therapeutically effective daily amount of the testosterone to the patient's serum over each 24 hour period to alleviate the patient's symptoms and avoid side effects.

* * * * *